US012697303B2

(12) United States Patent
Singh

(10) Patent No.: US 12,697,303 B2
(45) Date of Patent: *Aug. 4, 2026

(54) SOLID COMPOSITION

(71) Applicant: University of Lancashire, Preston (GB)

(72) Inventor: Kamalinder Singh, Preston (GB)

(73) Assignee: University of Lancashire, Preston (GB)

( * ) Notice: Subject to any disclaimer, the term of this patent is extended or adjusted under 35 U.S.C. 154(b) by 37 days.

This patent is subject to a terminal disclaimer.

(21) Appl. No.: 18/378,498

(22) Filed: Oct. 10, 2023

(65) Prior Publication Data

US 2024/0277618 A1 Aug. 22, 2024

Related U.S. Application Data

(63) Continuation of application No. 16/754,061, filed as application No. PCT/GB2018/052855 on Oct. 5, 2018, now Pat. No. 11,839,687.

(30) Foreign Application Priority Data

Oct. 6, 2017 (GB) ..................................... 1716419

(51) Int. Cl.
| | |
|---|---|
| A61K 9/14 | (2006.01) |
| A23L 33/12 | (2016.01) |
| A61K 9/00 | (2006.01) |
| A61K 9/16 | (2006.01) |
| B01J 13/08 | (2006.01) |

(52) U.S. Cl.
CPC .............. *A61K 9/145* (2013.01); *A23L 33/12* (2016.08); *A61K 9/0053* (2013.01); *A61K 9/1617* (2013.01); *A61K 9/1694* (2013.01); *B01J 13/08* (2013.01); *A23V 2002/00* (2013.01)

(58) Field of Classification Search
CPC .... A61K 9/145; A61K 9/0053; A61K 9/1617; A61K 9/1694; A61K 9/5015; A23L 33/12; A23L 33/115; B01J 13/08; A23V 2002/00
See application file for complete search history.

(56) References Cited

U.S. PATENT DOCUMENTS

| | | | |
|---|---|---|---|
| 8,663,692 B1 | 3/2014 | Mueller et al. | |
| 10,166,187 B2 * | 1/2019 | Diorio | A61K 9/1694 |
| 11,324,699 B2 * | 5/2022 | Diorio | A61K 31/045 |
| 2003/0015713 A1 | 1/2003 | Yoo | |

| | | | |
|---|---|---|---|
| 2005/0123615 A1 | 6/2005 | Ray et al. | |
| 2013/0017239 A1 | 1/2013 | Petit et al. | |
| 2015/0313844 A1 | 11/2015 | Tran et al. | |

FOREIGN PATENT DOCUMENTS

| | | |
|---|---|---|
| CL | 199800927 | 4/1998 |
| CL | 200000084 | 9/2000 |
| CL | 200600106 | 1/2006 |
| CL | 200600947 | 4/2006 |
| EP | 1637130 A1 | 6/2004 |
| GB | 2324701 B | 5/2001 |
| WO | 00/41682 A1 | 7/2000 |
| WO | 2003039521 A1 | 5/2003 |
| WO | 2019171009 A1 | 12/2019 |

OTHER PUBLICATIONS

Guimaraes-Inacio et al., Evaluation of the Oxidative Stability of Chia Oil-Loaded Microparticles by Thermal, Spectroscopic and Chemometric Methods, 498-506, 87; LWT- Food Science and Technology, 2018.

Search Report issued in GB1716419.5, Jun. 25, 2018.

Wolska et al., "Technology of Stable, Prolonged-Release Eye-Drops Containing Cyclosporine A, distributed between Lipid Matrix and Surface of the Solid Lipid Microspheres (SLM)", international Journal of Pharmaceutics, vol. 441, No. 1-2, pp. 449-457, 2013.

Veiga de Lara Gomes et al., "Characterization and Shelf life of beta-Carotene Loaded Solid Lipid Micropartcles Produced with Stearic Acid and Sunflower Oil" Arch. Biol. Technol., pp. 663-671, 2013.

Yang et al., "Encapsulation of Fish Oil into Hallow Solid Lipid Micro- and Nanoparticles using Carbon Dioxide", vol. 231, pp. 105-113, 2017.

Jaspart et al., "Solid Lipid Microparticles: Formulation, Preparation, Characterisation, Drug Release and Applicaitons", Expert Opinion on Drug Delivery, Information Healthcare, vol. 2 No. 1, pp. 75-87, 2005.

Vithani et al., "Sustained Release Solid Lipid Martrices Processed by Hot-Melt Extrusion (HME)", Colloids and Surfaces. B, Biointerfaces, Elsevier, vol. 110, pp. 403-410, 2013.

Gavini et al., "Solid Lipid Microparticles (SLM) Containing Juniper Oil as Anti-Acne Topical Carriers: Preliminary Studies", Pharmaceutical Development and Technology, 10:479-487, 2005.

International Search Report issued in PCT/GB2018/052855, Dec. 19, 2018.

International Preliminary Report of Patentability issued in PCT/GB2018/052855 on Apr. 20, 2020.

Chilean Search Report for Chilean Patent Application No. 202000918, mailed Apr. 14, 2021.

* cited by examiner

*Primary Examiner* — Snigdha Maewall

(74) *Attorney, Agent, or Firm* — ArentFox Schiff LLP

(57) ABSTRACT

The present invention relates to a solid composition which contains a mixture of liquid oil and solid lipid. The solid lipid acts as a solid carrier vehicle for the oil thereby permitting oils to be provided, at relatively high loading, in solid form.

31 Claims, 17 Drawing Sheets

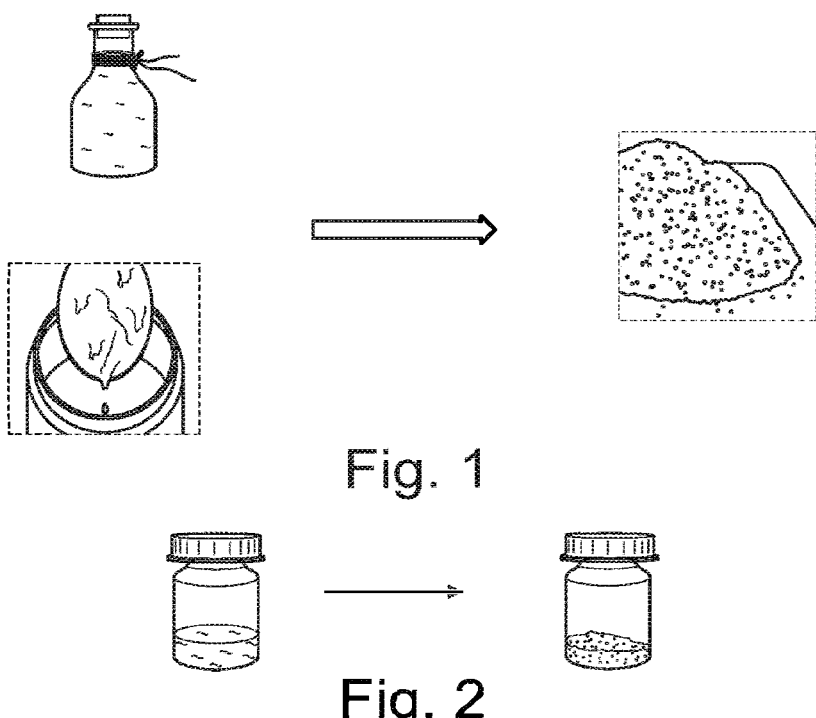

Fig. 1

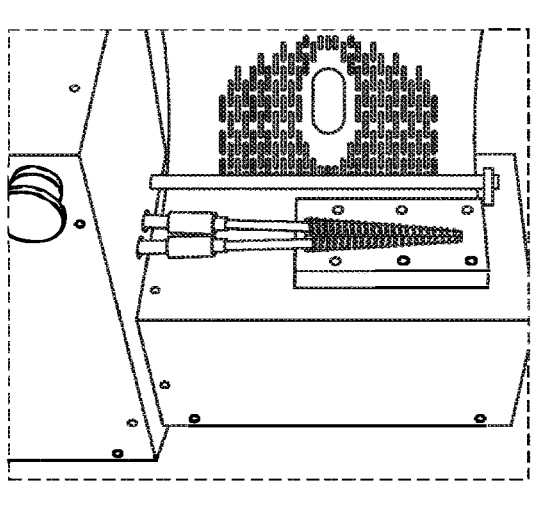

Fig. 2

| Technical Specifications | |
|---|---|
| Drive | |
| Motor power | 400 W |
| Speed range | 1....360 min $^{-1}$ |
| Max.torque | 5 Nm per screw |
| Control mode | Constant Speed Constant Torque |
| Power supply | 230 V ±10%, 50/60Hz 115 V ±10%, 60 Hz |
| HAAKE Force Feeder | |
| Max. Speed | 30 min $^{-1}$ |
| Material | Stainless steel 1.4122 Cr coated |
| Power supply | 230 V ±10%, 50/60Hz 115 V ±10%, 60 Hz |
| Extruder | |
| Design | Conical co-/counter rotating |
| Temperature | 300 °C |
| Heating time (80°-240°C) | < 10 Minutes |
| Barrel & Screws | High performance plastic mold steel (M340) |
| Cooling | Forced Convection |
| Pressure | up to 200 bar |
| Volume | 7 ml |
| Bypass | Manual valve |
| Feeding | Manual feeding Force feeder (optional) |

Fig. 3

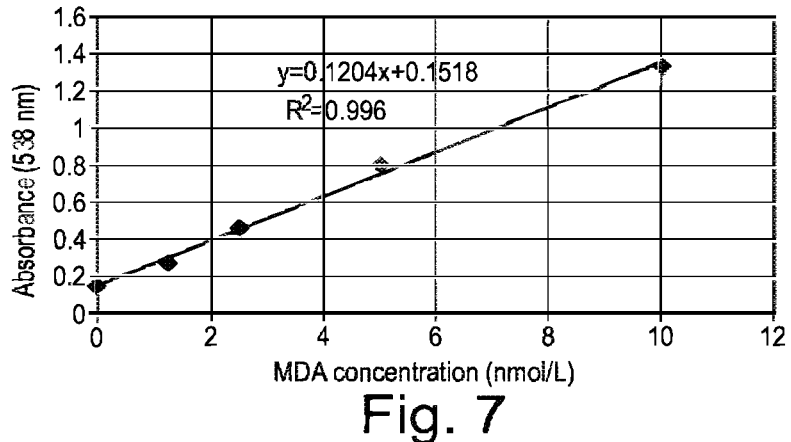
Fig. 7
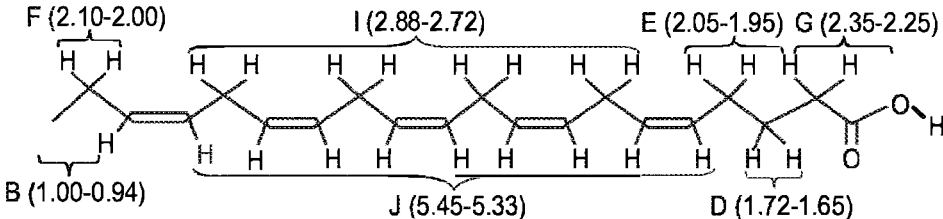
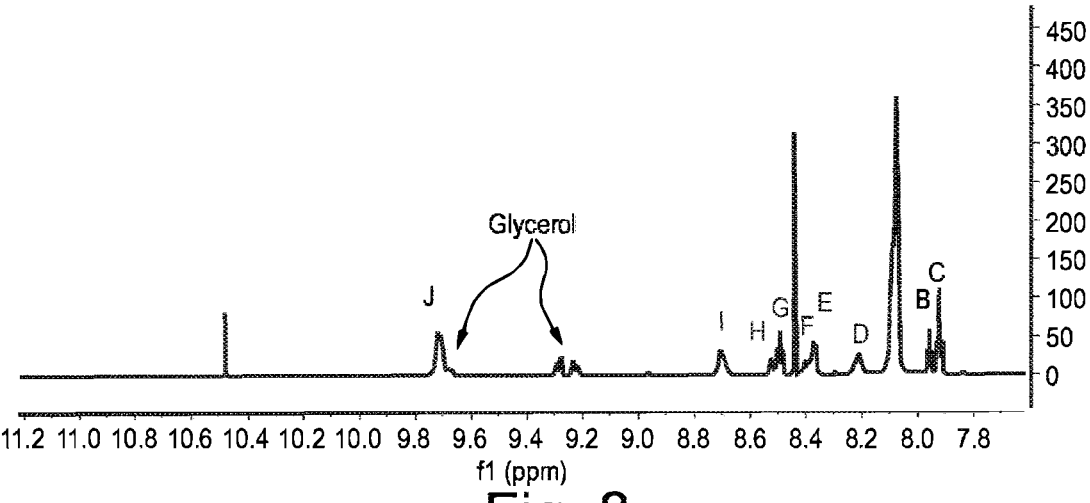
Fig. 8

R=unsaturated chain of aldehydes

Forcibly degraded fish oil

Pure fish oil

No aldehydes 11.4 11.2 11.0 10.8 10.6 10.4 10.2 10.0 9.8 9.6 9.4 9.2 9.0 8.8 8.6 8.4 8.2 8.0 7.8 f1 (ppm)

Fish oil

Glycerol

Forcibly degraded fish oil 9   8   7   6   5   4   3   2   1   0 f1 (ppm)

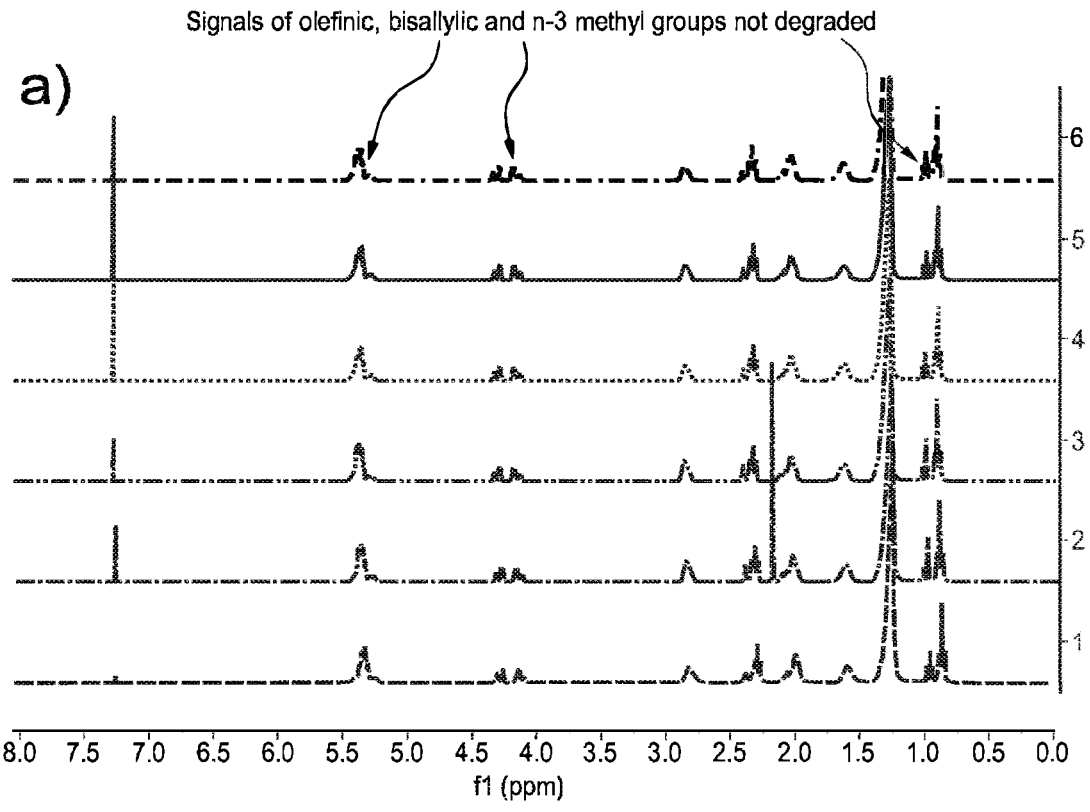
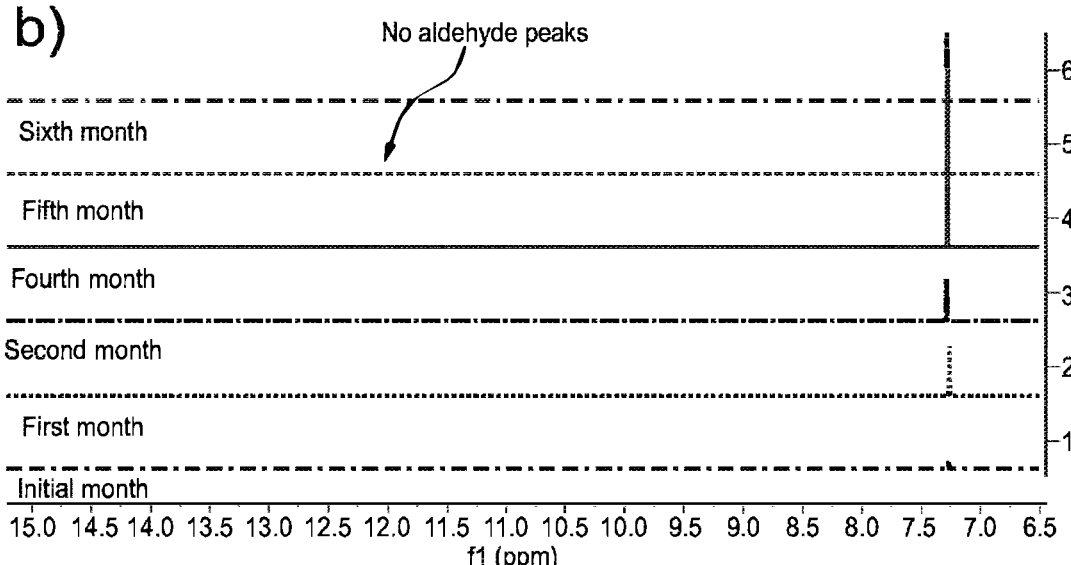
Fig. 13

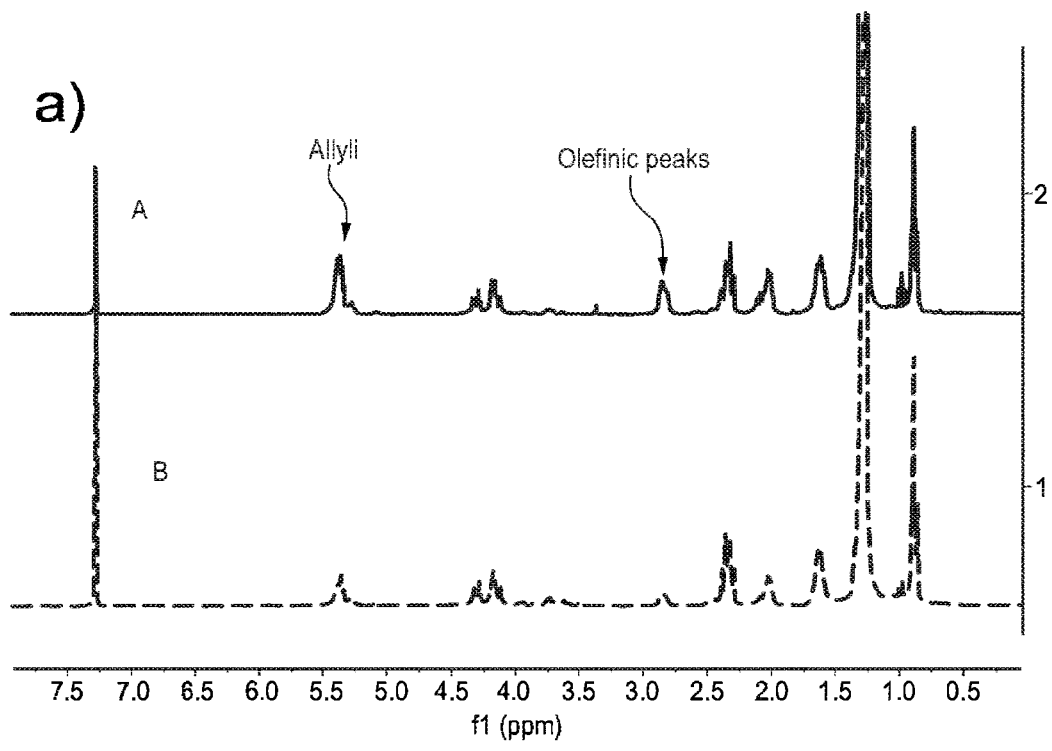
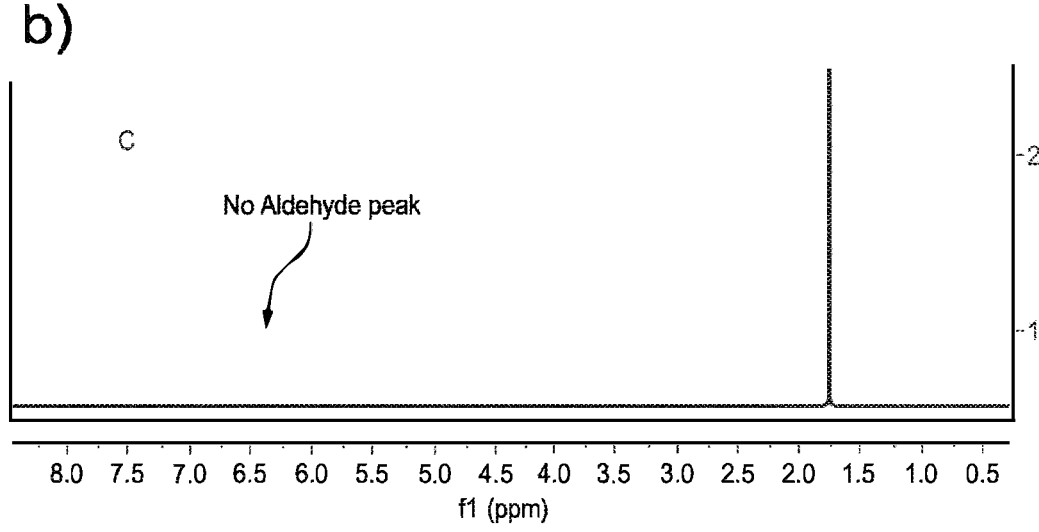
Fig. 16 a) X-ray diffraction:
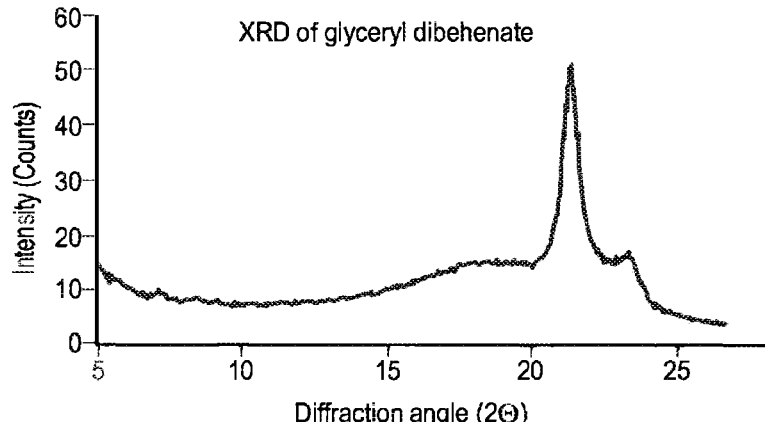
b)
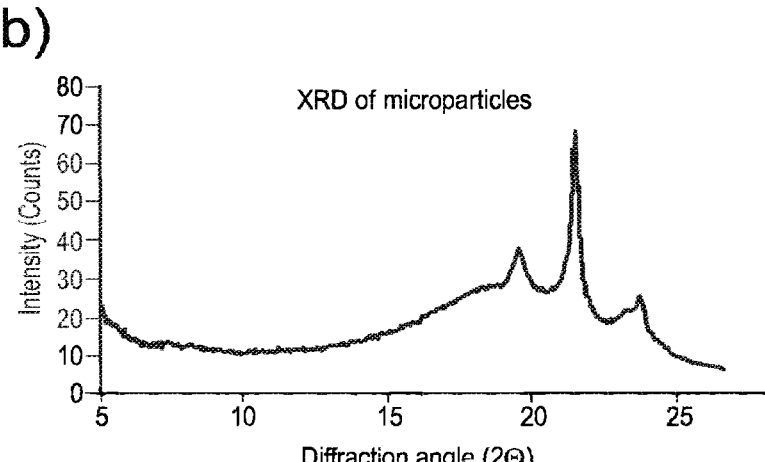
c)
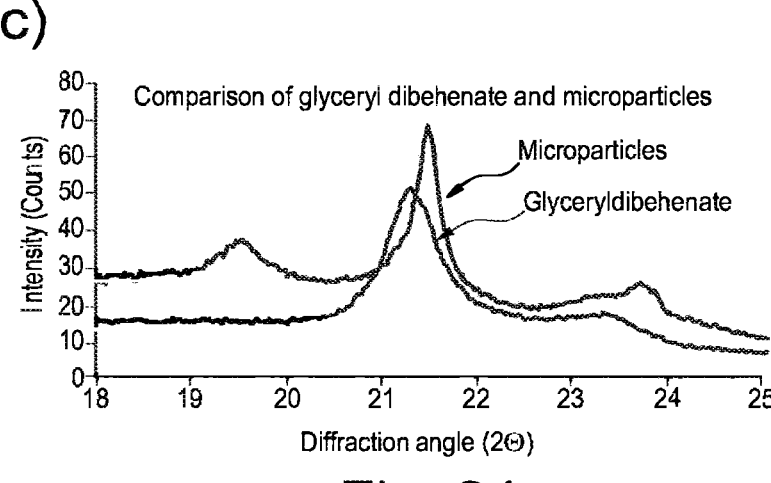
Fig. 24

Actual Test Solution A = 0.886-0.053      Actual Test Solution B = 1.092-0.156-0.096

= 0.833                                 = 0.801

Result = [25 * (1.2$A_s$ – $A_B$)]/m

*P- Anisidine* value (AV) = 6.81

**Standard range for *P-anisidine value* (AV) = 20**

SOLID COMPOSITION

CROSS-REFERENCE TO RELATED APPLICATIONS

This U.S. application is a continuation of U.S. application Ser. No. 16/754,061 filed Apr. 6, 2020, which is a U.S. national stage entry under 35. U.S.C. § 371 of PCT/GB2018/052855, filed Oct. 5, 2018, which claims the benefit of GB Application 1716419.5, filed Oct. 6, 2017. Each of the above-described applications is hereby incorporated herein by reference in their entirety.

INTRODUCTION

The present invention relates to a solid composition, in particular to a solid composition comprising an oil, such as an organic oil. The invention also relates to methods of preparing such solid compositions, methods of stabilising oils, and uses of the solid compositions.

BACKGROUND

Many products—including, for instance, pharmaceuticals, nutraceuticals, food supplements, cosmetics, agricultural products, pesticides—comprise liquid oils, many of which oils contain bioactive components. Such liquid oils may include marine oils (McLennan and Abeywardena 2005; Weitz et al., 2010), vegetable oils (Rubilar et al., 2012) and even essential oils (Beirao da Costa et al., 2013). Notable examples include flax seed oil, omega3 oils, fish oils, evening primrose oil, borage oil, castor oil, avocado oil, neem seed oil, olive oil, and rapeseed oil etc.

Since all oils tend to be liquids (of varying viscosities), at standard ambient temperature and pressure (SATP), they inherit problems associated with their handling, transportation, and storage stability. Some oils, such as fish oil and castor oil, are unpleasant in taste and odour and, as such, may render certain products, such as pharmaceuticals, somewhat unpalatable to consumers and/or patients—as a consequence compliance with important drug regimens may be compromised. Further problems arising from liquid oils include non-uniformity of dose, which is a particular problem in pharmaceuticals and nutraceutical products. Yet another problem is their chemical instability and oxidative deterioration.

Spray drying (Bao et al., 2011; Polavarapu et al., 2011) and coacervation (Leimann et al., 2009; Xiao et al., 2014) are perhaps the most commonly used techniques to encapsulate various oils in the food industry (Wan et al., 2011; Wang et al., 2011; Aghbashlo et al., 2012; Huang et al., 2014). Starch and its derivatives, e.g., maltodextrin, (Liu et al 2001) β-cyclodextrin, (Bhandari et al., 1999; Partanen et al., 2001) and gum (Kim and Moore, 1996; Beristain et al., 2001), gelatin, casein, cellulosic and synthetic (for example, nylon, polyethylene, and polyester) have been used as wall material for encapsulation of oils by spray drying. As spray drying involves an aqueous feed, the relevant polymer(s) must be sufficiently soluble in water for this process to be viable. These processes usually yield large particles with relatively low oil payloads (normally less than 30%) and high levels of surface oil. Such particles can be undesirable.

Other techniques, such as freeze-drying of oils (Heinzelmann et al., 2000), allows the relatively high temperatures of spray-drying to be avoided, as freeze-drying is inherently a low temperature process.

Recently, extrusion techniques have been used to encapsulate some vegetable and essential oils, including olive, clove, thyme, and cinnamon oils, for the food and pesticide industries (Sun-Waterhouse et al., 2011; Soliman et al., 2013). It has been used almost exclusively for microencapsulation of oils in a carbohydrate matrix (Yilmaz, et al., 2001). In the melt injection process, the core material is dispersed in molten carbohydrate, and is then pressed through one or more dies (orifices) into a bath of cold, dehydrating liquid such as isopropanol and liquid nitrogen. However, alternative processes are desirable, especially as carbohydrates can be unstable at high temperatures.

Recently, fish oils have been the subject of increased interest due to them being a rich source of omega-3 fatty acids, which have potential health benefits (Tur, J. A, et al., 2012) such as prevention of cardiovascular disease and reduced risk of chronic disease, mental disorders or poor infant development. Fish oil contain eicosapentaenoic acid (EPA, 20:5) and docosahexaenoic acid (DHA, 22:6) omega-3 fatty acids which reported possess the highest bioactivity (Gulotta, A, et al., 2014). However, these and other components of marine oils are prone to oxidative deterioration which inter alia can lead to the development of undesirable rancid odour and taste on storage. Literature studies suggest that fish oils are sensitive to oxygen, light and temperature, which are all important factors in their deterioration and unpleasant smell. It is therefore desirable to overcome such problems.

An object of the present invention is to solve problem(s) inherent in the prior art. Another object is to solve one or more of the aforementioned problems. Another object is to facilitate new uses for oil-containing products.

SUMMARY OF THE INVENTION

According to a first aspect of the present invention there is provided a solid composition comprising an oil component and a lipid component.

According to a further aspect of the present invention there is provided a method of preparing a solid composition, comprising mixing together an oil component and a lipid component to form an oil-lipid mixture, and optionally further processing the oil-lipid mixture.

According to a further aspect of the present invention there is provided a solid composition obtained by, obtainable by, or directly obtained by a method of preparing a solid composition as defined herein.

According to a further aspect of the present invention there is provided an oil-containing product comprising a solid composition as defined herein.

According to a further aspect of the present invention there is provided a method of preparing an oil-containing product, the method comprising:
a) incorporating a solid composition as defined herein within a product; or
b) transforming the solid composition into the oil-containing product after production of the solid composition; or
c) producing the oil-containing product during (or as part of) a method of preparing a solid composition as defined herein.

According to a further aspect of the present invention there is provided an oil-containing product obtained by, obtainable by, or directly obtained by a method of preparing an oil-containing product as defined herein.

In a particular embodiment, the oil-containing product is an oral dosage form, suitably a pharmaceutical, nutraceutical, or food supplement, oral dosage form. In a particular embodiment, the oil-containing product is a personal care product, for instance, a perfume.

According to a further aspect of the present invention there is provided a nutraceutical/pharmaceutical composition (suitably an orally-administrable nutraceutical/pharmaceutical composition or a composition for preparing an orally administrable nutraceutical/pharmaceutical composition, e.g. through dissolution in water) comprising an oil component and a lipid component (or a solid composition as defined herein). In an embodiment, the oil component is or comprises a nutraceutical/pharmaceutical agent. In an embodiment, the oil component is a marine oil, suitably a fish oil. Alternatively, the nutraceutical/pharmaceutical composition may comprise a nutraceutical/pharmaceutical agent in addition to the oil component. Suitably such a nutraceutical/pharmaceutical agent is hydrophobic and soluble in the oil component.

According to a further aspect of the present invention there is provided a method of encapsulating an oil component, the method comprising incorporating the oil component into a solid composition as defined herein, suitably via a method of preparing a solid composition as defined herein.

According to a further aspect of the present invention there is provided a method of stabilising an oil component, the method comprising incorporating the oil component into a solid composition as defined herein, suitably via a method of preparing a solid composition as defined herein.

According to a further aspect of the present invention there is provided a solid composition (as defined herein) for use as a medicament, for use in therapy, for use in surgery, or for use in diagnosis and/or prognosis.

According to a further aspect of the present invention there is provided a use of a solid composition (as defined herein) in the manufacture of a medicament for use in therapy.

Any features, including optional, suitable, and preferred features, described in relation to any particular aspect of the invention may also be features, including optional, suitable and preferred features, of any other aspect of the present invention.

BRIEF DESCRIPTION OF THE DRAWINGS

For a better understanding of the invention, and to show how embodiments of the same are put into effect, reference is now made, by way of example, to the following diagrammatic drawings, in which:

FIG. 1 shows pictorially two different types of oily substance and the powdery product into which they may be converted by implementing the present invention.

FIG. 2 shows pictures of fish oil (left), prior to transformation, and fish oil microparticles containing 50% oil, (right) following transformation.

FIG. 3 shows a twin-screw hot melt extruder alongside its technical specifications.

FIG. 7 shows a calibration graph for MDA (0-10 nmol/mL).

FIG. 8 shows a proton NMR spectra, and spectral assignments, of fish oil showing both EPA and DHA peaks.

FIG. 13 shows several proton NMR spectra of fish oil microparticles taken over a six month period, both (a) full; and (b) expanded to show any aldehyde peaks.

FIG. 16 shows 50:50 ratio fish oil microparticles products from both the techniques looks similar.

FIG. 24 shows XRD traces for pure a) bulk glyceryl dibehenate b) microparticles c) comparison of microparticles and bulk glyceryl dibehenate.

DETAILED DESCRIPTION OF THE INVENTION

Definitions

Figure 4:
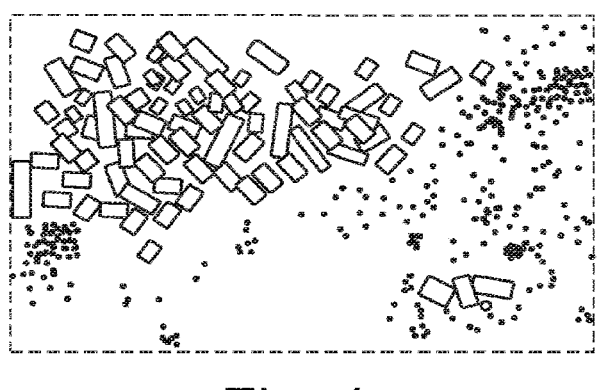
FIG. 4 shows fish oil microparticles containing 50% oil, produced using hot melt extrusion.

Unless otherwise stated, the following terms used in the specification and claims have the following meanings set out below.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

For the avoidance of doubt, it is hereby stated that the information disclosed earlier in this specification under the heading "Background" is relevant to the invention and is to be read as part of the disclosure of the invention.

Unless stated otherwise, any reference herein to an "average" value is intended to relate to the mean value.

Where a composition is said to comprise a plurality of stipulated ingredients (optionally in stipulated amounts of concentrations), said composition may optionally include additional ingredients other than those stipulated. However, in certain embodiments, a composition said to comprise a plurality of stipulated ingredients may in fact consist essentially of or consist of all the stipulated ingredients.

Herein, where a composition is said to "consists essentially of" a particular component, said composition suitably comprises at least 70 wt % of said component, suitably at least 90 wt % thereof, suitably at least 95 wt % thereof, most suitably at least 99 wt % thereof. Suitably, a composition said to "consist essentially of" a particular component consists of said component save for one or more trace impurities.

Where the quantity or concentration of a particular component of a given composition is specified as a weight percentage (wt % or % w/w), said weight percentage refers to the percentage of said component by weight relative to the total weight of the composition as a whole. It will be understood by those skilled in the art that the sum of weight percentages of all components of a composition will total 100 wt %. However, where not all components are listed (e.g. where compositions are said to "comprise" one or more particular components), the weight percentage balance may optionally be made up to 100 wt % by unspecified ingredients (e.g. a diluent, such as water, or other non-essentially but suitable additives).

Herein, unless stated otherwise, the term "parts" (e.g. parts by weight, pbw) when used in relation to multiple ingredients/components, refers to relative ratios between said multiple ingredients/components. Expressing molar or weight ratios of two, three or more components gives rise to the same effect (e.g. a molar ratio of x, y, and z is $x_1:y_1:z_1$ respectively, or a range $x_1-x_2:y_1-y_2:z_1-z_2$). Though in many embodiments the amounts of individual components within a composition may be given as a "wt %" value, in alternative embodiments any or all such wt % values may be converted to parts by weight (or relative ratios) to define a multi-component composition. This is so because the relative ratios between components is often more important than the absolute concentrations thereof in the liquid pharmaceutical compositions of the invention. Where a composition comprising multiple ingredients is described in terms of parts by weight alone (i.e. to indicate only relative ratios of ingredients), it is not necessary to stipulate the absolute amounts or concentrations of said ingredients (whether in toto or individually) because the advantages of the invention can stem from the relative ratios of the respective ingredients rather than their absolute quantities or concentrations. However, in certain embodiments, such compositions consists essentially of or consist of the stipulated ingredients and a diluents (e.g. water).

The term "mole percent" (i.e. mol %) is well understood by those skilled in the art, and the mol % of a particular constituent means the amount of the particular constituent (expressed in moles) divided by the total amount of all constituents (including the particular constituent) converted into a percentage (i.e. by multiplying by 100). The concept of mol % is directly related to mole fraction.

The term "substantially free", when used in relation to a given component of a composition (e.g. "a liquid pharmaceutical composition substantially free of compound X"), refers to a composition to which essentially none of said component has been added. When a composition is "substantially free" of a given component, said composition suitably comprises no more than 0.001 wt % of said component, suitably no more than 0.0001 wt % of said component, suitably no more than 0.00001 wt %, suitably no more than 0.000001 wt %, suitably no more than 0.0000001 wt % thereof, most suitably no more than 0.0001 parts per billion (by weight).

The term "entirely free", when used in relation to a given component of a composition (e.g. "a liquid pharmaceutical composition entirely free of compound X"), refers to a composition containing none of said component.

Suitably, unless stated otherwise, where reference is made to a parameter (e.g. pH, pKa, etc.) or state of a material (e.g. liquid, gas, etc.) which may depend on pressure and/or temperature, suitably in the absence of further clarification such a reference refers to said parameter at standard ambient temperature and pressure (SATP).

Standard ambient temperature and pressure (SATP) is a temperature of 298.15 K (25° C., 77° F.) and an absolute pressure of 100 kPa (14.504 psi, 0.987 atm).

Though the term "fatty acid", as used herein, may refer to a free acid of a fatty acid (i.e. non-esterified fatty acid, NEFA), unless otherwise specified the term fatty acid suitably encompasses both non-esterified fatty acids and fatty acid esters (typically glycerides such as monoglycerides, diglycerides, or triglycerides).

Herein, unless stated otherwise, all chemical nomenclature may be defined in accordance with IUPAC definitions.

General Methodology and Advantages of the Invention

The present invention allows oils, such as organic oils and mineral oils which generally adopt a liquid form at SATP, to be converted into a solid form (at SATP) using solid carrier materials (e.g. lipids) that are highly compatible with the oils.

Contrary to expectations, that mixing lipids with oils would lead merely to a new liquid oil just with a higher lipid content and a modified viscosity (or that equivalent oil-lipid mixtures would yield oil-in-water droplets or emulsions in aqueous media), the inventors have found that lipids are excellent solid carriers for oils, even allowing for very high loadings of oil without undue clumping or oiliness—in fact free-flowing particulate solids can be formed using this new technology.

Such solid forms of the oil have a number of advantages over the original liquid forms thereof. Such advantages include ease of handling (either as a consumer or as a manufacture incorporating such oils into other products), transportation, and storage stability (especially with respect to chemical, oxidative, and photolytic degradation). As will become apparent, such solid forms may also serve to mask unpalatable tastes and/or odours for certain oils (e.g. fish oils). Solid forms of the oils, according to the invention, also tend to have a more uniform and consistent composition across a bulk mass compared to the original liquid oil. Moreover, many of the solid compositions of the invention have less surface oil, thereby allowing for the production of smaller particles, such as microparticles. Moreover, the prominence of hydrophobic materials in the solid compositions of the invention allows such solid compositions to serve as carriers for other hydrophobic compounds, which may be of use—be these hydrophobic drugs, hydrophobic nutraceuticals, hydrophobic food supplements, etc. For instance, the hydrophobic compounds may be dissolved or mixed with the oil component prior to its combination with a lipid component to form the solid composition of the invention.

Since lipids are chemically inert to oils and components thereof, stability of the oils is not compromised—in fact, surprisingly the inventors have found that the present invention can be used to increase the stability of the oils and/or components thereof (e.g. key bioactive components, such as omega-3s). Therefore, advantage properties of the oils, or components thereof, can be preserved through their incorporation into solid compositions of the invention.

Lipids do not compromise physical properties, such as combustibility, of the oils and thus solid compositions of the invention can still be burnt to obtain certain benefits from the oils (e.g. burning of essential oils) whilst obtaining the benefits of the invention.

Lipids are generally safe for human consumption, so again this methodology allows benefits of the oils to be realised through ingestion whilst simultaneously achieving the aforementioned benefits of the invention. It is, for example, easier to produce oil-containing orally-administered pharmaceuticals, nutraceuticals, and/or food supplements using the solid compositions of the invention rather than the liquid oils. For instance, bioactive oil-containing solid tablets become a viable alternative to oil-containing capsules when adopting the present invention, since oil-containing solid compositions of the invention can be granulated and/or compressed to form viable solid tablets.

A wide-range of new products also become viable following then advent of the invention. For example, oil-loaded microparticles can be used as powder as such, as effervescent powders, as encapsulated in hard capsules, as compressed tablets/pellets, or incorporated into food products.

Various methodologies may be used to prepare solid compositions of the invention, as a skilled process development chemist or formulation development scientist will appreciate. Two particular methods are exemplified herein, one of which involves the formation of the solid composition within an aqueous medium and subsequent extraction therefrom, whilst another involves hot-melt extrusion. Such methods are discussed in more detail below.

Solid Composition

The present invention provides a solid composition. The solid composition comprises an oil component, or oily substance. The solid composition suitably comprises a solid carrier, suitably a solid carrier that encapsulates or co-mixes with the oil component. The solid carrier suitably is or comprises a lipid component. Suitably, references herein to a lipid component may, where appropriate in context, be substituted by a solid carrier in general.

Suitably, the solid composition comprises an oil component (or oily substance) and a lipid component.

The oil component may comprise a single oil. The oil component may comprise a plurality of oils. The oil component may comprise a single oil that constitutes at least 70 wt % of the total weight of the oil component, suitably at least 80 wt %, suitably at least 90 wt %, suitably at least 95 wt %, suitably at least 99 wt %.

The lipid component may comprise a single lipid. The lipid component may comprise a plurality of lipids. The lipid component may comprise a single lipid that constitutes at least 70 wt % of the total weight of the lipid component, suitably at least 80 wt %, suitably at least 90 wt %, suitably at least 95 wt %, suitably at least 99 wt %.

Unless otherwise specified or inappropriate in a given context, references herein to a single oil or a single lipid may respectively apply to a plurality of oils or a plurality of lipids (including quantities, amounts, etc.).

The oil component is suitably a liquid at SATP, whereas the lipid component is suitably a solid at SATP. The solid composition comprising both the oil component and lipid component is suitably a solid at SATP. The solid composition may however melt, and at standard pressure (e.g. 1 atm) may be in a liquid/melted state at 35° C., 40° C., 50° C., 60° C., 70° C., 80° C., and/or 100° C. Suitably the solid composition has a melting point at or above 35° C., suitably at or above 50° C., suitably at or above 60° C., suitably at or above 70° C. Suitably the solid composition has a melting point at or below 100° C., suitably at or below 90° C., suitably at or below 80° C., suitably at or below 70° C. Suitably the solid composition has a melting point in the region of 40-90° C., suitably between 50-80° C. The melting point of the solid composition is suitably influenced by the melting point of the lipid component (or predominant lipid therein) incorporated into the solid composition.

The solid composition may be in a particulate form. The solid composition may be a powder, suitably a free-flowing powder. Suitably the solid composition comprises particles having an average particle size greater than or equal to 5 μm, suitably greater than or equal to 10 μm, suitably greater than or equal to 20 μm, suitably greater than or equal to 50 μm, suitably greater than or equal to 70 μm, suitably greater than or equal to 100 μm, suitably greater than or equal to 150 μm suitably greater than or equal to 200 μm. Suitably the solid composition comprises particles having an average particle size less than or equal to 2000 μm, suitably less than or equal to 1000 μm, suitably less than or equal to 800 μm, suitably less than or equal to 700 μm, suitably less than or equal to 600 μm, suitably less than or equal to 500 μm, suitably less than or equal to 400 μm. The solid composition may be microparticulate (i.e. comprising or consisting of microparticles), suitably having an average particle size of between 1 and 1000 μm, more suitably between 10 and 500 μm, more suitably between 20 and 200 μm. In a particular embodiment, the solid composition comprises particles having an average particle size between 20 and 500 μm. In a particular embodiment, the solid composition comprises particles having an average size between 70 and 300 μm. Average particle size in particulate forms of the solid composition may be influenced by features of the method of preparing the solid composition. Alternatively, particle size may be adjusted after production of the solid composition, for instance, by grinding, milling, crushing, sieving, and/or any combination thereof.

Solid compositions with very small particles sizes (e.g. <10 μm) can suffer from a degree of stickiness or oiliness (often due to greater quantities of surface oil and lower levels of oil encapsulation). Such particles may typically be formed using emulsification techniques (e.g. oil-in-water emulsions), which techniques can in themselves yield particles with lower levels of encapsulation, and lower overall particle yields. Notwithstanding such disadvantages, solid compositions having such particles sizes may be well suited to topical applications—for instance such solid compositions may be incorporated within topical creams or ointments. Though the present invention as defined herein may be deployed to form topical compositions, most suitably the present invention is applicable to the formation or orally-administrable dosage forms, such as orally-administrable nutraceuticals/pharmaceuticals. In such embodiments, the ingredients of the solid composition must be nutraceutically and/or pharmaceutically acceptable—e.g. suitable non-toxic for human consumption. Solid compositions applicable in orally-administrable dosage forms suitably have larger average particle sizes (e.g. ≥10 μm).

The solid composition may be in a block form, for instance as a monolithic block or a filament. Suitably such a block form may be fragmented, suitably to form a particulate form of the solid composition. However, in some applications it may be desirable to use the solid composition in a block form, for example, as a filament in 3D printing (e.g. fused filament fabrication, FFF, printing, also known as FDM—fused deposition modelling).

In some embodiments, the solid composition is a compressed particulate form—i.e. the solid composition is in a particulate form, as per above, but the particles are compressed together, optionally with a binding agent. In some embodiments, the solid composition is a granulated particulate form—i.e. the solid composition is in a particulate form, as per above, but the particles are transformed into granules (incorporating a plurality of said particles), optionally including one or more additional excipients, for instance, a binding agent.

The solid composition suitably comprises an oil component and a lipid component in a respective weight ratio of between 1:99 (oil/lipid) and 99:1, suitably between 5:95 and 70:30, more suitably between 10:90 and 60:40, suitably between 20:80 and 55:45, suitably between 30:70 and 52:48. In a particular embodiment, the solid composition comprises an oil component and a lipid component in a respective weight ratio of between 15:85 and 60:40 Most suitably, the oil component is present at a weight ratio with the lipid component no more than 60:40, suitably no more than 55:45, suitably no more than 50:50. Suitably, the oil component is present at a weight ratio with the lipid component of at least 20:80, suitably at least 30:70, suitably at least 35:65.

Suitably the lipid component constitutes at least 10 wt % of the total weight of the solid composition, suitably at least 20 wt %, suitably at least 30 wt %, suitably at least 40 wt %, suitably at least 50 wt %, suitably at least 60 wt %. Suitably the lipid component constitutes at most 95 wt % of the total weight of the solid composition, suitably at most 90 wt %, suitably at most 80 wt %, suitably at most 70 wt %, suitably at most 60 wt %, suitably at most 50 wt %.

Suitably the oil component constitutes at least 1 wt % of the total weight of the solid composition, suitably at least 5 wt %, suitably at least 10 wt %, suitably at least 20 wt %, suitably at least 30 wt %, suitably at least 40 wt %. Suitably the oil component constitutes at most 60 wt % of the total weight of the solid composition, suitably at most 55 wt %, suitably at most 50 wt %, suitably at most 40 wt %, suitably at most 30 wt %, suitably at most 20 wt %.

Suitably the combination of both the oil component and lipid component constitutes at least 20 wt % of the total weight of the solid composition, suitably at least 30 wt %, suitably at least 40 wt %, suitably at least 50 wt %, suitably at least 70 wt %, suitably at least 80 wt %, suitably at least 90 wt %, suitably at least 95 wt %, suitably at least 99 wt %. In some embodiments, the solid composition consists essentially of, or consists of, the oil component and the lipid component.

Suitably, the solid composition of the invention comprise relatively little surface oil, suitably less than 30 wt % surface oil (less than 30 wt % of the total oil component of the solid composition is present at the surface), suitably less than 20 wt % surface oil, suitably less than 15 wt %.

Suitably, particles of the solid composition of the invention comprise relatively little surface oil, suitably less than 30 wt % surface oil, suitably less than 20 wt % surface oil, suitably less than 15 wt % surface oil, I. Low surface-oil affords more free-flowing particles since surface oil can cause clumping and/or stickiness.

Surface oil was assessed by taking 1.5 gm of microparticles in a glass jar with a lid and seven millilitres of hexane was added to it. The jar which was shaken by hand for the extraction of free oil, for 1 min, at room temperature. The mixture was filtered through a Whatman filter paper no. 1 and the filtered powder collected on the filter paper. Then, the solvent was collected in a clean flask and left to evaporate in at room temperature and after drying heated at 60° C., until constant weight is obtained. The non-encapsulated oil (surface oil) was determined by mass difference between the initial clean flask and that containing the extracted oil residue. Microparticles prepared without loaded oil served as control.

As such, surface oil is measurable by extracting the surface oil from a pre-determined amount (e.g. a known weight) of solid composition (i.e. a sample of the solid composition), and determining the amount (e.g. weight, suitably dried weight) of the extracted surface oil. A percentage (e.g. wt %) surface oil may then be calculated by dividing the amount/weight of extracted surface oil by the pre-determined amount/weight of the solid composition from which the surface oil was extracted. The surface oil is suitably extracted from the solid composition by selectively dissolving the surface oil into a surface oil solvent, for instance, a non-polar solvent such as hexane, to produce a surface oil solution. Such dissolving is suitably performed by mixing the solid composition (or particles thereof) with the surface oil solvent. Suitably the lipid component and non-surface oil (i.e. oil encapsulated within a lipid matrix) is (substantially) not dissolved by the surface oil solvent. Such selective dissolution of the surface oil may be achieved by judicious solvent selection and/or mixing times (i.e. when the solid composition is in contact with the solid composition). Suitably mixing time (suitably with agitation) is less than or equal to 5 mins, suitably less than or equal to 2 mins, suitably less than or equal to 1 min. The amount of extracted surface oil is suitably measured after (substantially) evaporating the surface oil solvent from the surface oil solution. Suitably, evaporation is performed to leave merely the surface oil extract, which can be weighed.

Suitably, solid composition comprises the oil component (substantially) encapsulated within a lipid matrix. Suitably, the oil component is dissolved or dispersed within the lipid matrix. Suitably, in particulate forms, the solid composition comprises particles, each of which comprises the oil component encapsulated and/or dissolved/dispersed within a solid hydrophobic lipid matrix.

Suitably the oil component, and/or particular compound(s) therein, exhibit enhanced storage stability within the solid compositions of the invention as compared to the same oil component alone. Suitably storage stability may be measured by any one or more of the methods defined herein, and storage conditions may be over a suitable time period and may optionally be under stressed conditions (e.g. elevated temperature, exposure to oxygen, exposure to light, etc.).

Suitably the oil component and lipid component, and relative ratios thereof, may be independently selected and tailored for an envisaged application.

Oil Component

The oil component suitably comprises at least one oil (i.e. one individual oil). The oil component may comprise only one oil. In an embodiment, the oil component is such that a single (individual) oil constitutes at least 70 wt % of the total weight of the oil component, suitably at least 80 wt %, suitably at least 90 wt %, suitably at least 95 wt %, suitably at least 99 wt %. The oil component may comprise a plurality of oils.

An individual "oil" is essentially a hydrophobic, lipophilic, viscous liquid (at SATP) which generally comprises a mixture of compounds, suitably predominantly ($\geq 50\%$, $\geq 60\%$, $\geq 70\%$, $\geq 80\%$, $\geq 90\%$, most suitably $\geq 95\%$) hydrophobic and lipophilic compound(s), suitably at least two or more of such compounds, suitably at least three or more such compounds, suitably at least four or more such compounds. Suitably all of the compound(s) present within any given oil are neutral (i.e. non-ionic and/or non-ionised).

The or each oil of the oil component suitably has a partition coefficient (octanol-Water partition coefficients, Log P) of at least 3, suitably at least 4, suitably at least 4.5, suitably at least 5, suitably at least 6. Suitably at least 70 wt % of the total weight of the or each oil comprises compounds which have a partition coefficient (octanol-Water partition coefficients, Log P) of at least 3, suitably at least 4, suitably at least 4.5, suitably at least 5, suitably at least 6, suitably at least 80 wt %, suitably at least 90 wt %, suitably at least 95 wt %.

An "oil" tends to have a high carbon and high hydrogen content and are typically flammable. An "oil" is suitably surface active.

The oil component suitably has a particular viscosity measurable by techniques well known in the art. Herein, unless stated otherwise, all viscosity quantities given herein are kinematic viscosities at SATP, which is determinable by obtaining a dynamic viscosity (suitably at SATP, suitably at shear rates ranging from 0.1 sec-1 to 100 sec-1 or taking a dynamic viscosity as an average in these shear rate ranges) and converting to a kinematic viscosity in accordance with the following equation:

$$v = \mu/\rho \tag{1}$$

where v is kinematic viscosity, $\mu$ is dynamic viscosity, and p is density of the overall fluid. Kinematic viscosities are expressed in centistokes (cSt), though SI units for kinematic viscosity are m²/s. Water at 20° C. has a kinematic viscosity of approximately $10^{-6}$ m²·s⁻¹ or 1 cSt.

Suitably, the oil component has a kinematic viscosity between 10 and 500 cSt at SATP, suitably between 20 and 250 cSt, suitably between 30 and 150 cSt, suitably between 40 and 100 cSt, suitably between 50 and 80 cSt at SATP.

Suitably, the oil component is orally-administrable. Suitably the oil component is ingestible (suitably safely so, in accordance with pharmaceutical, nutraceutical, and/or food supplement regulations). Suitably the oil component is a pharmaceutically and/or nutraceutically acceptable, suitably non-toxic at orally-administrable levels.

The oil component suitably comprises, consists essentially of, or consists of one or more oils selected from the group consisting of organic oils and mineral oils. Most suitably, the oil component comprises, consists essentially of, or consists of one or more organic oils.

Mineral oils are petroleum-derived oils, otherwise known as petrochemical oils.

Organic oils are generally derived from animal sources, plant sources, and other organisms—e.g. animal oils, vegetable oils, essential oils (which are generally from plants). Such organic oils are often produced through natural metabolic processes within such organisms. Where organic oils are used in the context of the present invention, suitably such organic oils exclude plant-derived essential oils.

Organic oils generally comprise a mixture of lipids, and may optionally further include one or more substances selected from the group consisting of proteins, waxes, and alkaloids. The mixture of lipids may comprise compounds in one or more compound classes selected from the group consisting of fatty acids, glycerolipids, sterol lipids, steroids, phospholipids, sphingolipids, glycerophospholipids, prenol lipids, saccharolipids, polyketides, and optionally esters of any of the aforementioned.

Organic oils suitable for use with the present invention include vegetable oils (usually rich in mono, di, and/or triglycerides) selected from the group consisting of:

Common vegetable oils: Coconut oil, Corn oil, Cottonseed oil, Olive oil, Palm oil, Peanut oil (Ground nut oil), Rapeseed oil (including Canola oil), Safflower oil, Sesame oil, Soybean oil, Sunflower oil;

Nut oils: Almond oil, Beech nut oil, Brazil nut oil, Cashew oil, Hazelnut oil, Macadamia oil, Mongongo nut oil, Pecan oil, Pine nut oil, Pistachio oil, Walnut oil;

Citrus oils: Grapefruit seed oil, Lemon oil, Orange oil,

Cucurbitaceae oils: Bitter gourd oil, Bottle gourd oil, Buffalo gourd oil, Butternut squash seed oil, Egusi seed oil, Pumpkin seed oil, Watermelon seed oil;

Food Supplement oils: Acai oil, Black seed oil, Blackcurrant seed oil, Borage seed oil, Evening primrose oil, Flaxseed oil;

Other Edible oils: Amaranth oil, Apricot oil, Apple seed oil, Argan oil, Avocado oil, Babassu oil, Ben oil, Borneo tallow nut oil, Cape chestnut oil, Carob pod oil (Algaroba oil) Cocoa butter, Cocklebur oil, Cohune oil, Coriander seed oil, Date seed oil, Dika oil, False flax oil, Grape seed oil, Hemp oil, Kapok seed oil, Kenaf seed oil, Lallemantia oil, Mafura oil, Marula oil, Meadowfoam seed oil, Mustard oil (pressed), Niger seed oil, Poppyseed oil, Nutmeg butter, Okra seed oil, Papaya seed oil, Perilla seed oil, Persimmon seed oil, Pequi oil, Pili nut oil, Pomegranate seed oil, Poppyseed oil, Pracaxi oil, Virgin pracaxi oil, Prune kernel oil, Quinoa oil, Ramtil oil, Rice bran oil, Royle oil, Shea nuts, Sacha inchi oil, Sapote oil, Seje oil, Shea butter, Taramira oil, Tea seed oil (Camellia oil), Thistle oil, Tigernut oil (or nut-sedge oil), Tobacco seed oil, Tomato seed oil, Wheat germ oil;

Multi-purpose oils: Castor oil, Coconut oil (copra oil), Colza oil, Corn oil, Cottonseed oil, False flax oil, Hemp oil, Mustard oil, Palm oil, Peanut oil, Radish oil,
Rapeseed oil, Ramtil oil, Rice bran oil, Safflower oil,
Salicornia oil, Soybean oil, Sunflower oil, Tigernut oil,
Tung oil;

Inedible oils: Copaiba, Jatropha oil, Jojoba oil, Milk bush,
Nahor oil, Paradise oil, Petroleum nut oil, Pongamia oil
(also known as Honge oil);

Drying oils: Dammar oil, Linseed oil, Poppyseed oil,
Stillingia oil, Tung oil, Vernonia oil; and Miscellaneous vegetable oils: Amur cork tree fruit oil,
Artichoke oil, Astrocaryum murumuru butter, Balanos oil, Bladderpod oil, Brucea javanica oil, Burdock
oil (Bur oil), Buriti oil, Candlenut oil (Kukui nut oil),
Carrot seed oil (pressed), Castor oil, Chaulmoogra oil,
Crambe oil, Croton oil (tiglium oil), Cuphea oil, Cup-
uacu butter, Honesty oil, Illipe butter, Jojoba oil,
Mango oil, Mowrah butter, Neem oil, Ojon oil, Passion
fruit oil, Rose hip seed oil, Rubber seed oil, Sea
buckthorn oil, Sea rocket seed oil, Snowball seed oil
(Viburnum oil), Tall oil, Tamanu or foraha oil, Tonka
bean oil (Cumaru oil), Tucumã butter, Ucuhuba seed oil.

Organic oils suitable for use with the present invention
include essential oils selected from the group consisting of:
Agar oil or oodh, Ajwain oil, Angelica root oil, Anise oil,
Asafoetida oil, Balsam of Peru, Basil oil, Bay oil, Bergamot
oil, Black Pepper oil, Buchu oil, Birch oil, Camphor oil,
Cannabis flower essential oil, Calamodin oil or Calamansi
Essential Oil, Caraway oil, Cardamom seed oil, Carrot seed
oil, Cedar oil (or Cedarwood oil), Chamomile oil, Calamus
oil, Cinnamon oil, Citron oil, Citronella oil, Clary Sage oil,
Coconut Oil, Clove oil, Coffee oil, Coriander oil, Costmary
oil (bible leaf oil), Costus root oil, Cranberry seed oil, Cubeb
oil, Cumin oil/Black seed oil, Cypress oil, Cypriol oil, Curry
leaf oil, Davana oil, Dill oil, Elecampane oil, Elemi oil,
Eucalyptus oil, Fennel seed oil, Fenugreek oil, Fir oil,
Frankincense oil, Galangal oil, Galbanum oil, Geranium oil,
Ginger oil, Goldenrod oil, Grapefruit oil, Henna oil,
Helichrysum oil, Hickory nut oil, Horseradish oil, Hyssop,
Idaho-grown Tansy, Jasmine oil, Juniper berry oil, *Laurus
nobilis*, Lavender oil, Ledum, Lemon oil, Lemongrass oil,
Lime oil, *Litsea cubeba* oil, Linaloe, Mandarin, Marjoram,
Melaleuca See Tea tree oil, Melissa oil (Lemon balm),
*Mentha arvensis* oil, Mint oil, Moringa oil, Mountain
Savory, Mugwort oil, Mustard oil, Myrrh oil, Myrtle, Neem
oil or Neem Tree Oil, Neroli, Nutmeg oil, Orange oil,
Oregano oil, Orris oil, Palo Santo, Parsley oil, Patchouli oil,
Perilla essential oil, Pennyroyal oil, Peppermint oil, Petit-
grain, Pine oil, Ravensara, Red Cedar, Roman Chamomile,
Rose oil, Rosehip oil, Rosemary oil, Rosewood oil, Sage oil,
Sandalwood oil, Sassafras oil, Savory oil, Schisandra oil,
Spearmint oil, Spikenard, Spruce Oil, Star anise oil, Tan-
gerine oil, Tarragon oil, Tea tree oil, Thyme oil, Tsuga oil,
Turmeric oil, Valerian oil, Warionia, Vetiver oil (khus oil),
Western red cedar, Wintergreen oil, Yarrow oil, Ylang-ylang,
Zedoary.

Organic oils suitable for use with the present invention
include essential oils selected from the group consisting of:
Dippel's oil, bone oil, cod liver oil, cod-liver oil, lanolin,
wool fat, wool grease, fish oil, fish-liver oil, goose grease,
halibut-liver oil, lard oil, menhaden oil, neat's-foot oil, oleo
oil, porpoise oil, dolphin oil, salmon oil, sardine oil, seal oil,
shark oil, shark-liver oil, sperm oil, tallow oil, train oil,
whale oil, wool oil.

In a particular embodiment, the organic oil(s) is selected
from a marine oil, such as a fish oil, for example, cod oil or
cod-liver oil.

The organic oil(s) (or the oil component as a whole)
suitably comprise less than 50 wt % terpene(s) (e.g. mono-,
di-, tri-, tetra-, poly-terpene(s), squalene, sesquiterpenes,
pinene) and terpene-derived compounds (e.g. terpenoids,
steroids, isoprenoids, sesquiterpenoids), suitably less than
40 wt %, suitably less than 30 wt %, suitably less than 20 wt
%, suitably less than 10 wt %. In a particular embodiment,
the organic oil(s) (or the oil component as a whole) suitably
comprise less than 50 wt % monoterpene(s), suitably less
than 40 wt %, suitably less than 30 wt %, suitably less than
20 wt %, suitably less than 10 wt %. In a particular
embodiment, the organic oil(s) (or the oil component as a
whole) suitably comprise less than 50 wt % pinene(s),
suitably less than 40 wt %, suitably less than 30 wt %,
suitably less than 20 wt %, suitably less than 10 wt %.

The organic oil(s) (or the oil component as a whole)
suitably comprise greater than or equal to 50 wt % fatty
acid(s) or fatty acid-derivatives (e.g. fatty acid esters, glyc-
erides, etc.), suitably greater than or equal to 60 wt %,
suitably greater than or equal to 70 wt %, suitably greater
than or equal to 80 wt %, suitably greater than or equal to
90 wt %.

The organic oil(s) suitably comprises one or more bioac-
tive compounds, suitably omega-3 compounds. The organic
oil(s) suitably comprises one or more omega-3 fatty acids or
omega-3 fatty acid esters. Suitably, the organic oil(s) com-
prises eicosapentaenoic acid (EPA, 20:5) and/or docosa-
hexaenoic acid (DHA, 22:6), or esters of either or both EPA
and/or DHA.

The organic oil(s) suitably comprises one or more com-
pounds which are susceptible to degradation on storage,
suitably oxidative degradation and/or photolytic degrada-
tion. Suitably, once incorporated within a solid composition
of the invention, such compound(s) are rendered less sus-
ceptible to degradation than within the original organic
oil(s).

The oil component or a constituent(s) thereof may have an
unpleasant smell and/or unpleasant taste which is partially or
fully masked when the oil component is formulated within
solid compositions of the invention.

The oil component or any oil contained therein, may be
characterised by reference to its fatty acid composition (or
fatty acid methyl ester composition after converting all fatty
acids to methyl esters). Fatty acids may be referred to by
name, by type (e.g. omega-3, omega-6), or by the well-
established lipid number nomenclature (C: D, where C is the
number of carbon atoms, and D is the number or double
bonds)

Such characterisation usually involves transforming fatty
acids of an oil component into corresponding fatty acid
methyl esters (usually via transesterification) before per-
forming gas-liquid chromatography (GC) to quantify fatty
acid content by reference to their methyl ester derivatives.
Procedures for producing fatty acid methyl esters (FAME)
from fatty acid mixtures are well known in the art, and
Examples of suitable procedures for methylester formation
and GC analysis are presented in Ken'ichi Ichihara and
Yumeto Fukubayashi, "Preparation of fatty acid methyl
esters for gas-liquid chromatography", *J Lipid Res.* 2010
March; 51(3): 635-640, and pertinent references therein.
Such procedures are also described in the Example section
of this specification. Therefore, unless otherwise specified,
quantities and concentrations of fatty acids are expressed in
relation to their corresponding methyl esters.

Suitably, the oil component comprises at least 5 wt %
omega-3 fatty acids, suitably at least 10 wt %, suitably at
least 15 wt %, more suitably at least 20 wt %, suitably at least 30 wt %. Suitably, the oil component comprises at least 5 wt % EPA and DHA (eicosapentaenoic acid and docosahexaenoic acid) combined, suitably at least 10 wt %, suitably at least 15 wt %, more suitably at least 20 wt %, suitably at least 30 wt %.

Suitably, the oil component comprises at most 80 wt % omega-3 fatty acids, suitably at most 70 wt %, suitably at most 50 wt %, suitably at most 40 wt %. Suitably, the oil component comprises at most 80 wt % EPA and DHA combined, suitably at most 70 wt %, suitably at most 50 wt %, suitably at most 40 wt %.

Suitably the Oil Component Comprises:
  at least 5 wt % 16:0 fatty acids;
  at least 5 wt % 18:1 fatty acids;
  at least 2 wt % 20:5 fatty acids; and
  at least 5 wt % 22:6 fatty acids.

Suitably the Oil Component Comprises:
  at least 10 wt % 16:0 fatty acids;
  at least 10 wt % 18:1 fatty acids;
  at least 5 wt % 20:5 fatty acids; and
  at least 10 wt % 22:6 fatty acids.

Suitably the Oil Component Comprises:
  5-35 wt % 16:0 fatty acids;
  5-40 wt % 18:1 fatty acids;
  2-20 wt % 20:5 fatty acids; and
  7-40 wt % 22:6 fatty acids.

Suitably the Oil Component Comprises:
  10-35 wt % 16:0 fatty acids;
  10-30 wt % 18:1 fatty acids;
  5-20 wt % 20:5 fatty acids; and
  10-40 wt % 22:6 fatty acids.

Obviously, the sum of total ingredients of a given composition cannot exceed 100 wt %.

Lipid Component

The lipid component is suitably a solid at SATP. The lipid component may be judiciously selected, for instance, to have a melting point to suit subsequent applications of the resulting solid composition. Generally, the higher the melting point of the lipid component, the higher will be the melting point of the resulting solid composition formed from combining the lipid component with an oil component. Higher melting points may be desirable for a variety of applications, for instance where the final solid composition is used to form a pharmaceutical, nutraceutical, or food supplement product—e.g. in tablets or capsules. However, lower melting points may be preferable where, for instance, subsequent heat-treatments are used in the formation of a final product—for instance where the solid composition is used as 3D printing filaments to print a solid product (or a core thereof) containing the relevant oil and indeed any extra ingredients carried by the oil component and/or lipid component (e.g. a hydrophobic pharmaceutical active). In such circumstances, where high temperatures may compromise the chemical stability of one or more ingredients of the solid composition, it may be desirable to 3D print or otherwise process the solid composition at lower temperatures.

Suitably the lipid component, or a predominant lipid thereof (i.e. the lipid constituting the largest proportion of the lipid component as a whole), has a melting point greater than or equal to 30° C., suitably greater than or equal to 35° C., suitably greater than or equal to 40° C., suitably greater than or equal to 50° C., suitably greater than or equal to 60° C., suitably greater than or equal to 70° C. Suitably the lipid component, or a predominant lipid thereof, has a melting point less than or equal to 200° C., suitably less than or equal to 150° C., suitably less than or equal to 120° C., suitably less than or equal to 100° C., suitably less than or equal to 90° C. In certain embodiments, the melting point of the lipid component, or a predominant lipid thereof, is between 25-90° C., suitably between 30-80° C., suitably between 35-70° C. In certain embodiments, the melting point of the lipid component, or a predominant lipid thereof, is between 50-150° C., suitably between 60-120° C., suitably between 70-100° C.

In light of the knowledge conveyed in this disclosure, those skilled in the art will be able to judiciously tune melting points to suit the desired applications. For instance, longer fatty chains may be used to obtain higher melting points, but lower glycerides (e.g. mono- or di-glycerides) may in some circumstances afford higher melting points due to the extra hydrogen bonding available.

As aforementioned, a lipid component may comprise one or more lipids, though most suitably the lipid component comprises one lipid or predominantly one lipid (i.e. more of one lipid than any other(s)), and suitably a single lipid constitutes at least 50 wt %, suitably at least 70 wt %, suitably at least 80 wt %, suitably at least 90 wt %, suitably at least 95 wt % of the overall weight of the lipid component.

In a particular embodiment, the lipid component comprises one or more lipids (or lipid compounds), each of which comprise one or more fatty acid(s) or fatty acid moiety(ies). The wt % of fatty acid(s) or fatty acid moiety(ies) can be established by means known in the art—e.g. by calculating the proportion of the molecular weight of a given lipid molecule accounted for by the fatty acid(s) or fatty acid moiety(ies). It thus also possible to deduce the weight percentage proportion of a single type of fatty acid or fatty acid moiety relative to all types of fatty acids or fatty acid moieties in a lipid component.

Most suitably, for the purposes of calculating a proportion of a molecular weight constituted by a fatty acid, the weight of atoms of the fatty acid may be calculated up to and including the carbonyl group of the original fatty acid, but suitably excluding any oxygen (e.g. belonging to the alcohol side of a fatty acid ester) or nitrogen (e.g. belonging to the amine side of a fatty acid amide) atoms linking the fatty acid to other parts of the molecule.

In a particular embodiment, the lipid component comprises one or more lipids (or lipid compounds) derived from one fatty acid or predominantly one fatty acid (e.g. the one fatty acid accounts for ≥50 wt %, ≥60 wt %, ≥70 wt %, ≥80 wt %, ≥90 wt %, or ≥95 wt % of the total fatty acids of the one or more lipids), and suitably the lipid(s) or lipid compounds(s) derived from the one fatty acid or predominantly one fatty acid constitute at least 50 wt %, suitably at least 60 wt %, suitably at least 70 wt %, suitably at least 80 wt %, suitably at least 90 wt %, suitably at least 95 wt % of the overall weight of the lipid component.

In a particular embodiment, the lipid component comprises one or more lipids (or lipid compounds) derived from one or more fatty acids, wherein a single fatty acid constitutes at least 50 wt %, suitably at least 60 wt %, suitably at least 70 wt %, suitably at least 80 wt %, suitably at least 90 wt %, suitably at least 95 wt % of all of the fatty acid(s) (or fatty acid moieties) present within the lipid component.

In a particular embodiment, the lipid component comprises one or more lipids (or lipid compounds) derived from one or more fatty acids, wherein a single fatty acid constitutes at least 50 wt %, suitably at least 60 wt %, suitably at least 70 wt %, suitably at least 80 wt %, suitably at least 90 wt %, suitably at least 95 wt % of all of the fatty acid(s) (or fatty acid moieties) of the one or more lipids, and suitably said one or more lipids (i.e. those with the aforementioned fatty acid specification) constitute at least 50 wt %, suitably at least 60 wt %, suitably at least 70 wt %, suitably at least 80 wt %, suitably at least 90 wt %, suitably at least 95 wt % of the overall weight of the lipid component.

In a particular embodiment, at least 50 wt % (though more suitably at least 60 wt %, more suitably at least 70 wt %, more suitably at least 80 wt %, and more suitably at least 90 wt %) of the lipid component consists of one or more fatty acid-based lipids derived from one or more fatty acids, wherein a single fatty acid constitutes at least 50 wt % (though more suitably at least 60 wt %, more suitably at least 70 wt %, more suitably at least 80 wt %) of the total weight of fatty acid(s) (or fatty acid moieties, suitably calculated upto and include its carbonyl group) present within the one or more fatty acid-based lipids.

In a particular embodiment, at least 70 wt % of the lipid component consists of one or more fatty acid-based lipids derived from one or more fatty acids, wherein a single fatty acid constitutes at least 70 wt % of the total weight of fatty acid(s) (or fatty acid moieties, suitably calculated upto and include its carbonyl group) present within the one or more fatty acid-based lipids.

In a particular embodiment, at least 90 wt % of the lipid component consists of one or more fatty acid-based lipids derived from one or more fatty acids, wherein a single fatty acid constitutes at least 80 wt % of the total weight of fatty acid(s) (or fatty acid moieties, suitably calculated upto and include its carbonyl group) present within the one or more fatty acid-based lipids.

In a particular embodiment, at least 90 wt % of the lipid component consists of one or more fatty acid glycerides derived from one or more fatty acids, wherein a single fatty acid (most suitably behenic acid) constitutes at least 80 wt % of the total weight of fatty acid(s) (or fatty acid moieties, suitably calculated upto and include its carbonyl group) present within the one or more fatty acid glycerides.

Lipids are generally hydrophobic or amphiphilic compounds and may inter alia include fats (incl. fatty acids, fatty acid esters, glycerides, fatty alcohols), waxes, sterols, fat-soluble vitamins (such as vitamins A, D, E, and K), mono-glycerides, diglycerides, triglycerides, and phospholipids. Taking account of the biosynthesis of lipids and building blocks for their generation, e.g. ketoacyl or isoprene moieties, lipids may be categorised as fatty acids, glycerolipids, glycerophospholipids, sphingolipids, saccharolipids, and polyketides (the aforementioned being derivable through condensation of ketoacyl subunits); and sterol lipids and prenol lipids (which are derivable through condensation of isoprene subunits).

Suitably, the lipid component comprises a lipid selected from the group consisting of a fatty acid (including esters thereof), a glycerolipid, a glycerophospholipid, a sphingo-lipid, a saccharolipid, a polyketides, a sterol lipid, a prenol lipid, or a mixture thereof. In a particular embodiment, the lipid component comprises a lipid selected from the group consisting of a fatty acid and a glycerolipid, or a mixture thereof. The fatty acid(s) of the lipid component may be free acid(s), fatty acid ester(s), or a mixture thereof. Most suitably, the fatty acid(s) are fatty acid ester(s) of glycerol—i.e. glycerides.

In a particular embodiment, the lipid component comprises a lipid which comprises a fatty acid or fatty acid moiety (e.g. within an ester). Examples of lipids into which fatty acid moieties are incorporated include glycerides and indeed any fatty acid esters—e.g. sugar fatty acid esters, ascorbyl fatty acid esters, etc.

In a particular embodiment, the lipid component comprises at least 50 wt %, more suitably at least 60 wt %, more suitably at least 70 wt %, more suitably at least 80 wt %, more suitably at least 90 wt %, more suitably at least 95 wt %, of one or more lipid compounds, the or all of which are fatty acid lipid compounds, suitably fatty acid esters. Suitably, at least 50 wt % of the fatty acid lipid compounds are derived from a single fatty acid, more suitably at least 60 wt %, more suitably at least 70 wt %, more suitably at least 80 wt % (suitably this applies to mixed glycerides, where such mixed glycerides are derived from a single fatty acid).

In a particular embodiment, the lipid component comprises a lipid selected from the group consisting of a fatty acid mono-glyceride, a fatty acid di-glyceride, a fatty acid tri-glyceride, or a mixture thereof. Most suitably, the lipid is one of or predominantly one of (e.g. ≥70 wt % of the overall weight of the given lipid or lipid component, ≥80 wt %, ≥90 wt %, or ≥95 wt %) a fatty acid mono-glyceride, a fatty acid di-glyceride, or a fatty acid tri-glyceride. In a particular embodiment, the lipid is a triglyceride of a fatty acid. In a particular embodiment, the lipid component comprises at least 33 wt % of a specific glyceride compound, for instance, be it a mono-glyceride of a single fatty acid, a di-gylceride of a single fatty acid, or a tri-glyceride of a single fatty acid. In a particular embodiment, the lipid component comprises at least 40 wt % of a specific glyceride compound, for instance, be it a mono-glyceride of a single fatty acid, a di-gylceride of a single fatty acid, or a tri-glyceride of a single fatty acid. In a particular embodiment, the lipid component comprises at least 50 wt % of a specific glyceride compound, for instance, be it a mono-glyceride of a single fatty acid, a di-gylceride of a single fatty acid, or a triglyc-eride of a single fatty acid. In a particular embodiment, the lipid component comprises at least 33 wt % of a di-gylceride of a single fatty acid, more suitably at least 40 wt %, more suitably at least 50 wt %, suitably where at least 40 wt % of the balance of the lipid component consists of other glyc-erides of the same single fatty acid. In a particular embodi-ment, the lipid component comprises at least 50 wt %, suitably at least 70 wt %, more suitably at least 80 wt %, and most suitably at least 90 wt % fatty acid glyceride, where a single fatty acid constitutes at least 80 wt % of the fatty acid(s) in the fatty acid glyceride, suitably at least 90 wt % thereof, more suitably at least 95 wt % thereof, most suitably at least 99 wt % thereof. As such, in an embodiment of the invention, a specific fatty acid glyceride (i.e. glycerides with one specific fatty acid) may constitute a single lipid, even where mixtures of mono-, di-, and tri-glycerides are present, insofar as the glyceride is of a particular single fatty acid.

In a particular embodiment, the lipid component com-prises at least 40 wt %, more suitably at least 50 wt %, more suitably at least 60 wt %, more suitably at least 70 wt %, more suitably at least 80 wt % of a glyceride mixture of a single fatty acid. In such embodiments, a single glyceride (be it, mono-, di-, or tri-glyceride) constitutes at least 35 wt % of the glyceride mixture, more suitably at least 40 wt %, more suitably at least 45 wt %, suitably at least 50 wt %. Most suitably in such embodiments, the single glyceride in question is the di-glyceride of the single fatty acid. Most suitably the fatty acid is behenic acid/behenate. As such, in a particular embodiment, the lipid component comprises at least 30 wt % of the di-glyceride of behenic acid (glyceryl dibehenate), suitably at least 35 wt %, suitably at least 40 wt %. In such embodiments, at least 50 wt % of the remaining weight balance of the lipid component is other glycerides (e.g. mono- and/or tri-glycerides) of behenic acid, more suitably at least 60 wt % of the remaining balance, more suitably at least 70 wt % of the remaining balance, more suitably at least 80 wt % of the remaining balance.

In certain embodiments, in relation to the lipid component a glyceride mixture of a single fatty acid is considered a single lipid component. A person skilled in the art will appreciate the difficulty of manufacturing a single pure mono-, di-, or tri-glyceride. In such embodiments and contexts, references herein to a single lipid component (e.g. where a lipid component comprises a particular proportion of a single lipid component) may include a glyceride mixture of a single fatty acid. In other embodiments and contexts, however, a single lipid may refer to a single glyceride (whether mono-, di-, or tri-), for instance, where the proportion of a single glyceride is in question. Whether or not a glyceride mixture may be considered a single lipid or plurality of lipids will be clear from the context.

In some embodiments, high purity of the lipid component can be advantageous for affording a "solid oil" in accordance with the invention. As such, suitably the lipid component consists essentially of or consists of a single lipid compound. Moreover, where a specific lipid compound comprises a fatty acid or fatty acid moiety (e.g. glycerides, phospholipids, etc.), suitably said lipid compound comprises only one or predominantly one (e.g. ≥70 wt % of the overall weight of fatty acids or fatty acid moieties in the specific lipid compound, ≥80 wt %, ≥90 wt %, or ≥95 wt %) species of fatty acid or fatty acid moiety—for example, di- or tri-glycerides may suitably respectively comprise two or three of the same fatty acid. As such, mixed glycerides are generally less preferred though not excluded as possibilities.

However, in some embodiments the lipid component comprises two or more lipids. In such embodiments, the melting point of the mixture of lipids (i.e. of the lipid component as a whole) may be as defined herein, and may be as defined herein in relation to melting points of a single lipid.

In a particular embodiment, the lipid component comprises, consists essentially of, or consists of a fatty acid di-glyceride. In a particular embodiment, the lipid component comprises, consists essentially of, or consists of a fatty acid triglyceride. In a particular embodiment, the di-glyceride is glyceryl dibehenate.

In some embodiments, the lipid component may comprise a phospholipid, though most suitably only a small proportion (≤20 wt % of the overall weight of the lipid component, suitably ≤10 wt %, suitably ≤5 wt %, suitably ≤2 wt %) thereof. In a particular embodiment, phospholipon 90H (a phosphatidylcholine) may be used as a suitable phospholipid. The phospholipid is, however, an optional ingredient.

Where the lipid component comprises a fatty acid(s) or fatty acid moiety(ies) (e.g. ester), suitably the fatty acid chain (or tail) has at least 6 carbons, suitably at least 10 carbons, suitably at least 14, suitably at least 18. Where the lipid component comprises a fatty acid(s) or fatty acid moiety(ies) (e.g. ester), suitably the fatty acid chain (or tail) has at most 60 carbons, suitably at least 40 carbons, suitably at least 30, suitably at least 24. Fatty acid(s) with carbon chain lengths between 14 and 28 carbons, between 16 and 26, and between 18 and 24 carbons are especially suitable. The fatty acid(s) may be saturated or unsaturated fatty acid(s).

In a particular embodiment, the fatty acid(s)/moiety(ies) are selected from the group consisting of:

Saturated fatty acid(s)/moiety(ies): myristic acid/myristate, pentadecylic acid/pentadecylate, palmitic acid/palmitate, margaric acid/margarate, stearic acid/stearate, nonadecylic acid/nonadecylate, arachidic acid/arachidate, heneicosylic acid/heneicosylate, behenic acid/behenate, tricosylic acid/tricosylate, lignoceric acid/lignocerate, pentacosylic acid/pentacosylate, and cerotic acid/cerotate; and Unsaturated fatty acid(s)/moiety(ies): myristoleic acid/myristoleate, palmitoleic acid/palmitoleate, sapienic acid/sapienate, oleic acid/oleate, elaidic acid/elaidate, vaccenic acid/vaccenate, linoleic acid/linoleate, linoelaidic acid/linoelaidate, α-linolenic acid/α-linolenate, γ-linolenic acid/γ-linolenate, stearidonic acid/stearidonate, paullinic acid/paullinate, gondoic acid/gondoate, dihomo-γ-linolenic acid/dihomo-γ-linolenate, mead acid/meadate, arachidonic acid/arachidonate, eicosapentaenoic acid/eicosapentaenoate, erucic acid/erucate, docosahexaenoic acid/docosahexaenoate, and nervonic acid/nervonate; or mixtures thereof.

In a particular embodiment, the fatty acid(s)/moiety(ies) are selected from the group consisting of:

Saturated fatty acid(s)/moiety(ies): stearic acid/stearate, arachidic acid/arachidate, behenic acid/behenate, lignoceric acid/lignocerate, and cerotic acid/cerotate; and Unsaturated fatty acid(s)/moiety(ies): oleic acid/oleate, elaidic acid/elaidate, vaccenic acid/vaccenate, linoleic acid/linoleate, linoelaidic acid/linoelaidate, α-linolenic acid/α-linolenate, γ-linolenic acid/γ-linolenate, stearidonic acid/stearidonate, paullinic acid/paullinate, gondoic acid/gondoate, dihomo-γ-linolenic acid/dihomo-γ-linolenate, mead acid/meadate, arachidonic acid/arachidonate, eicosapentaenoic acid/eicosapentaenoate, erucic acid/erucate, docosahexaenoic acid/docosahexaenoate, and nervonic acid/nervonate; or mixtures thereof.

In a particular embodiment, the fatty acid(s)/moiety(ies) are selected from the group consisting of stearic acid/stearate, arachidic acid/arachidate, behenic acid/behenate, lignoceric acid/lignocerate, and cerotic acid/cerotate; and optionally mixtures thereof.

In a particular embodiment, the fatty acid(s)/moiety(ies) is behenic acid/behenate. Behenic acid/behenate fatty acids are particularly appropriate when incorporated within glycerides.

In a particular embodiment, the fatty acid(s)/moiety(ies) is palmitic acid/palmitate.

Additional Ingredients

In addition to an oil component and a lipid component, a solid composition of the invention may further comprise one or more additional ingredients.

The additional ingredient(s) may suitably comprise a pharmaceutical component. A pharmaceutical component may comprise one or more pharmaceutically-active compounds or corresponding pharmaceutically-acceptable salt or solvate thereof. The pharmaceutically-active compound(s), or salt(s)/solvate(s) thereof, may be suitably hydrophobic or otherwise miscible or soluble within the oil component. Suitably, the pharmaceutically-active compound(s) is sparingly-soluble (30-100 parts solvent per part of compound), slightly soluble (100-1000 parts solvent per part of compound), very slightly soluble (1000-10000 parts solvent per part of compound), or practically insoluble (≥10000 parts solvent per part of compound) in water in accordance with USP specifications on drug solubility. Suitably, the pharmaceutically-active compound(s), or salt(s)/solvate(s) thereof, is soluble (10-30 parts solvent per part of compound), freely soluble (1-10 parts solvent per part of compound), or very soluble (less than 1 parts solvent per part of compound) in the oil component, in accordance with USP specifications on drug solubility. The pharmaceutical component may comprise up to 30 wt % of the total weight of the solid composition, suitably up to 20 wt %, suitably up to 10 wt %, suitably up to 5 wt %, suitably up to 2 wt %. The weight ratio of pharmaceutical component to oil component is suitably between 10:1 and 1:100,000, suitably between 1:1 and 1:10,000, suitably between 1:10 and 1:1,000.

The additional ingredient(s) may suitably comprise a nutraceutical component. A nutraceutical component may comprise one or more nutraceutically-active compounds or corresponding nutraceutically-acceptable salt or solvate thereof. The nutraceutically-active compound(s), or salt(s)/solvate(s) thereof, may be suitably hydrophobic or otherwise miscible or soluble within the oil component. Suitably, the nutraceutically-active compound(s) is sparingly-soluble (30-100 parts solvent per part of compound), slightly soluble (100-1000 parts solvent per part of compound), very slightly soluble (1000-10000 parts solvent per part of compound), or practically insoluble (≥10000 parts solvent per part of compound) in water in accordance with USP specifications on drug solubility. Suitably, the nutraceutically-active compound(s), or salt(s)/solvate(s) thereof, is soluble (10-30 parts solvent per part of compound), freely soluble (1-10 parts solvent per part of compound), or very soluble (less than 1 parts solvent per part of compound) in the oil component, in accordance with USP specifications on drug solubility. The nutraceutical component may comprise up to 30 wt % of the total weight of the solid composition, suitably up to 20 wt %, suitably up to 10 wt %, suitably up to 5 wt %, suitably up to 2 wt %. The weight ratio of nutraceutical component to oil component is suitably between 10:1 and 1:100,000, suitably between 1:1 and 1:10,000, suitably between 1:10 and 1:1, 000.

The additional ingredient(s), especially where pharmaceutical or nutraceutical components are also present, may suitably comprise one or more excipients, where the excipients are suitably pharmaceutically- and/or nutraceutically-acceptable excipients.

Such additional ingredient(s) may be a stabiliser component, for instance to further stabilise the oil component. Stabiliser component(s) may, for instance, include antioxidants (e.g. Vit C, ascorbyl palmitate, tocopherol, BHTi, BHA) or preservatives. Such stabiliser component(s) may constitute an excipient.

Such additional ingredient(s) may include aesthetic components, for instance to improve the appearance of the solid composition. Aesthetic components may, for instance, include colourants, pigments, food additives, and such like. Such aesthetic component(s) may constitute an excipient.

The additional ingredient(s) may suitably comprise a surfactant. Such a surfactant benefit the ultimate form of the solid composition or may otherwise assist during processing to produce the solid composition. Alternatively it may be included within the solid composition to facilitate post-processing. Suitably, however, the solid composition of the invention may be substantially free or entirely free of surfactants. Such surfactant(s) may constitute an excipient.

Such additional ingredient(s) may include flavouring components, for instance to improve the taste of the solid composition. Flavouring components may, for instance, include a variety of acceptable flavourants or food additives. Such flavouring component(s) may constitute an excipient.

Additional ingredients may be included to furnish an effervescent product. Such additional ingredients may comprise one or more effervescent agents, for example a combination of a basic gas source and an acid; for instance: a bicarbonate source, such as sodium bicarbonate, and an acid source such as citric acid, tartaric acid.

In a particular embodiment, the solid composition comprises one or more perfumes (or perfume compounds). Suitably a perfume (or perfume compounds) may be incorporated within the solid composition by pre-mixing the perfume(s) with the oil-component, suitably to thereby dissolve said perfume(s) within the oil component prior to mixing with the lipid component.

The person skilled in the art of perfumes appreciates that perfumes may containing one or more of a wide variety of compounds. Perfumes may be obtained from plant sources (e.g. a source of aroma compounds, essential oils, and such like), animal sources, other natural sources, synthetic sources, or any combination thereof. Since perfume compounds are generally hydrophobic, the present invention provides an ideal vehicle for perfumes in a solid form.

Particular Embodiments

In a particular embodiment, a solid composition comprises:

an oil component, wherein the oil component is a liquid at SATP;

a lipid component, wherein the lipid component is a solid at SATP;

wherein the oil component and the lipid component are present in a respective weight ratio of between 1:99 (oil/lipid) and 60:40.

In a particular embodiment, a solid composition comprises:

an oil component, wherein the oil component is a liquid at SATP;

a lipid component, wherein the lipid component is a solid at SATP;

wherein the lipid component constitutes at least 30 wt % of the total weight of the solid composition;

wherein the lipid component comprises a single lipid which constitutes at least 50 wt % of the total lipid component.

In a particular embodiment, a solid composition comprises:

an oil component comprising one or more organic oils, wherein the oil component is a liquid at SATP;

a lipid component, wherein the lipid component is a solid at SATP;

wherein the oil component and the lipid component are present in a respective weight ratio of between 1:99 (oil/lipid) and 60:40;

wherein the lipid component comprises a single lipid which constitutes at least 50 wt % of the total lipid component.

In a particular embodiment, a solid composition comprises:

an oil component comprising one or more organic oils, wherein the oil component is a liquid at SATP and has a kinematic viscosity between 10 and 500 cSt at SATP;

a lipid component, wherein the lipid component is a solid at SATP and has a melting point greater than or equal to 40° C.;

wherein the lipid component constitutes at least 30 wt % of the total weight of the solid composition;

wherein the oil component constitutes at least 10 wt % of the total weight of the solid composition.

In a particular embodiment, a solid composition comprises:

an oil component comprising one or more organic oils, wherein the oil component is a liquid at SATP and comprises eicosapentaenoic acid (EPA, 20:5) and/or docosahexaenoic acid (DHA, 22:6), or esters of either or both EPA and/or DHA;

a lipid component, wherein the lipid component is a solid at SATP and has a melting point greater than or equal to 40° C.;

wherein the lipid component constitutes at least 30 wt % of the total weight of the solid composition;

wherein the oil component constitutes at least 10 wt % of the total weight of the solid composition.

In a particular embodiment, a solid composition comprises:

an oil component comprising one or more organic oils, wherein the oil component is a liquid at SATP and comprises:

at least 5 wt % 16:0 fatty acids;

at least 5 wt % 18:1 fatty acids;

at least 2 wt % 20:5 fatty acids; and at least 5 wt % 22:6 fatty acids.

a lipid component, wherein the lipid component is a solid at SATP.

In a particular embodiment, a solid composition comprises:

an oil component comprising one or more organic oils, wherein the oil component is a liquid at SATP and comprises:

5-35 wt % 16:0 fatty acids;

5-40 wt % 18:1 fatty acids;

2-20 wt % 20:5 fatty acids; and 7-40 wt % 22:6 fatty acids;

a lipid component, wherein the lipid component is a solid at SATP.

In a particular embodiment, a solid composition comprises:

an oil component comprising one or more organic oils, wherein the oil component is a liquid at SATP and comprises:

at least 5 wt % 16:0 fatty acids;

at least 5 wt % 18:1 fatty acids;

at least 2 wt % 20:5 fatty acids; and at least 5 wt % 22:6 fatty acids.

a lipid component, wherein the lipid component is a solid at SATP, has a melting point greater than or equal to 40° C., and comprises a single lipid that constitutes at least 70 wt % of the lipid component and comprises a fatty acid or fatty acid moiety.

In a particular embodiment, a solid composition comprises:

an oil component, wherein the oil component is a liquid at SATP;

a lipid component, wherein the lipid component is a solid at SATP; and a pharmaceutical component.

In a particular embodiment, a solid composition comprises:

an oil component, wherein the oil component is a liquid at SATP;

a lipid component, wherein the lipid component is a solid at SATP; and a pharmaceutical component comprising one or more pharmaceutically-active compound(s), wherein the pharmaceutically-active compound(s) are soluble (10-30 parts solvent per part of compound), freely soluble (1 10-parts solvent per part of compound), or very soluble (less than 1 parts solvent per part of compound) in the oil component, in accordance with USP specifications on drug solubility.

In a Particular Embodiment, a Solid Composition Comprises:

an oil component, wherein the oil component is a liquid at SATP;

a lipid component, wherein the lipid component is a solid at SATP; and a nutraceutical component.

In a Particular Embodiment, a Solid Composition Comprises:

an oil component, wherein the oil component is a liquid at SATP;

a lipid component, wherein the lipid component is a solid at SATP; and a nutraceutical component comprising one or more nutraceutically-active compound(s), wherein the nutraceutically-active compound(s) are soluble (10-30 parts solvent per part of compound), freely soluble (1-10 parts solvent per part of compound), or very soluble (less than 1 parts solvent per part of compound) in the oil component, in accordance with USP specifications on drug solubility.

In a Particular Embodiment, a Solid Composition Comprises:

an oil component, wherein the oil component is a liquid at SATP; and a lipid component, wherein the lipid component is a solid at SATP;

wherein the oil component is or comprises a nutraceutical/ pharmaceutical component (e.g. fish oil); and the solid composition comprises particles having an average particle size greater than or equal to 10 μm.

In a particular embodiment, a solid composition is a nutraceutical/pharmaceutical marine oil composition comprising:

an oil component, comprise one or more marine oil(s), wherein the oil component is a liquid at SATP; and a lipid component, wherein the lipid component is a solid at SATP;

wherein suitably the solid composition comprises particles having an average particle size greater than or equal to 10 μm.

In relation to any, some, or all of the aforesaid particular embodiments, suitably at least 70 wt % of the lipid component consists of one or more fatty acid glycerides derived from one or more fatty acids, wherein a single fatty acid (most suitably behenic acid or stearic acid) constitutes at least 70 wt % of the total weight of fatty acid(s) (or fatty acid moieties, suitably calculated upto and include its carbonyl group) present within the one or more fatty acid glycerides.

According to a further aspect of the present invention there is provided an orally-administrable composition (suitably an orally-administrable nutraceutical or pharmaceutical composition or a composition suitable for preparing an orally-administrable nutraceutical or pharmaceutical composition, e.g. through dissolution or dispersion in water) comprising an oil component and a lipid component. In an embodiment, the oil component is or comprises one or more marine oil(s), suitably one or more fish oil(s). In an embodiment, the orally-administrable composition is a free-flowing particulate solid (e.g. a sachet for dissolving and/or dispersing in water prior to oral administration). In an embodiment, the orally-administrable composition is tablet.

According to a further aspect of the present invention there is provided an orally-administrable solid dosage form, wherein the solid dosage form comprises a solid composition as defined herein or an orally-administrable composition as defined herein. The solid dosage form may be a free-flowing particulate solid (e.g. a sachet for dissolving and/or dispersing in water prior to oral administration). In an embodiment, the orally-administrable solid dosage form is selected from the group consisting of a pill or tablet (e.g. a compressed solid composition of the invention, optionally with one or more excipients), and a capsule (e.g. a solid composition of the invention encased in a capsule shell).

The solid composition of the invention may be in the form of an inhalable composition. As such, the present invention provides an inhaler device (e.g. for inhalation via mouth or nose) comprising (suitably dispensibly contained within a compartment thereof) a solid composition as defined herein.

It will be apparent that solid compositions of the invention may be incorporated in a range of products and used in a range of applications.

In a particular embodiment, the solid composition is a 3D printing filament, suitably a 3D printing filament suitable for use in fused filament fabrication (FFF) printing. Suitably such filaments have a melting point less than or equal to 100° C., suitably less than or equal to 80° C., suitably less than or equal to 70° C., suitably less than or equal to 60° C.

In a particular embodiment, the solid composition comprises an oil component and a lipid component in a relative weight ratio of between 5:95 and 70:30, wherein the lipid component comprises a single lipid that constitutes at least 70 wt % of the total weight of lipid component, and the lipid component is a solid at SATP.

In a particular embodiment, the solid composition comprises an oil component and a lipid component in a relative weight ratio of between 10:90 and 60:40, wherein the oil component consists of one or more organic oils, wherein the lipid component comprises a single lipid that constitutes at least 80 wt % of the total weight of lipid component, and the lipid component is a solid at SATP and has a melting point greater than or equal to 50° C. and less than or equal to 200° C.

Methods of Preparing Solid Composition

Equipped with the knowledge disclosed herein, the skilled person will appreciate there are a variety of methods that may be utilised to form a solid composition of the invention.

The present invention provides a method of preparing a solid composition, comprising mixing together an oil component and a lipid component to form an oil-lipid mixture, and optionally further processing the oil-lipid mixture. The oil-lipid mixture may be the solid composition, or further processing of the oil-lipid mixture may furnish the solid composition.

Suitably the oil component and lipid component are mixed together so that the lipid component encapsulates the oil component. As such, a predominantly-lipid shell may encapsulate an oil-component-containing core, or a multiplicity of oil component-containing "cores" may be encased within and distributed throughout a predominantly-lipid matrix. It will be understood that a quantity of lipid may reside in the core(s) and that some oil component may be present within a lipid shell or lipid matrix. However, suitably the solid compositions formed have relatively little surface oil (i.e. little oil component at the surface) and relatively little oil component within the lipid shell/matrix, thereby allowing lipid molecules to interact effectively to form a solid state.

Batch Preparation

Input Compositions

The method of preparing a solid composition of the invention requires certain input materials. The input materials suitably comprise an oil component and a lipid component in relative amounts desired in the ultimate solid composition. Suitably relative amounts are given elsewhere herein. Optionally, a small quantity of an additional lipid, such as a phospholipid (suitably ≤10 wt % of total weight of oil component, lipid component, and additional lipid, suitably ≤5 wt % but suitably ≥0.1 wt %, suitably ≥1 wt %) may be included as an input ingredient. The oil component, lipid component, and optional additional lipid may be collectively considered as oil input materials. As such, the input materials suitably comprise the oil input materials.

The method may additionally include aqueous input materials, which suitably comprises water and optionally a stabiliser. If a stabiliser is present, suitably it is present in the aqueous phase at a relatively low concentration, suitably less than or equal to 5 mg/mL, suitably less than or equal to 2 mg/mL, suitably less than or equal to 1 mg/mL, suitably about 0.5 mg/mL, and suitably greater than or equal to 0.01 mg/mL, suitably greater than or equal to 0.1 mg/mL.

Oil-Lipid Mixture

Suitably, the oil input materials (oil component, lipid component, and optional additional lipid component) are transformed into an oil-lipid mixture.

In a particular embodiment, the oil component and lipid component (and optionally also the additional lipid) are first mixed as a "melt" (i.e. in a heated state), in relative proportions desired within the solid composition—this affords an oil-lipid mixture, suitably in a liquid state.

The oil-lipid mixture may be formed by melting the lipid component by heating the lipid component to or above its melting point, and thereafter adding the oil component to the melted lipid component (optionally the oil itself may be pre-heated or the mixture is maintained at or above the melting point of the lipid component) or transferring the melted lipid component to the oil component (again optionally the oil itself may be pre-heated or the mixture may be maintained at or above the melting point of the lipid component). This procedure may be varied, but ideally the oil and lipid components should be mixed together and the mixture formed as a liquid. The oil-lipid mixture may remain heated until further processed, though optionally the mixture may be cooled and reheated as required (e.g. to remelt).

Further Processing of Oil-Lipid Mixture

In a particular embodiment, the oil-lipid mixture is added to a preheated aqueous phase (suitably aqueous input materials as set forth above), which is suitably pre-heated at or above the melting point of the lipid component. The aqueous phase may be simply water, though in some embodiments the aqueous phase may additionally comprise a small quantity of a stabiliser (e.g. Kolliphore P-188). In some embodiments, the stabiliser may be a surfactant.

Addition of the oil-lipid mixture to the aqueous phase suitably affords an aqueous dispersion (e.g. oil-in-water dispersion). Suitably, substantially no emulsion is formed. The aqueous dispersion may be agitated (e.g. stirred), suitably at low RPM (suitably between 500 and 700 RPM, suitably between 500 and 1000 RPM and suitably no more than or equal to 2000) for a period of time following its formation (e.g. following complete addition of the oil-lipid mixture), suitably at least 2 minutes, though suitably less than 20 mins, suitably less than 10 mins, suitably about 5 minutes. Suitably, after a suitably time period (e.g. suitably as per above suggested), the dispersion is cooled, suitably rapidly cooled (suitably within a 10 minute period, suitably within a 5 minute period, suitably within a 2 minute period), suitably "crash cooled", suitably to a temperature at or below 20° C., suitably at or below 10° C., suitably at or below 2° C., suitably about 0° C., suitably at or above −20°

C., suitably at or above −10° C., suitably at or above −4° C., and suitably the aqueous dispersion is agitated (e.g. stirred) during cooling. After cooling, a particulate dispersion or suspension (suitably not an emulsion) is suitably formed, suitably containing particles of solid composition. The particulate dispersion/suspension may be stirred for a period of time, suitably at least 2 mins, suitably at least 4 minutes, suitably no more than 2 hrs, suitably no more than 60 minutes. Suitably particles of solid composition are separated from the particulate dispersion/suspension, suitably via filtration (suitably via a filtration device exhibiting a mesh size greater than 10 µm, suitably greater than 20 µm, suitably greater than 30 µm, suitably greater than 50 µm, suitably greater than 1000 µm), and suitably the particles of solid composition are collected. The collected particles of solid composition are suitably dried, suitably under vacuum. Suitably this yields a free-flowing particulate solid. The particle size may be affected by a number of factors, including stabiliser usage. Use of surfactants in the aqueous input materials will tend to yield smaller particles, though overuse can prevent solid formation. As such, in some embodiments only minimal or no surfactant is used.

Rapid cooling can be achieved in a variety of ways known in the art. This may involve transferring the aqueous dispersion to a separate container (suitably equipped with an agitator, such as a stirred, to maintain agitation of the aqueous dispersion during cooling) which is pre-cooled or contains a pre-cooled quantity of water and/or ice, optionally containing one or more salts.

In an alternative embodiment, the oil-lipid mixture may be extruded, suitably via a hot-melt extrusion process, suitably using a hot-melt extrusion device. Suitably an oil-lipid mixture is added to or formed within a hot melt extruder, suitably in a substantially homogeneous fashion. The oil-lipid mixture is suitably extruded from the hot-melt extrusion device to yield an extruded solid composition in accordance with the invention. The extruded solid composition may be in the form of a filament, suitably a 3D printing filament. As such, the filament may be used in 3D printing to print solid compositions of the invention or to print an article (e.g. tablet) comprising a solid composition (or the components thereof) of the invention. Alternatively the extruded solid composition may be crushed, milled, grinded, or granulated to produce particles of solid composition.

Suitably the method of preparing the solid compositions of the invention forms particles comprising an oil component encapsulated within a lipid matrix. Suitably the degree of encapsulation (relative to the method's input ingredients, especially of the oil component) is greater than or equal to 40%, suitably greater than or equal to 50%, suitably greater than or equal to 60%, suitably greater than 70%, suitably greater than 70%. Degree of encapsulation may be expressed via the following equation:

$$D_e = \frac{E_o}{I_o}$$

where $D_e$ is the degree of encapsulation (which can be expressed as a percentage by multiplying by 100), $E_o$ is the weight of the oil component encapsulated within the solid composition product, and $I_o$ is the input weight of the oil component.

Suitably the overall yield of solid composition (as compared to input lipid component and oil component) is greater than or equal to 50%, suitably greater than or equal to 60%, suitably greater than or equal to 70%, suitably greater than or equal to 80%.

Continuous Preparation

The aforementioned batch processes are examples of processes that may be deployed to produce solid compositions of the invention. However, the skilled person will appreciate that various alternative processes may be deployed based on the teachings contained herein. Such processes may include continuous flow chemistry, wherein input feeds, mixing, and output feeds may be processed in a continuous manner.

Oil-Containing Product

The present invention provides an oil-containing product. The oil-containing product suitably comprises a solid composition of the invention, or suitably incorporates the components of the solid composition following any processing required to produce the oil-containing product. For instance, the solid composition may be mixed with one or more further ingredients to afford an oil-containing product which comprises a mixture of the one or more further ingredients with the components of the solid composition.

Preparing the oil-containing product may suitably comprise incorporating the solid composition within a product. Alternatively the oil-containing product may be prepared by transforming the solid composition into the oil-containing product, suitably after the solid composition has been independently produced. Alternatively the oil-containing product may be prepared by producing the oil-containing product during (or as part of) a method of preparing the solid composition per se.

In a particular embodiment, the oil-containing product is selected from the group consisting of a pharmaceutical composition, a nutraceutical composition, a food additive composition, a foodstuff, a 3D printing element or filament, and an article produced by 3D printing of the solid composition.

In a particular embodiment, the oil-containing product is a pharmaceutical composition or a nutraceutical composition. The pharmaceutical or nutraceutical composition may a solid pharmaceutical or nutraceutical composition, such as a tablet, capsule, or particulate solid. Such pharmaceutical or nutraceutical compositions may be formed, using solid compositions of the invention, by methods well-known in the art. For example, the solid composition may be transformed directly into a solid pharmaceutical or nutraceutical composition, or may be first processed (e.g. blended with) one or more excipients prior to being transformed into the solid pharmaceutical or nutraceutical composition.

A nutraceutical composition, or nutraceutical product, comprising a solid composition (or formed from a solid composition) may comprise nutritional ingredients. Such nutritional ingredients are suitably a part of the oil component itself—for instance omega 3s. Alternative or additionally nutraceutical ingredients may be incorporated after or during the production of the solid composition.

A pharmaceutical composition, or pharmaceutical product, comprising a solid composition (or formed from a solid composition) may suitably comprise one or more pharmaceutically active ingredients. Again, a pharmaceutically active ingredient may be a constituent part of the oil component itself, especially where the oil component comprises compounds with therapeutic properties. A pharmaceutically active ingredient may be additional and may, for instance, be pre-dissolved in the oil component (especially where the pharmaceutical ingredient is suitably hydrophobic). As such, solid compositions of the invention may provide an excellent vehicle for delivering hydrophobic pharmaceutical actives.

A food supplement composition, or food supplement product, comprising a solid composition (or formed from a solid composition) may suitably comprises one or more food supplements.

A nutraceutical, pharmaceutical, or food supplement composition of the invention may be an oral dosage form thereof, suitably for oral administration to a subject in need thereof.

In a particular embodiment, the oil-containing product is a personal care product. In an embodiment, the oil-containing product is a personal care product selected from the group consisting of cosmetics, cleansing pads, colognes, cotton swabs, cotton pads, deodorant, eye liner, facial tissue, hair clippers, lip gloss, lipstick, lip balm, lotion, makeup, hand soap, facial cleanser, body wash, nail files, pomade, perfumes, razors, shaving cream, moisturizer, talcum powder, toilet paper, toothpaste, facial treatments, wet wipes, and shampoo. In a particular embodiment, the oil-containing product is a perfume or a perfumed item (i.e. a product comprising the perfume, including any of the aforementioned personal care products). In such embodiments, the perfume may comprise a solid composition of the invention, suitably a particulate form thereof (whether free-flowing, compressed, granulated, or otherwise modified). The oil-containing product comprising a perfume of the invention may include a washing composition, for example, a laundry product (e.g. laundry compositions for a washing machine and/or drier), dishwasher products, or other such items. Suitably, a perfume (or one or more perfume compounds) may be incorporated (or mixed with during production) the oil component of the solid composition of the invention. In this manner, the oil component may dissolve a perfume (or plurality thereof) so that the perfume(s) may be distributed throughout the solid composition.

Where a solid composition of the invention is incorporated within an oil-containing product, said solid composition may be present within the oil-containing product in a (partially) transformed form. For instance, a particulate form of the solid composition of the invention may be in a compressed form (e.g. so as to form a monolith comprising the plurality of particles) or perhaps a granulated form (whether formed by dry or wet granulation processes).

Solid compositions of the invention may be or may be used to form a variety of oil-containing products, which may have a variety of uses. For instance, solid compositions, or oil-containing products formed therefrom, may be used in cooking, for instance for frying or as a food additive, optionally as a carrier for hydrophobic food additives. Other uses include cosmetics, paints, coolants (for heat transfer), solid lubricants, solid fuel additives, and solid fuels.

EXAMPLES

Embodiments of the invention are now illustrated by reference to the following Examples. The skilled person will appreciate that the Examples presented below are illustrative of broad principles and that the scope of the invention is not limited by these Examples.

In general, the present invention enables transformation of difficult-to-handle messy oils into solids, suitably free-flowing solids as illustrated in FIG. 1.

FIG. 1 shows pictorially two different types of oily substance and the powdery product into which they may be converted by implementing the present invention.

Example 1—General Procedure for Converting Marine, Vegetable, Essential Oils, or Oily Bioactives into Free-Flowing Lipid Microparticles Using a Melt Dispersion Technique Example quantities of input materials are given in Table 1.

Initially, solid lipid (glyceryl dibehenate or any other suitable lipid) and phospholipon-90H/lecthin (optional) were melted and then the oil (marine or vegetable or essential oil or oily bioactive) was added and the mixture was maintained at 70° C. on a hot water bath. Separately, hot aqueous phase containing a low concentration of a hydrophilic surfactant Kolliphore P-188 was heated and maintained at 70° C. The oily phase (at 70° C.) was then dispersed in the aqueous phase (at 70° C.) under stirring condition and further stirred for 5 minutes after addition was complete. This dispersion was then rapidly cooled by pouring it in a precooled container maintained in ice bath (approximately 0° C. for at least 20 min prior) under stirring condition for 5 min and then filtered on a Buchner funnel under vacuum and kept for drying at least more than 30 min covered with aluminium foil (to avoid exposure to light) to yield free flowing microparticles (FIG. 2).

FIG. 2 shows pictures of fish oil (left), prior to transformation, and fish oil microparticles (right) following transformation.

TABLE 1

| Composition of microparticles containing 50:50 fish oil to lipid | |
| --- | --- |
| Ingredients | Quantity (g) |
| Fish oil | 3.0 |
| Glyceryl dibehenate (GDB) | 3.0 |
| Phospholipon-90H | 0.1 |
| Kolliphore P-188 | 0.025 |
| Deionised water | 50.0 mL |

Our main aim was to incorporate maximum amount of bioactive oil and transfer into free-flowing powder, so we started formulations with lower ratios of fish oil from 10, 20, 30, 40 and 50% up to 50% ratio the fish oil were able to convert into free-flowing powders. However, increasing the ratio of fish oil:GDB to 60:40 hampered the flowability of the powder. From our experiments, for optimal free-flowing microparticles, the maximum amount of fish oil incorporated was 50%. Table 2 below shows examples of various ratios of fish oil and GDB attempted to convert to free-flowing powder.

TABLE 2

| Examples of different compositions of fish oil used in the preparation of microparticles | | | | |
| --- | --- | --- | --- | --- |
| Fish oil (gm, %) | GDB (gm, %) | Candellia wax (gm, %) | Carnauba wax (gm, %) | Comments |
| 1.8 (30%) | 4.2 (70%) | — | — | Free flowing powder |
| 2.4 (40%) | 3.6 (60%) | — | — | Free flowing powder |

TABLE 2-continued

Examples of different compositions of fish oil
used in the preparation of microparticles

| Fish oil (gm, %) | GDB (gm, %) | Candellia wax (gm, %) | Carnauba wax (gm, %) | Comments |
|---|---|---|---|---|
| 3 (50%) | 3 (50%) | — | — | Free flowing powder |
| 3.6 (60%) | 2.4 (40%) | — | — | Clumping |
| 3.6 (60%) | 2.16 (36%) | 0.24 (4%) | — | Clumping |
| 3 (50%) | 2.76 (45%) | 0.24 (4%) | — | Free flowing powder |
| 3.3 (55%) | 2.4 (40%) | 0.30 (5%) | — | Clumping |
| 3.3 (55%) | 2.2 (35%) | 0.48 (10%) | — | Clumping |
| 3.6 (60%) | 1.2 (20%) | 1.2 (20%) | — | Clumping |
| 3.6 (60%) | 2.16 (36%) | — | 0.24 (4%) | Clumping |
| 3.3 (55%) | 2.4 (40%) | — | 0.30 (5%) | Clumping |
| 3 (50%) | 2.76 (45%) | — | 0.24 (5%) | Clumping |

*Note:
The above compositions contain Phospholipon-90H 0.1 gm (1.6%) and Kolliphore in range 0.025 to 0.2 gm (0.41-3.17%)

Effect of Particle Size During Congealing in Ice Water with Time:

After congealing the mixture in ice chilled water, mixture was taken at 0, 20 and 60 min the and analysed for microparticles size using laser diffraction (Master sizer), and the results showed there is no much difference in particle size even after keeping in ice cold condition for 60 min (Table 3). The time of congealing did not have any major effect on the formation of the microparticles. A minimum time of 5 minutes was sufficient to congeal the lipid to yield microparticles.

TABLE 3

Effect of particle size during congealing in ice water

| Time of stirring (min) | Average Particle size, d (0.5) μm |
|---|---|
| 5 | 77.86 |
| 20 | 78.632 |
| 60 | 82.894 |

Effect of Surfactant in Converting Fish Oil to Fish Oil Microparticles:

Particle size was also checked for formulations with and without surfactants and their effects on particle size was observed. Incorporation of small quantity surfactant (0.05% of aqueous phase) in the water resulted in achieving microparticles with smaller particle size.

TABLE 4

Effect of particle size with and without surfactant

| Fish oil microparticles | d (0.5) μm |
|---|---|
| with P-90H and Kolliphore | 87.268 |
| with no P-90H | 171.212 |
| with no P-90H and Kolliphore | 352.07 |

Example 2—General Procedure for Converting Marine, Vegetable, Essential Oils, or Oily Bioactives to Free-Flowing Lipid Microparticles Using Hot Melt Extrusion Technique Hot melt extrusion technique has been used for encapsulation of solid drugs in solid lipid matrix (Rosiaux, Y. et al., 2015). However there are no reports of encapsulation of oils in lipid matrix using this technique. The present invention utilises solid lipids for encapsulation of oils (marine, vegetable and essential) using hot melt technology.

FIG. 3 shows a twin-screw hot melt extruder alongside its technical specifications.

Glyceryl dibehenate and fish oil were extruded using a Pharma 11 HME (Twin screw extruder) (FIG. 3). Initial temperature was maintained at 25° ° C. and GDB and fish oil were fed into the feeding zone over the period of 5 min (for an 8.0 g batch) feeding 1.0 g fish oil and 1.0 g of GDB alternatively. Whilst feeding, the rate of screw speed was increased step wise from 0.0 to 40.0 rpm to ensure uniform mix. After the feeding was complete, the temperature was increased to 60° C. (extrusion temperature) to obtain solid extrudates with immediate solidification at the die exit. The extrudates were milled to yield free flowing powder (FIG. 4). This technique has an advantage no separate cooling system is required.

FIG. 4 shows fish oil microparticles containing 50% oil, produced using hot melt extrusion.

TABLE 5

Different ratios of oils and GDB used
in the preparation of microparticles

| Oil (g, %) | GDB (g, %) | Comments |
|---|---|---|
| Evening Primrose | | |
| 3 (50%) | 3 (50%) | Free flowing powder |
| 2.4 (40%) | 3.6 (60%) | Free flowing powder |
| 1.2 (20%) | 4.8 (80%) | Free flowing powder |
| Castor oil | | |
| 3 (50%) | 3 (50%) | Free flowing powder |
| 2.4 (40%) | 3.6 (60%) | Free flowing powder |
| 1.2 (20%) | 4.8 (80%) | Free flowing powder |
| Coconut oil | | |
| 3 (50%) | 3 (50%) | Free flowing powder |
| 2.4 (40%) | 3.6 (60%) | Free flowing powder |
| 1.2 (20%) | 4.8 (80%) | Free flowing powder |
| Peppermint oil | | |
| 3 (50%) | 3 (50%) | Free flowing powder |
| 2.4 (40%) | 3.6 (60%) | Free flowing powder |
| 1.2 (20%) | 4.8 (80%) | Free flowing powder |
| Flaxseed oil | | |
| 3 (50%) | 3 (50%) | Free flowing powder |
| 2.4 (40%) | 3.6 (60%) | Free flowing powder |
| 1.2 (20%) | 4.8 (80%) | Free flowing powder |
| Fish oil | | |
| 3 (50%) | 3 (50%) | Free flowing powder |
| 2.4 (40%) | 3.6 (60%) | Free flowing powder |
| 1.2 (20%) | 4.8 (80%) | Free flowing powder |
| Neem seed oil | | |
| 3 (50%) | 3 (50%) | Free flowing powder |
| 2.4 (40%) | 3.6 (60%) | Free flowing powder |
| 1.2 (20%) | 4.8 (80%) | Free flowing powder |
| Rape seed oil | | |
| 3 (50%) | 3 (50%) | Free flowing powder |
| 2.4 (40%) | 3.6 (60%) | Free flowing powder |
| 1.2 (20%) | 4.8 (80%) | Free flowing powder |

Example 3—Formulation of "Solid Oils" Using Various Lipids

The microparticles were prepared with different lipids. The following Table 6 gives the range of lipids that can be used to prepare oil (marine, vegetable, essential) loaded microparticles. The lipids that can be used for preparing microparticles include but not restricted to glycerides (triglycerides, diglycerides, and monoglycerides, and mixtures thereof), nonglyceride lipids (sphingolipids, steroids, and waxes), fatty acids, and fatty alcohols.

TABLE 6

Composition and melting temperature ranges of various lipids for preparation of oil loaded microparticles.

| Lipids | Composition | Melting temperature |
|---|---|---|
| Compritol 888 ATO | Glycerol esters of behenic acid Glycerol dibehenate (52-54%) Glycerol tribehenate (28-32%) Glycerol monobehenate (12-18%) | 69-74° C. |
| Imwitor 900 K | Glyceryl stearate, contains 40 to 55% monoglycerides | 54-64° C. |
| Imwitor 491 | Glyceryl stearate, contains more than 90% monoglycerides | 66-77° C. |
| Precirol ATO 5 ® | Glyceryl distearate | 56° C. |
| Dynasan 118 | Tristearin | 70-73° C. |
| Dynasan 114 | Trimyristin | 56-56.5° C. |
| Stearic acid | Saturated fatty acid with 18 carbon chain | 69.3° C. |
| Myristic acid | Saturated fatty acid with 14 carbon chain | 54° C. |
| Palmitic acid | Saturated fatty acid with 16 carbon chain | 63° C. |
| Behenic acid | Saturated fatty acid with 21 carbon chain | 80.0° C. |
| Stearyl alcohol | Saturated fatty alcohol with 18 carbon chain | 59.4 to 59.8° C. |
| Cetyl alcohol | Saturated fatty alcohol with 16 carbon chain | 49° C. |
| Cetostearyl alcohol | Mixture of fatty alcohols, consisting predominantly of cetyl and stearyl alcohols | 50° C. |
| Carnauba wax | Mixture of fatty esters (80-85%), free alcohols (10-15%), acids (3-6%) and hydrocarbons (1-3%) | 78-85° C. |
| Candellia wax | Mixture of hydrocarbons (about 50% of C29 to C33, mainly C31), esters (28-29%), alcohols, | 67-79° C. |

TABLE 6-continued

Composition and melting temperature ranges of various lipids for preparation of oil loaded microparticles.

| Lipids | Composition | Melting temperature |
|---|---|---|
| | free fatty acids (7-9%), and resins (12-14% triterpenoid esters) | |
| Ozocerite | Hydrocarbons (C20-C32) | 90° C. |
| Cetyl palmitate | Fatty acid esters | 54° C. |
| Cetostearyl stearate | Fatty acid esters | 57.00° C. |
| Stearyl stearate | Fatty acid esters | 62-70° C. |

TABLE 7

Compositions with different type of lipids used for preparation of microparticles

| Lipids, g (%) | Fish oil, g (%) | Compritol 888 ATO | Carnauba wax, g (%) | Comments |
|---|---|---|---|---|
| Imwitor 900 K | | | | |
| 3.0 (50%) | 2.4 (40%) | | 0.6 (10%) | Free flowing powder |
| 3.3 (55%) | 2.7 (45%) | | — | Free flowing powder |
| 3.6 (60%) | 2.4 (40%) | | — | Free flowing powder |
| 1.2 (20%) | 2.4 (40%) | 2.4 (40%) | | Free flowing powder |
| Imwitor 491 | | | | |
| 3.6 (60%) | 2.4 (40%) | | — | Free flowing powder |
| 3.0 (50%) | 2.4 (40%) | | 0.6 (10%) | Free flowing powder |
| 3.0 (50%) | 1.8 (30%) | | 1.2 (20%) | Free flowing powder |
| 4.2 (70%) | 1.8 (30%) | | — | Free flowing powder |
| Dynasan 118 | | | | |
| 3.0 (50%) | 3.0 (50%) | | — | Free flowing powder |
| 3.6 (60%) | 2.4 (40%) | | — | Free flowing powder |
| Dynasan 114 | | | | |
| 3.0 (50%) | 3.0 (50%) | | — | Clumping |
| 3.6 (60%) | 2.4 (40%) | | — | Free flowing powder |
| 3.0 (50%) | 2.4 (40%) | | 0.6 (10%) | Free flowing powder |

The percentage of the oil that can be loaded onto the lipid microparticles is dependent upon the melting point and composition of lipids. Higher melting lipids can load higher amount of oil.

Analytical Protocols

To understand the stability of lipid microparticles a detailed study has been carried out on fish oil microparticles. As fish oil contains bioactive Omega 3 fatty acids, eicosapentaenoic acid (EPA) and docosahexaenoic acid (DHA), fish oil was therefore quantified in terms of EPA and DHA. Gas chromatography mass spectrometry (GC-MS) was used to quantify the EPA and DHA in fish oil.

Omega 3 acids are prone to oxidation (Ismail A, et al., 2016), oxidation is an undesirable sequence of chemical reactions, involves the oxygen to degrade the quality of oils (Choe, E, et al., 2006). It is not possible to stop completely the oxidation but it can always be reduced. Oxidation is a complex process and progresses by break down of double bonds by the oxygen interaction, initially it forms primary oxidation products (Annamalai. J, et al., 2015) (peroxides, dienes and free fatty acids) and then finally secondary products (Carbonyls, aldehydes). Oxidation proceeds at different rates based on the availability of light, temperature and oxygen. As fish oil is prone to oxidation and forms secondary oxidation products (aldehydes) during storage, a detailed storage stability studies for fish oil microparticles was carried out to determine the oxidative degradation. Following standard tests were performed for identifying oxidation products:

p-Anisidine value
  Peroxide Value
  TOTOX
  TBARS

Additionally, following advanced analytical techniques were also used in identifying the degradation products.

GC-MS and
  1H-NMR

The analytical methods used for quantification of EPA and DHA and oxidation degradation are described below.

Quantification of Bioactives (Omega-3 Fatty Acids EPA and DHA) in Fish Oil and Fish Oil Microparticles by GC-MS GC-MS quantification of EPA and DHA acids is not possible therefore these omega-3 acids need to be converted into esters by esterification process (Pathak, S, et al., 2015). Method given in USP 39 was adapted and used for GC-MS analysis and quantification of EPA and DHA.

GC-MS instrumentation conditions (Yi, T, et al., 2014): Thermo scientific, trace 1300 Gas Chromatograph (UK) was used for qualitative and quantitative analysis of fish oil and fish oil microparticles. DB-5 MS high-resolution capillary column (thickness: 0.25 µm, length: 30 m, diameter: 0.25 mm) was used for sample separation. For temperature programming, the oven was maintained at 80° C. for one minute and then increased at a rate of 10° C. per minute to 250° C., and maintained for 5 min. Split injection was conducted with a split ratio of 10:1, and helium was used as the carrier gas at a rate of 0.8 ml/min, with the volume of injection as 1 µL. The mass spectrometer was operated in electron-impact (EI) mode. Pre-column pressure: 80 KPa. Injection temperature: 250° C. Ion source: EI (200° C.). Interface temperature: 280° C. Electron energy: 70 eV. Solvent delay: 5.5 min. For qualitative analysis, the full scan mode (FSM) was used and the scan range was 40-400 m/z. For quantitative analysis (Bratu, A, et al., 2013), selective ion mode (SIM) was used, and m/z 79 was chosen as the ion fragment of EPA and DHA (Yi, T, et al., 2014).

Preparation of Standard Solutions:

The stock solutions of EPA methyl ester (2 mg/mL) and DHA methyl ester (2 mg/mL) were prepared in n-hexane and stored in the refrigerator. The working solutions were prepared by appropriate dilution of the stock solutions with n-hexane, and the resulting concentrations of were 10, 50, 100, 200, 400 and 800 µg/mL. DHA was prepared in serial dilutions of 50, 100, 200, 300, 400, 500 and 800 µg/mL. Calibration standard solution (1 µL) was injected for GC-MS analysis.

Preparation of Test Solution:

Preparation of Antioxidant Solution: Accurately weighed 0.5 mg of butylated hydroxytoluene was dissolved in 2,2, 4-trimethylpentane 10 ml to obtain a solution with a concentration of 0.05 mg per mL.

Experimental Procedure for Conversion of Fatty Acids to Fatty Acid Esters:

0.4/0.8 g for fish oil/fish oil microparticles sample was taken in a 10-mL volumetric flask and dissolved in isooctane, according to Table 8 below, in antioxidant Solution, and diluted with the same solution to make up the volume. 2.0 mL of this solution was transferred to a glass tube, and the solvent was evaporated under a gentle stream of nitrogen for approximately ~15 min. Then to this, 1.5 mL of a 2% (w/v) solution of sodium hydroxide in methanol was added, and the cap was tightly closed with a polytetrafluoroethylene-lined cap, mixed, and heated in a boiling water bath for 7 min. After cooling, 2 mL of boron trifluoride-methanol solution (120 g in 1000 mL of methanol) was added, covered with nitrogen, tightly caped, mixed, and heated in a boiling water bath for 30 min. Cooled to 40-50° C., and immediately added 1.0 ml of 2,2,4-trimethylpentane, capped, and mixed on a vortex mixer or shaken vigorously for at least 30 s. Immediately saturated sodium chloride solution 5 mL was added (containing 1 volume of sodium chloride and 2 volumes of water). [NOTE-Shake from time to time. Before using, the solution was decanted from any undissolved substance, and filtered if necessary.] Covered with nitrogen, capped, and mixed on a vortex mixer or shaken thoroughly for at least 15 s. Upper layer will become clear in the mixture, which was transferred to a separating funnel. The methanol layer was extracted one more time with 1.0 mL of 2,2,4-trimethylpentane, and the 2,2,4-trimethylpentane extracts were combined. Wash the combined extracts with two quantities, 1 mL each, of water, and dried over anhydrous sodium sulphate and finally diluted to 25 ml with 2,2,4-trimethylpentane and 1 µL was injected for GC-MS analysis.

TABLE 8

Amount of test substance to be weighed depending upon the EPA and DHA content

| Amount of Sample to Be Weighed (g) | Approx. Sum EPA + DHA |
|---|---|
| 0.4-0.5 | 30%-50% |
| 0.3 | 50%-70% |
| 0.25 | >70% |

Figure 5:
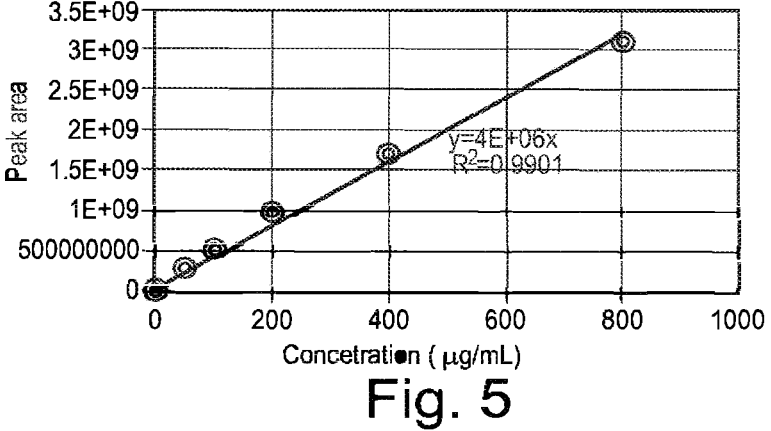
FIG. 5 shows a calibration graph for EPA ester standard.

FIG. 5 shows a calibration graph for EPA ester standard.

Figure 6:
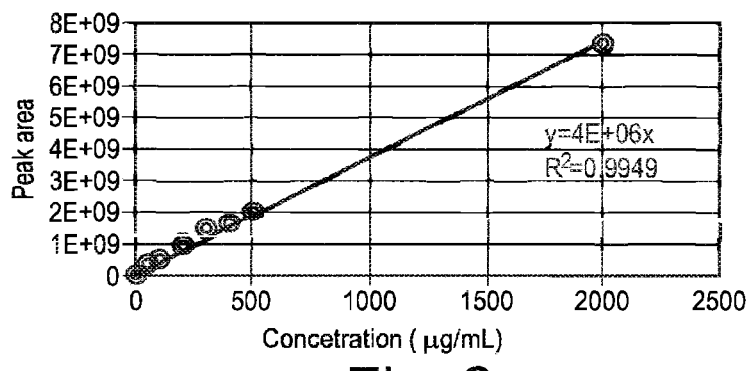
FIG. 6 shows a calibration graph for DHA ester standard.

FIG. 6 shows a calibration graph for DHA ester standard.

The calibration curves for EPA and DHA esters are given in FIG. 5 and FIG. 6 respectively. These curves were used for determination of EPA and DHA content in the fish oil and fish oil microparticles. The content of EPA and DHA obtained in the fish oil and fish oil microparticles is given in Tables 9 and 10. High encapsulation efficiency of EPA (96%) and DHA (98%) obtained for the fish oil microparticles.

TABLE 9

Peak area and amount of EPA in fish oil and fish oil microparticles.

| EPA | Fish oil | Fish oil microparticle |
|---|---|---|
| Actual amount (mg) | 5.20 | 5.00 |

TABLE 10

| Peak area and amount of DHA in fish oil and fish oil microparticles | | |
|---|---|---|
| DHA | Fish oil | Fish oil microparticle |
| Actual amount (mg) | 6.56 | 6.37 |

The Analytical Methods Used for Determination of Oxidative Degradation

The following standard tests were performed for identifying oxidation products in fish oil/fish oil microparticles:
P-Anisidine Value:

Scheme 1
Reaction of malonaldehyde with p-anisidine
in presence of acetic acid to form chromophore Malonaldehyde p-Anisidine p-Anisidine Chromophore The amount of non-volatile aldehydes (principally 2-alkenals) in the oils was measured using p-anisidine test, the AOCS official method for determining levels of the aldehydes (Lee, C, et al., 2001). The mechanism involves when the malonaldehyde reacted with p-anisidine (Tompkins, C, et al., 1999) in presence of acetic acid, it forms a chromophore through an intermediate as shown in above reaction. The absorbance of chromophore was measured at 350 nm in UV-visible spectrophotometry.

Preparation of Reagents for p-Anisidine Value

To test p-Anisidine value following two test solutions (A and B) are prepared.

Test Solution A—as per literature, the amount 0.50/1.00 g of test sample (fish oil or fish oil microparticle) substance to be examined was dissolved in isooctane, and diluted with the same solvent upto 25.0 mL. (For the fish oil microparticle, dispersed in 25 ml of isooctane and filtered and filtrate was used for the analysis)

Test Solution B—To 5.0 mL of Test Solution A, 1.0 ml of a 2.5 g/L solution of p-anisidine in glacial acetic acid was added, shaken, and stored protected from light.

Standard Solution—To 5.0 mL of isooctane 1.0 mL of a 2.5 g/L solution of p-anisidine in glacial acetic acid was added, shaken, and stored protected from light.

Experimental Procedure for the p-Anisidine Value

Initially measure the absorbance of Test Solution A at 350 nm using isooctane as the blank. Then measure the absorbance of Test Solution B at 350 nm exactly 10 min later its preparation (which needs to be kept under dark condition and with well closed lid), using the Standard Solution as the compensation liquid.

Formulae to Calculate the Anisidine Value from the Expression:

$$Result = [25 \times (1.2 A_S - A_B)]/m$$

$A_S$=absorbance of Test Solution B at 350 nm
$A_B$=absorbance of Test Solution A at 350 nm
m=weight of the substance to be examined in Test Solution A (g)

For example, p-anisidine value for fish oil $$Result = [25 * (1.2 A_S - A_B)]/m$$

$A_S$=absorbance of Test Solution B at 350 nm (1.01)
$A_B$=absorbance of Test Solution A at 350 nm (0.901)
Absorbance of Standard solution=0.07
m=weight of the substance to be examined in Test Solution A (g) (0.50 g)

$$Result = [25 * (1.2 * 1.01 - 0.901)] \div 0.5 = 5.675 \div 0.5$$

Figure 25:
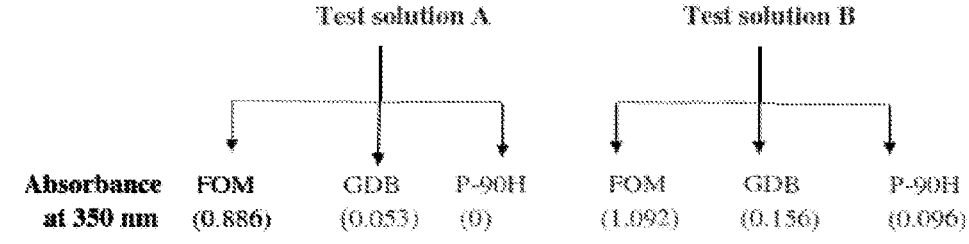
FIG. 25 shows a depiction of methods to test glyceryl dibehenate and phospholipon-90H as individual ingredients.

Therefore, P-Anisidine value (AV) of fish oil=11.35
P-Anisidine Value for Fish Oil Microparticles:

Fish oil microparticles (FOM) have extra ingredients such as glyceryl dibehenate (GDB) and Phospholipon (P-90H) along with fish oil. So, it's important to rule out the interference of these two materials (GDB and P-90H) to measure the actual PV of fish oil microparticles, therefore a method to test glyceryl dibehenate and phospholipon-90H as individual ingredients for test A and B was developed (FIG. 25).

TABLE 11

| P-anisidine value of fish oil and fish oil microparticles | |
|---|---|
| | P-anisidine value |
| Fish oil | 11.35 |
| Fish oil microparticles | 6.81 |
| Accepted range | 20 |

The p-anisidine value of fish oil and fish oil microparticles were in acceptable range (Table 11).

Peroxide Value

The peroxide value (Isamail, A, et al., 2016) is a parameter specifying the content of oxygen as peroxide, especially hydro peroxides in a substance. The peroxide value is a measure of the secondary oxidation present. ROOH is a hydro peroxide, one of the major initial oxidation products that decompose to form compounds responsible for off-flavors and odors. Such secondary products include hexanal, pentanal and malonaldehyde (shown below). This reaction scheme can generate aldehydes, ketones, alcohols and hydrocarbons. Many of the volatile compounds formed during lipid oxidation originate through similar dismutations.

Hexanal            Pentanal

Malonaldehyde

Experimental Procedure for Peroxide Value (Note: Carry out the operations avoiding exposure to actinic light)

Initially 5.0/10.0 g of test sample (Fish oil/Fish oil microparticles) was dissolved in 20.0 mL of isooctane and mixed it for 15 min, then filtered and the filtrate (20 ml) was mixed with 30 ml of glacial acetic acid (50 ml of a mixture of 2 volumes of trimethylpentane (Isoctane) and 3 volumes of glacial acetic acid) in a stoppered conical flask (protection from light necessary during the entire process). The substance in the flask was examined until it was dissolved. Using a suitable volumetric pipette, added 0.5 ml of saturated potassium iodide solution and replaced with the stopper. Allowed the solution to stand exactly for $60\pm1$ s, thoroughly shaking the solution continuously, then added 30 ml of water. Titrated the solution with 0.01 M sodium thiosulphate, adding it gradually and with constant, vigorous shaking, until the yellow iodine colour has almost disappeared. Add about 0.5 ml of starch solution (Mixed 1 g of soluble starch with sufficient cold water (=1 ml) to make a thin paste. Then thin paste was added, while stirring, to 100 mL of boiling water, and then cooled and used only the clear solution) and continue the titration, with constant shaking especially near the end-point, to liberate all the iodine from the solvent layer. Then added the sodium thiosulphate solution dropwise until the blue colour just disappears. Carry out a blank determination. If the result of the blank determination exceeds 0.1 ml of titration reagent, replace the impure reagents and repeat the determination. c=concentration of the sodium thiosulphate solution in moles, per litre.

$$\text{Fish oil} = [1000(4.0-0)\times0.01]/5.0 = 4.0 \text{ meq/kg}$$

$$GDB = [1000(1.0-0)\times0.01]/5.0 = 1.0 \text{ meq/kg}$$

$$\text{Microparticle} = [1000(5.5-0)\times0.01]/10.0 = 5.5 \text{ meq/kg}$$

$$\text{Peroxide Value} = 5.5-1.0 = 4.5$$

TABLE 12

| Peroxide value of fish oil and fish oil microparticles | |
| --- | --- |
| | Peroxide value (meq/Kg) |
| Fish oil | 4.0 |
| Fish oil microparticles | 4.5 |
| Accepted range | 0-12 |

The Peroxide value of fish oil and fish oil microparticle were in acceptable range (Table 12).

Total Oxidation Value (Totox)

Total Oxidation Value is Defined:

$$\text{Result} = 2PV + AV$$

PV=Peroxide Value

AV=Anisidine Value

The Totox value is calculated by the formula AV+2PV to indicate an oil's overall oxidation state. The lower the Totox value, the better the quality of oil.

| Fish oil $TOTOX$ | Fish microparticle $TOTOX$ |
| --- | --- |
| $\text{Result} = 2PV + AV$ | $= 2PV + AV$ |
| $= 2*4.0 + 11.35$ | $= 2*4.5 + 6.81$ |
| $= 8.0 + 11.35$ | $= 9 + 6.81$ |

TABLE 13

| TOTOX of fish oil and fish oil microparticles | |
| --- | --- |
| | TOTOX |
| Fish oil | 19.35 |
| Fish oil microparticles | 15.81 |
| Accepted range | 26 |

The TOTOX value of fish oil and fish oil microparticle were in acceptable range (Table 13).

Thiobarbituric Acid Reactive Substances (TBARS)

This is a by-product of lipid peroxidation. Lipid peroxidation is measured in the form of TBARS.

Scheme 2
Reaction of malonaldehyde with
2-thiobarbituric acid to form a chromophore -continued One molecule of MDA reacts with 2 molecules of 2-thio-barbituric acid via a Knoevenagel-type condensation (Scheme 2) to yield a chromophore with absorbance maximum at 538 nm.

Preparation of Reagents for TBARS Test (Ke, P and Woyewoda, A., 1979 and Kishida. E, et al. 1993):

0.04 M TBA stock solution: Dissolve 0.576 g of 2-thiobarbituric acid (TBA) in 10 ml of distilled water in a 100 ml volumetric flask and dilute to volume with glacial acetic acid, the reaction mixture kept for stirring for overnight covered with aluminium foil.

0.3 M $Na_2SO_3$ solution: Dissolve 1.891 gm of sodium sulphite in 50 ml distilled water.

0.1 M HCl (1 ml in 120 of distilled water)

0.01 M TEP stock solution: dissolve 0.11 g (119 μl) in 50 ml distilled water on a magnetic stirrer for 1 hr, and diluted TEP stock solution.

(0.01 M TEP) 119 μl in 50 ml distilled water—0.01 M TEP (Stock solution)

(0.01 M TEP) 1 mL in 10 ml distilled water—0.0001 M TEP (Work solution)

TBA work solution: 60 ml TBA stock solution, 40 ml chloroform, 5.0 ml sodium sulphate solution.

Standard curve: TEP Standard curve is based on 0.1 mM TEP work solution.

Followed the same procedure as sample analysis, only the oil is replaced by TEP work solution according to Table 14. For calibration graph, the following dilutions were prepared (Table 14).

TABLE 14

Standard stock solution 0.01M TEP and their dilutions

| μL TEP | 0 | 12.5 | 25 | 50 | 100 |
| μL H₂O | 200 | 187.5 | 75 | 150 | 100 |
| nmol TEP (nmol) | 0 | 1.25 | 2.5 | 5.0 | 10.0 |

TABLE 15

Standard stock solution 0.01M TEP stock solution to further dilutions (nmol/L)

| Concentration (nmol/L) | Absorbance (538 nm) |
|---|---|
| 0 | 0.149 |
| 1.25 | 0.273 |
| 2.5 | 0.459 |
| 5 | 0.801 |
| 10 | 1.334 |

FIG. 7 shows a calibration graph for MDA (0-10 nmol/mL).

The value of the slope is used in the calculations of TBARS values (FIG. 7).

Experimental Procedure

Weighed accurately±10 or 20 mg of oil/fish oil micropar-ticle into a short Kimax test tube. Added 5 mL TBA work solution and closed the tube tightly with a fitting cup. Mixed for 15 s on a vortex to dissolve the oil.

The tubes were incubated in a water bath with almost boiling water (95° C.) for 45 min; and the cooled down under running cold water. And then 2.5 mL 0.1 M HCl solution was added and mixed by inverting the tube a few times. Centrifuged for 10 min at 2500 rpm to separate the pink water phase from the chloroform phase (bottom). Then measured the absorbance of the water phase at 538 nm in 10 mm QS glass cuvettes against blank that was prepared as above, only without the oil.

To construct the standard curve as $A =$ $$f(n\ TEP) \Rightarrow y = ax + b.\ (Y = 0.1204x + 0.1518)$$

$$\text{Caluculation } \mu M\ TBARS/g\ \text{fat} = (A - b)/(a \times m \times 1000)$$

A=absorbance of the sample
a=slope of the standard curve (0.1204)
b=intercept of the standard curve (0.1518)
m=amount of the sample (g) (0.01 or 0.02 gm)
1000=conversion to μM/g

TABLE 16

TBARS values of fish oil and fish oil microparticles

| Samples | μM TBARS/g fat |
|---|---|
| Fish oil | 1.0 |
| Fish oil microparticle | 0.41 |

As similar to p-Anisidine value, peroxide value and TOTOX results, TBARS values also compared for fish oil and fish oil microparticle, the TBARS value of fish oil microparticle (0.41 μM TBARS/g fat) (Table 16) is much lower than the fish oil (1.0 UM TBARS/g fat). These results indicates that fish oil microparticle powders reduced the degradation. Higher the TBARS value greater the degradation.

$^1$H-NMR (Proton Nuclear Magnetic Resonance Spectra)

Proton NMR (Knothe, G and Kenar, J. A, 2004) is quite useful technique for structure identification of EPA and DHA acids, both molecules more or less similar except in the length of chain (EPA: $C_{20}H_{30}O_2$) and (DHA: $C_{22}H_{32}O_2$) number of double bonds (5 in EPA and 6 in DHA) (see structures below).

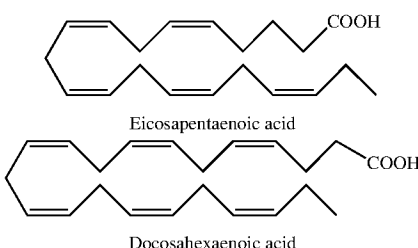

Eicosapentaenoic acid

Docosahexaenoic acid

Sample preparation: For $^1$H-NMR—about =4 mg of sample was dissolved in deuterated solvent chloroform (0.5 ml), transferred into NMR tube to run under 400 MHZ NMR machine which will take approximately 2 to 3 minutes to give a spectral data (FIG. 8)

FIG. 8 shows a proton NMR spectra, and spectral assignments, of fish oil showing both EPA and DHA peaks.

Based on literature values (Knothe, G and Kenar, J. A, 2004 and Haraldsson, G et al., 1995) and ${}^1$H-NMR spectra of fish oil corresponding peaks were identified the olefinic protons ($\delta$ 5.33-5.45 ppm), glycerol peaks at ($\delta$ 4.0-5.3 ppm), protons attached to the bis-allylic carbons ($\delta$ 2.72-2.88 ppm), protons attached to the allylic carbons ($\delta$ 2.0-2.1 ppm) and the terminal methyl group protons ($\delta$ 0.94-1.0 ppm) and the methylene ($CH_2$) protons at (1.72-1.65), (2.05-1.95) and (2.35-2.25) ppm.

${}^1$H-NMR (Expanded) Spectra to Show Presence of Aldehyde

Proton NMR is the useful tool to find out the structure of EPA and DHA ester molecules, from the literature we know that aldehyde which are secondary oxidation products such as propanal, decenal will have characteristic range of delta values which will come around 9 to 10 range. We took the NMR tool as an advantage to find out these aldehyde peaks of degradation products. Interestingly, the fish oil/fish oil microparticles do not have any corresponding aldehyde peaks of interest at $\delta$ 8-9.5 ppm, as shown in below FIG. 9 indicating absence of aldehyde compounds (secondary oxidation products).

Figures 9, 10:
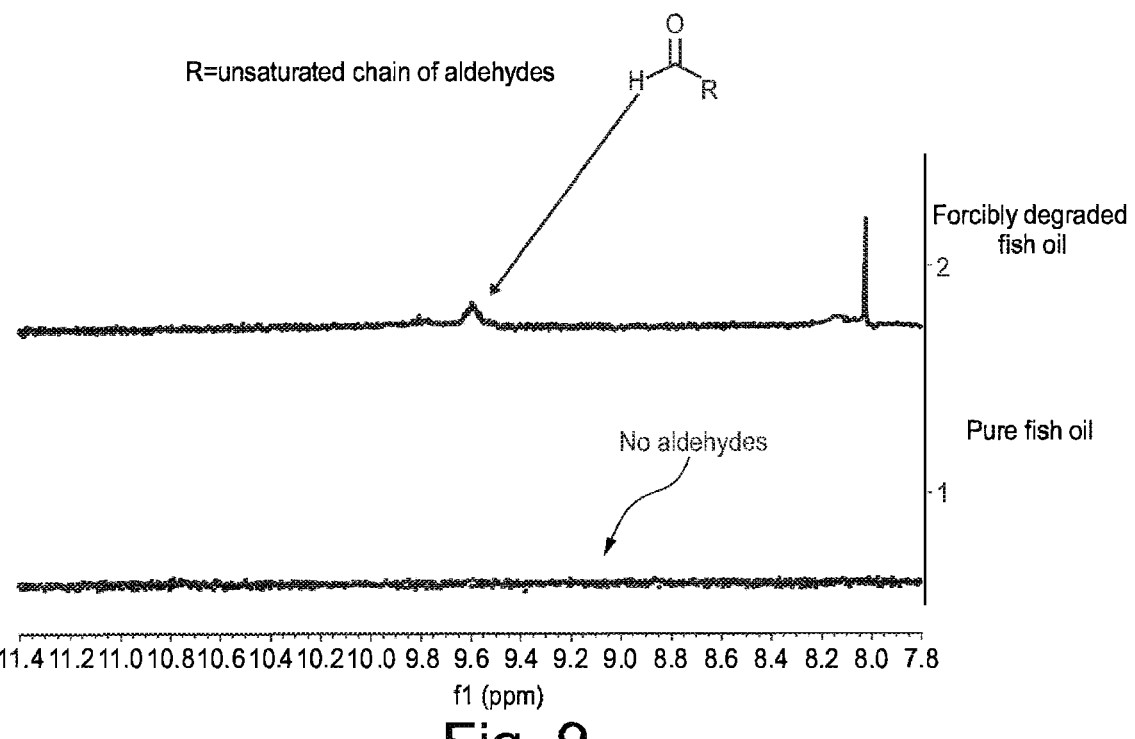
FIG. 9 shows an expanded proton NMR spectra of Fish oil to identify any aldehyde peaks.
FIG. 10 shows a complete proton NMR spectra of fish oil and forcibly degraded fish oil sample.

FIG. 9 shows an expanded proton NMR spectra of Fish oil to identify any aldehyde peaks.

To understand degradation pattern of fish oil, it was subjected to forcible degradation. A complete proton NMR spectrum of both fish oil and degraded fish oil and their comparison and notations is presented in FIG. 10.

FIG. 10 shows a complete proton NMR spectra of fish oil and forcibly degraded fish oil sample.

The comparative data of fish oil and forcibly degraded fish oil sample (FIG. 11), revealed some important identifications, signals of olefinic (J), bis-allylic (I) and n-3 methyl groups (B) decrease during the oxidation (forcibly degraded fish oil), as well as signals unique for DHA (H) and EPA (D), whereas signals for MUFA (allylic protons E) do not decrease.

GC-MS for Identification of Degradation Products:

As similar to NMR, GC-MS technique (L, Z. J. et al., 2013) was used to find out any secondary oxidation products (degradation products) aldehydes. We compared the fish oil, fish oil microparticle with forcibly degraded sample through GC-MS (FIG. 11).

Figure 11:
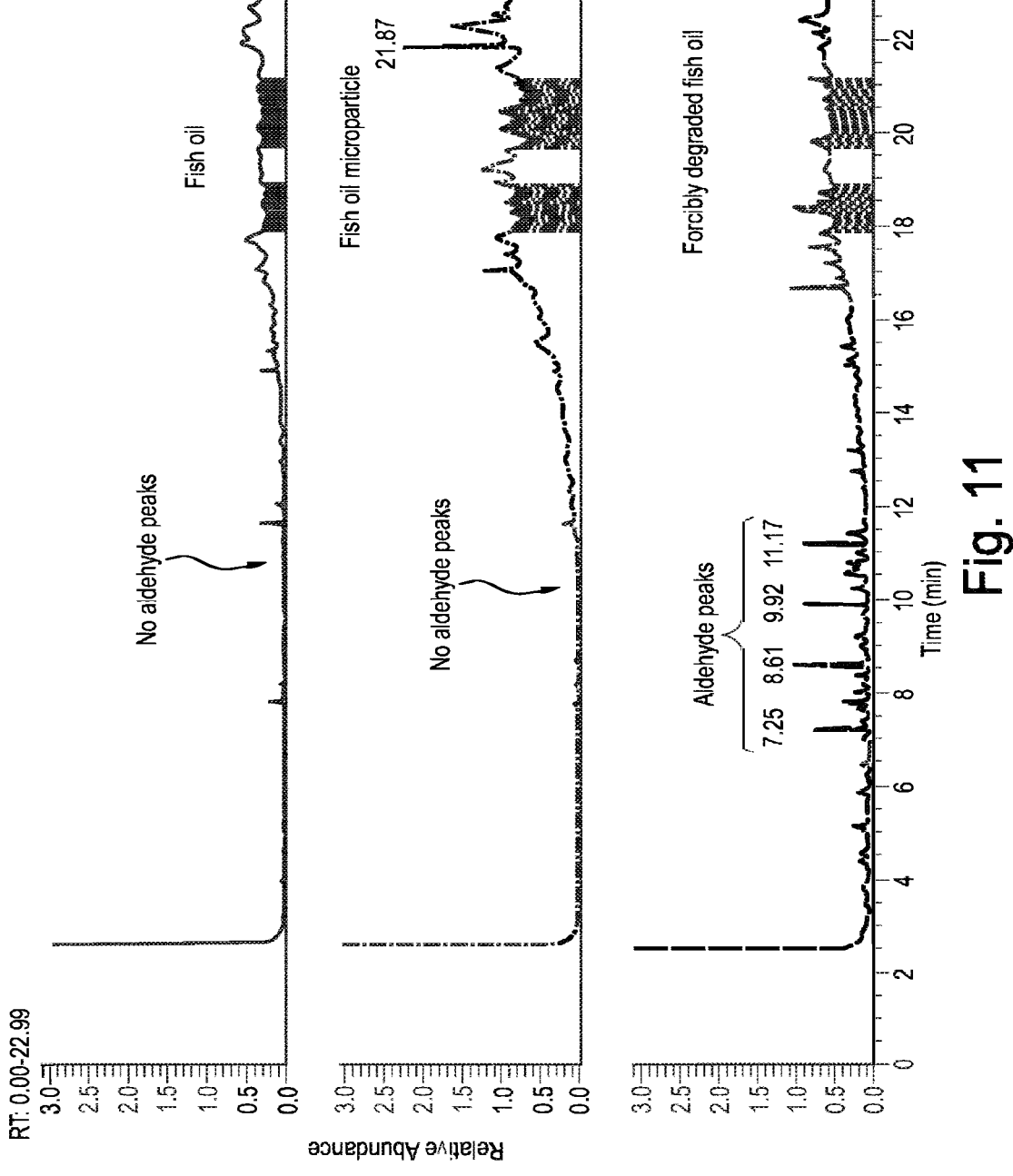
FIG. 11 shows a GC-MS comparison of fish oil, fish oil microparticle and forcibly degraded fish oil.

FIG. 11 shows a GC-MS comparison of fish oil, fish oil microparticle and forcibly degraded fish oil.

Forcibly degraded fish oil (i.e. exposure to light and oxygen) sample analysed by GC-MS showed some interesting peaks of secondary oxidation products such as 2-decenal, RT-7.25, 2-undecenal, 8.61, 9.92,2-dodecenal and tetradic-2-enal. Comparing GC-MS spectra of fish oil/fish oil microparticle with forcibly degraded fish oil sample, showed no aldehyde peaks at RT 7.25, 8.61, 9.92 and 11.17. This demonstrates that there is no secondary oxidation products in fish oil/fish oil microparticles.

Results

Stability Testing of Fish Oil and Fish Oil Microparticles:

Stability batch of fish oil microparticle (50:50 oil: GDB ratio) was prepared and subjected to stability studies. The fish oil microparticles were stored in amber coloured bottles at two storage conditions a. refrigeration (2-8° C.) and b. ambient temperature. The samples were withdrawn and analysed at 0, 1, 2, 4, 5, 6 months. The analysis was carried out for the following tests.

1. EPA and DHA content by GC-MS
2. P-Anisidine value
3. Peroxide value
4. TOTOX
5. TBARS
6. ${}^1$H-NMR EPA and DHA Content of Stability Batch of Fish Oil and Fish Oil Microparticles The stability batch has been analysed for quantification data of EPA and DHA and the results of each month data are shown below Table-17.

TABLE 17

| GC-MS Comparative stability data for six months of fish oil and fish oil microparticles | | | | |
|---|---|---|---|---|
| Time in | Fish Oil | | Fish Oil Microparticles | |
| Months | EPA (%) | DHA (%) | EPA (%) | DHA (%) |
| 0 | 100 | 100 | 100 | 100 |
| 1 | 97.5 | 98 | 99.8 | 100 |
| 2 | 97.5 | 92 | 100 | 97 |
| 4 | 92.5 | 84 | 96.8 | 92 |
| 5 | 80 | 89 | 83 | 90.5 |
| 6 | 40 | 36 | 81.6 | 94 |

From the comparative data of GC-MS quantification of fish oil, initial, first and second month, the amount of EPA is maintained (Table-17) but at the end of six months 60% decrease in EPA content (Table-17) was observed. Similarly for DHA there is gradual decrease in content of with time (64% loss or degradation at the end of six months) as observed in Table 17. Fish oil microparticles showed better stability in terms of both EPA and DHA content (Table-17). This strongly suggests that bioactive content of fish oil is more stable in microparticles than in free fish oil.

TABLE 18

| Comparative p-anisidine value data of fish oil and fish oil microparticles for six months | | |
|---|---|---|
| (Months) | P-Anisidine Value of fish oil | P-Anisidine Value Microparticle |
| 0 | 11.01 | 6.8 |
| 1 | 11.35 | 8.5 |
| 2 | 37.09 | 16.2 |
| 4 | 44 | 20 |
| 5 | 127.4 | 18.40 |
| 6 | 117.55 | 32.32 |

The comparative data of fish oil showed initial and first month the p-AV is quite stable (=11) and thereafter second and fourth month P-AV increases to higher value and further steep hike at fifth and sixth month (Table 18) which is not in the acceptable range (20). Fish oil microparticles demonstrated better stability with much lower increase in p-AV over the period of six months (Table 18).

Thus, comparative six months data for P-AV (Table 18) of fish oil and fish oil microparticles, confirms that fish oil microparticles are more stable with lesser formation of the secondary oxidation products (aldehyde).

TABLE 19

Comparative peroxide value data of fish oil
and fish oil microparticles for six months

| Peroxide Value | Fish oil | Fish oil microparticles |
|---|---|---|
| 0 | 4 | 4.5 |
| 1 | 4.5 | 5 |
| 2 | 7.5 | 5.5 |
| 4 | 10 | 6 |
| 5 | 15 | 9 |
| 6 | 20 | 12 |

TABLE 19.1

Standard accepted ranges of peroxide
values from European pharmacopeia-5

| Mass of substance to be examined (g) | Expected peroxide value |
|---|---|
| 2.00 to 5.00 | 0 to 12 |
| 1.20 to 2.00 | 12 to 20 |
| 0.80 to 1.20 | 20 to 30 |
| 0.500 to 0.800 | 30 to 50 |
| 0.300 to 0.500 | 50 to 90 |

Comparative data of six months for Peroxide Value of fish oil and fish oil microparticles, demonstrated better stability of fish oil microparticles with lower peroxide value indicating less degradation and lower amounts of secondary degradation products (Table-16).

TABLE 20

Comparative TOTOX value data of fish
oil and fish oil microparticles

| Months | TOTOX, Fish oil 2PV + AV | TOTOX, Microparticle 2PV + AV |
|---|---|---|
| 0 | 19 | 15.8 |
| 1 | 20.35 | 18.5 |
| 2 | 76 | 27 |
| 4 | 82 | 37 |
| 5 | 157 | 37 |
| 6 | 157 | 44.32 |

TOTOX values (Table 20) confirm the previous results with fish oil microparticles showing better stability as compared to fish oil at the end of six months.

TABLE 21

Comparative TBARS value data of fish
oil and fish oil microparticles.

| Months | TBARS Fish oil | TBARS Microparticle |
|---|---|---|
| 0 | 1.00 | 0.42 |
| 1 | 1.07 | 0.22 |
| 2 | 1.18 | 0.17 |
| 4 | 1.40 | 0.22 |
| 5 | 1.41 | 0.56 |
| 6 | 1.60 | 0.64 |

Comparative data of fish oil/fish oil microparticle (Table 21) showed low TBARS values for microparticles compared to fish oil. TBARS test values also confirms that less degradation products and indicating better stability for fish oil microparticles compared to fish oil.

Figure 12:
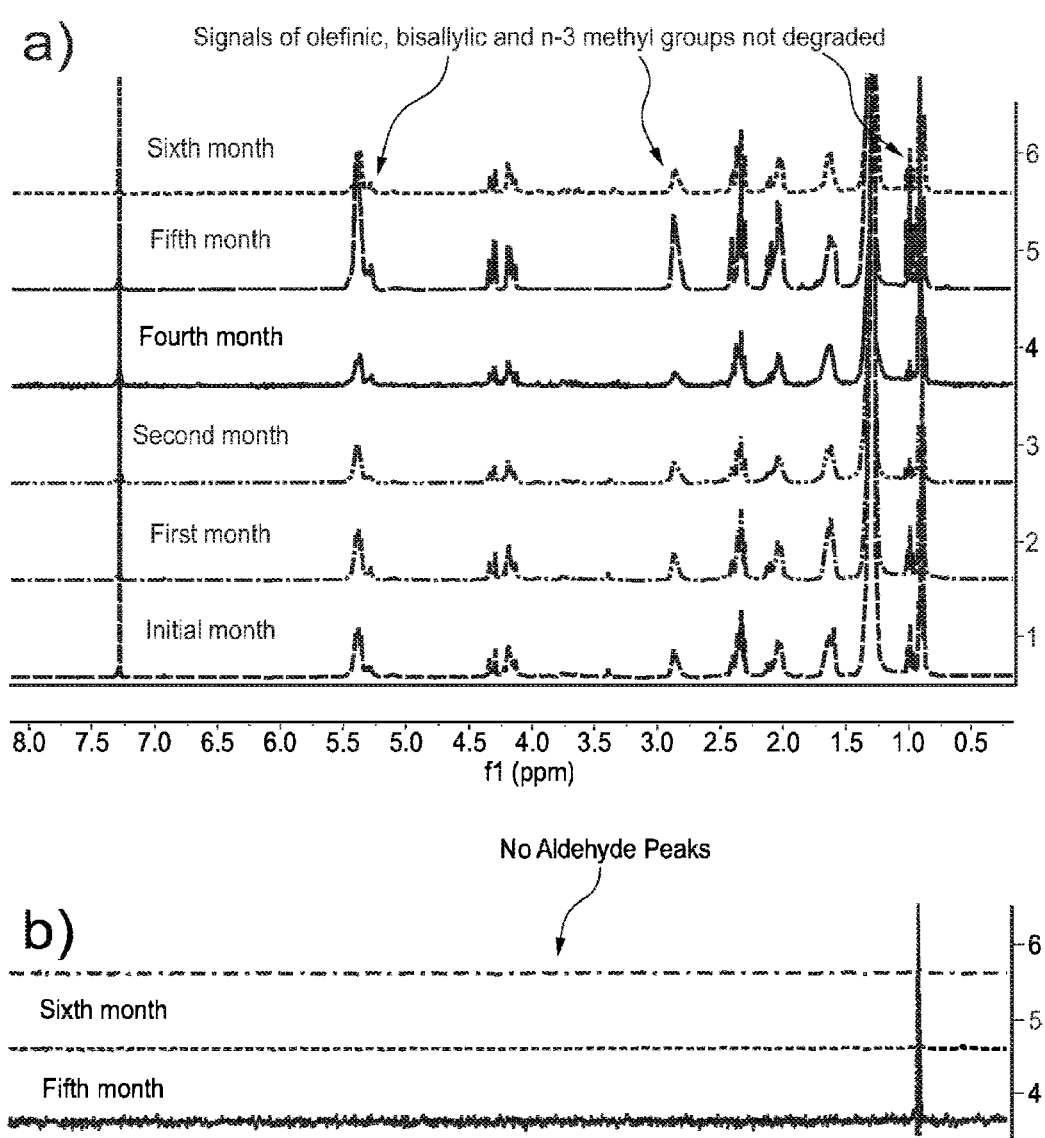
FIG. 12 shows several proton NMR spectra of fish oil taken over a six month period, both (a) full; and (b) expanded to show any aldehyde peaks.

FIG. 12 shows several proton NMR spectra of fish oil taken over a six month period, both (a) full; and (b) expanded to show any aldehyde peaks.

There is no identification of degradation products in full spectra of NMR (FIG. 12) of six months fish oil comparison and expansion spectra which are expected to form at 9-10 ppm and also there is no disappearance of peaks Signals of olefinic, bis-allylic and n-3 methyl groups.

FIG. 13 shows several proton NMR spectra of fish oil microparticles taken over a six month period, both (a) full; and (b) expanded to show any aldehyde peaks.

There is no identification of degradation products in full spectra of NMR of six months' fish oil microparticles (FIG. 13) comparison and expansion spectra which are expected to form at 9-10 ppm and also there is no disappearance of peak signals of olefinic, bis-allylic and n-3 methyl groups.

Figure 14:
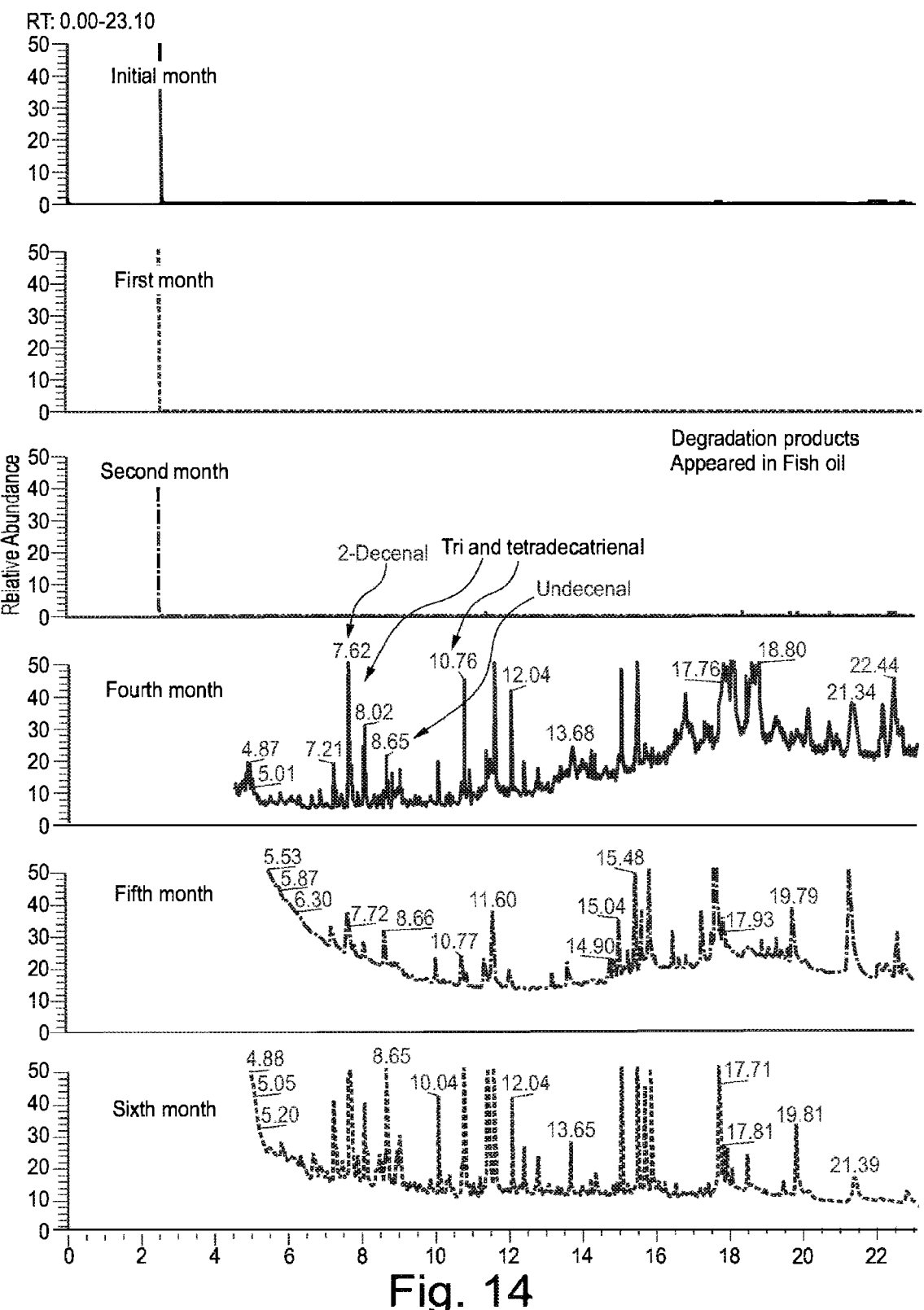
FIG. 14 shows GC-MS spectra and comparative data of fish oil microparticles over six months to identify degradation products.

FIG. 14 shows GC-MS spectra and comparative data of fish oil over six months to identify degradation products.

By GC-MS spectral data of fish oil, shows that after fourth month there is a secondary oxidation products (such as 2-decenal, tri and tetradecenal, and undecenal) aldehydes which continue to be there in fifth and sixth month spectra. The GC-MS spectra (FIG. 14) data confirms that fish oil started degrading after 4 months (which is also supporting to our stability test data of P-AV, peroxide value and TOTOX).

Figure 15:
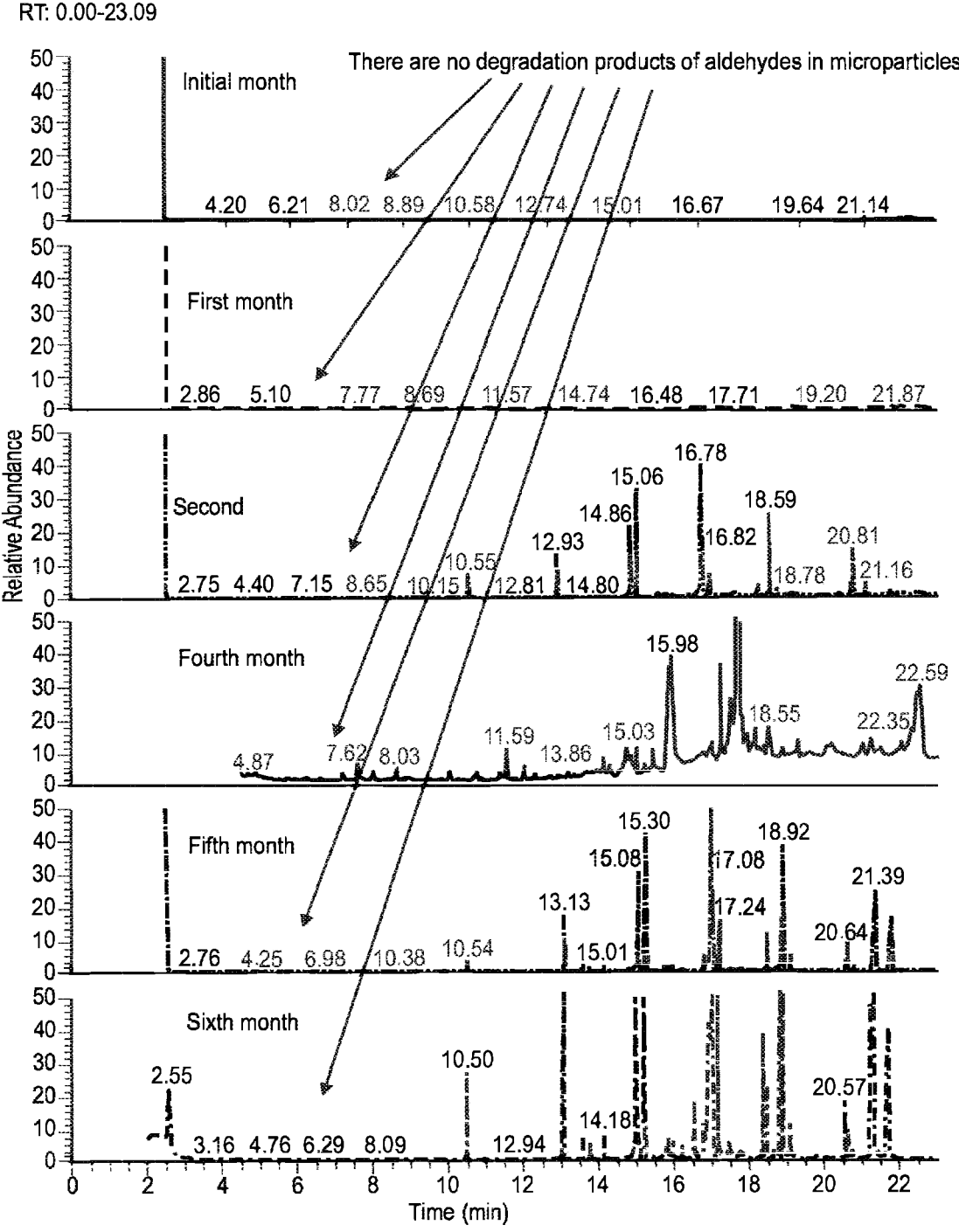
FIG. 15 shows GC-MS spectra and comparative data of fish oil over six months to identify degradation products.

FIG. 15 shows GC-MS spectra and comparative data of fish oil microparticles over six months to identify degradation products.

Comparative GC-MS spectral data (FIG. 15) of fish oil microparticles showed no secondary oxidation products (such as 2-decenal, RT-7.25,2-undecenal, 8.61 and 9.92, 2-dodecenal and tetradic-2-enal). This confirms that fish oil microparticles are more stable even after 6 months (which is supporting to our stability test results P-AV, peroxide value, TOTOX and TBARS tests). This data strongly confirms that oxidation is reduced (i.e. low secondary oxidation products) with respect to fish oil (GC-MS and Stability test data results).

Compared the NMR of fish oil microparticles formulation from technique 1 (FIG. 16A) and technique 2 (FIG. 16B), and both looks identical and no degradation of peaks of allylic and olefinic peaks (FIG. 16C).

Figure 17:
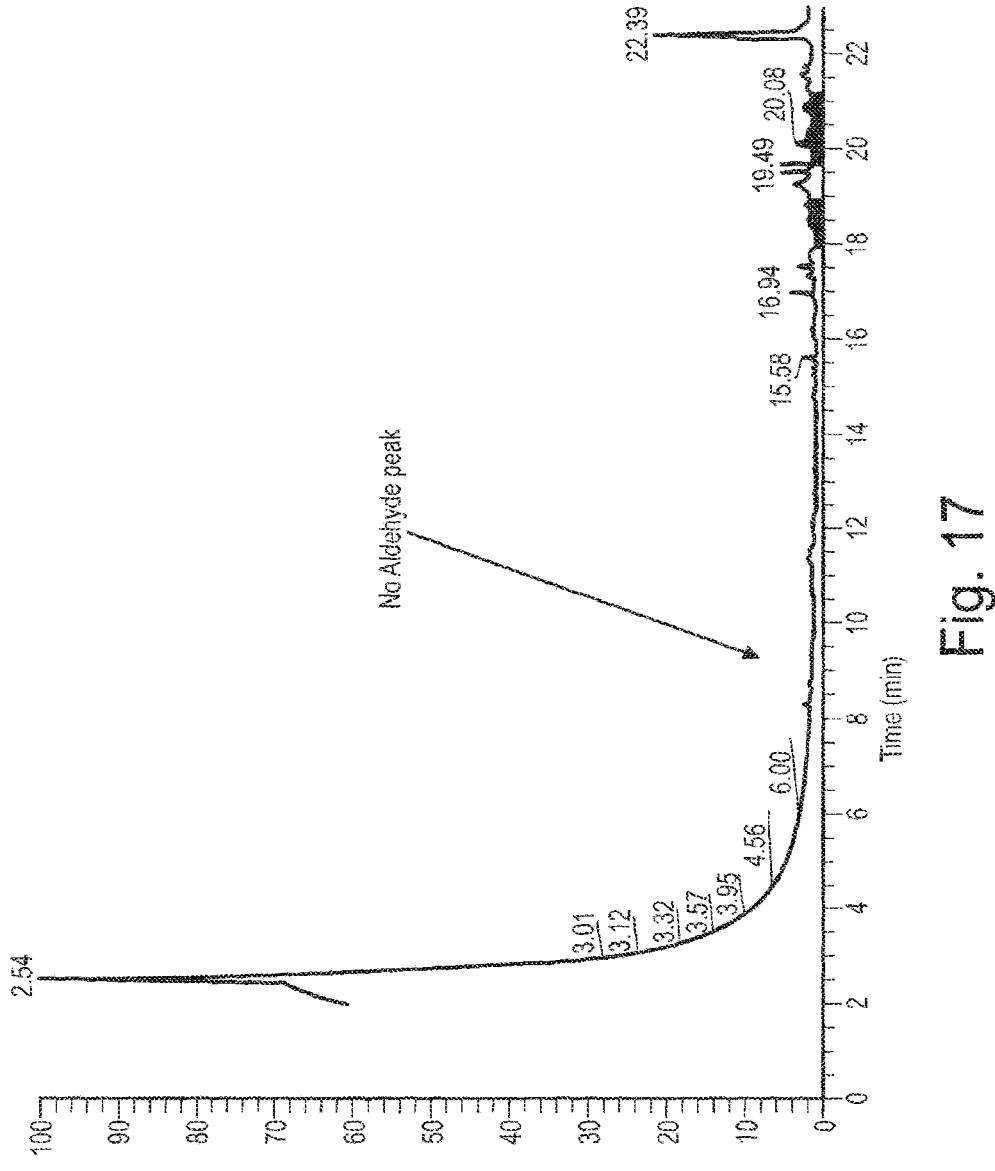
FIG. 17 shows GC-MS spectra of Fish oil microparticle (from extrusion).

FIG. 17 shows GC-MS spectra of Fish oil microparticle (from extrusion).

There is no degradation products (FIG. 17) (such as 2-decenal, RT-7.25, 2-undecenal, 8.61 and 9.92, 2-dodecenal and tetradic-2-enal) observed in GC-MS spectra of fish oil microparticle extruded from hot melt extrusion.

Data of microparticles characterisation is prepared extrusion (technique 2) is given below.

1. EPA and DHA Content by GC-MS:

| Fish oil | | Microparticles | |
| EPA (mg) | DHA (mg) | EPA (mg) | DHA (mg) |
|---|---|---|---|
| 5.6 | 6.6 | 5.3 | 6.56 |

2. P-Anisidine Value:

| P-Anisidine value | | TBARS | |
| Fish oil | microparticles | Fish oil | microparticles |
|---|---|---|---|
| 11.01 | 8.21 | 1.01 | 0.27 |

3. Particle Size:

| Average particle size of fish oil microparticles d(0.5) |
| --- |
| 30.537 |

Further testing performed upon the fish oil microparticles yielded the following results.

Figure 21:
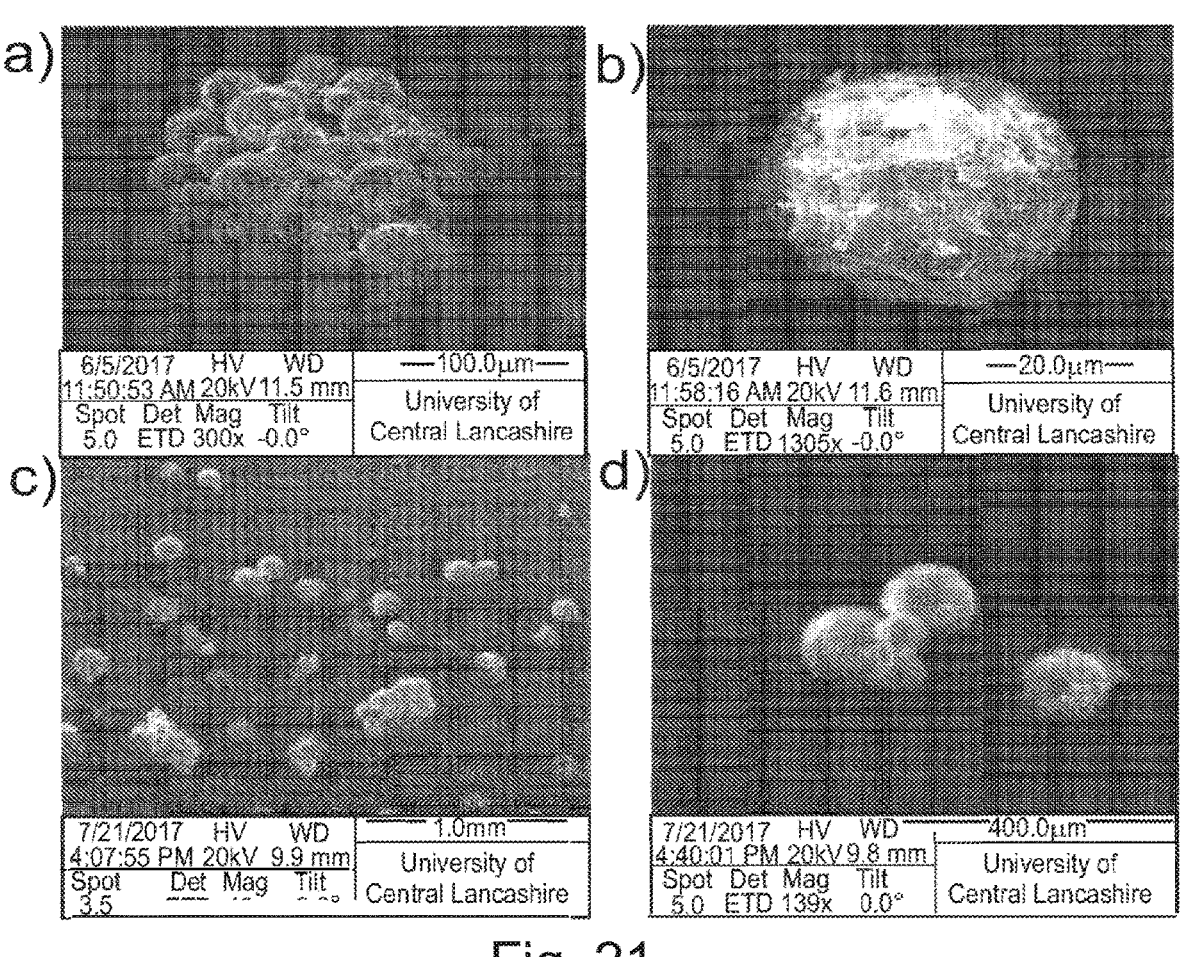
FIG. 21 Scanning Electron Microscopy images of a) microparticles and b) isolated image of microparticles c) Glyceryl dibehenate microparticles and d) isolated image of glyceryl dibehenate microparticles

Scanning Electron Microscopy:

FIG. 21 shows scanning electron microscope (SEM) images of: a) fish oil microparticles containing 50:50 fish oil and glyceryl behenate; b) an isolated fish oil microparticle containing 50:50 fish oil and glyceryl behenate; c) micropar-ticles of glyceryl behenate only; and d) isolated micropar-ticles of glyceryl behenate only.

SEM analysis shows that the fish oil microparticles have a particle size less than 100.0 μm. The SEM images of glyceryl behenate only (FIGS. 21c and 21d) clearly show that the surface of the "blank" particles are smooth. In contrast, the fish oil microparticles (FIGS. 21a and 21b) exhibit a surface morphology change, thereby clearly indi-cating that the fish oil is entrapped (or encapsulated) in the lipid matrix.

Differential Scanning Calorimeter (DSC)

Figure 22:
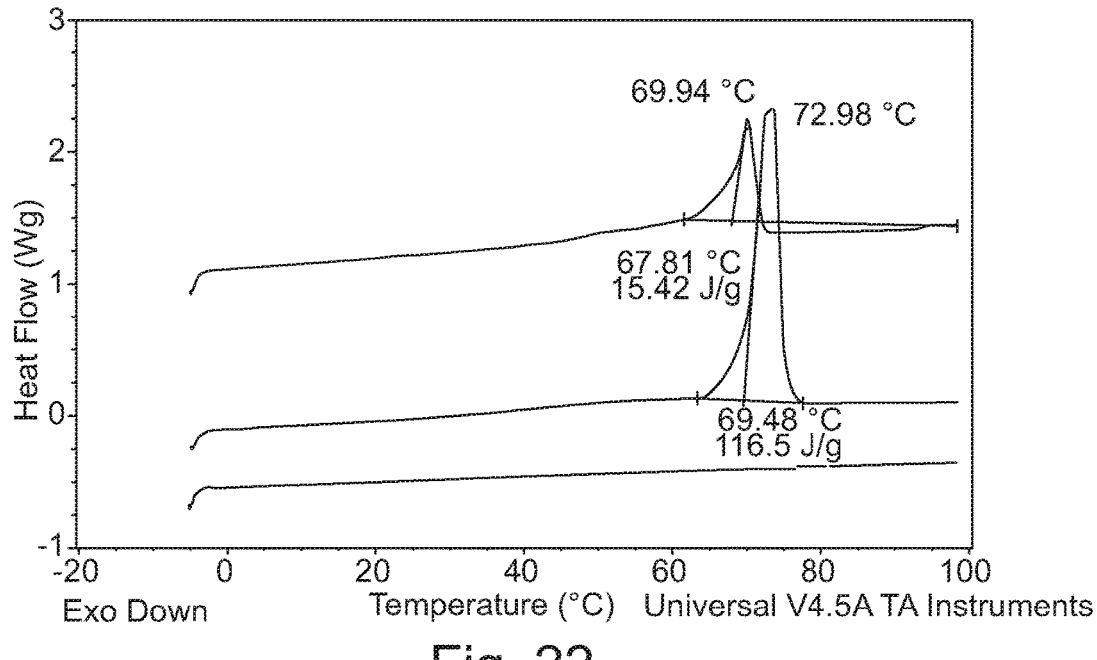
FIG. 22 shows a DSC of (Top to bottom): a) fish oil microparticles; b) bulk glyceryl dibehenate; and c) Fish oil.

FIG. 22 shows a DSC of (Top to bottom): a) fish oil microparticles; b) bulk glyceryl dibehenate; and c) Fish oil. In particular, FIG. 22 shows the thermal behaviour of fish oil, glyceryldibehenate, and fish oil microparticles.

The thermogram of pure fish oil being liquid did not exhibit any peak. The DSC thermogram of pure glycer-yldibehenate exhibited a sharp exothermic peak at about 72.98° C. Fish oil microparticle (FIG. 22) exhibited an exothermic peak at about 69.94° C. with a clear shift which is attributed to entrapment of fish oil in glyceryl dibehenate microparticles.

Figure 23:
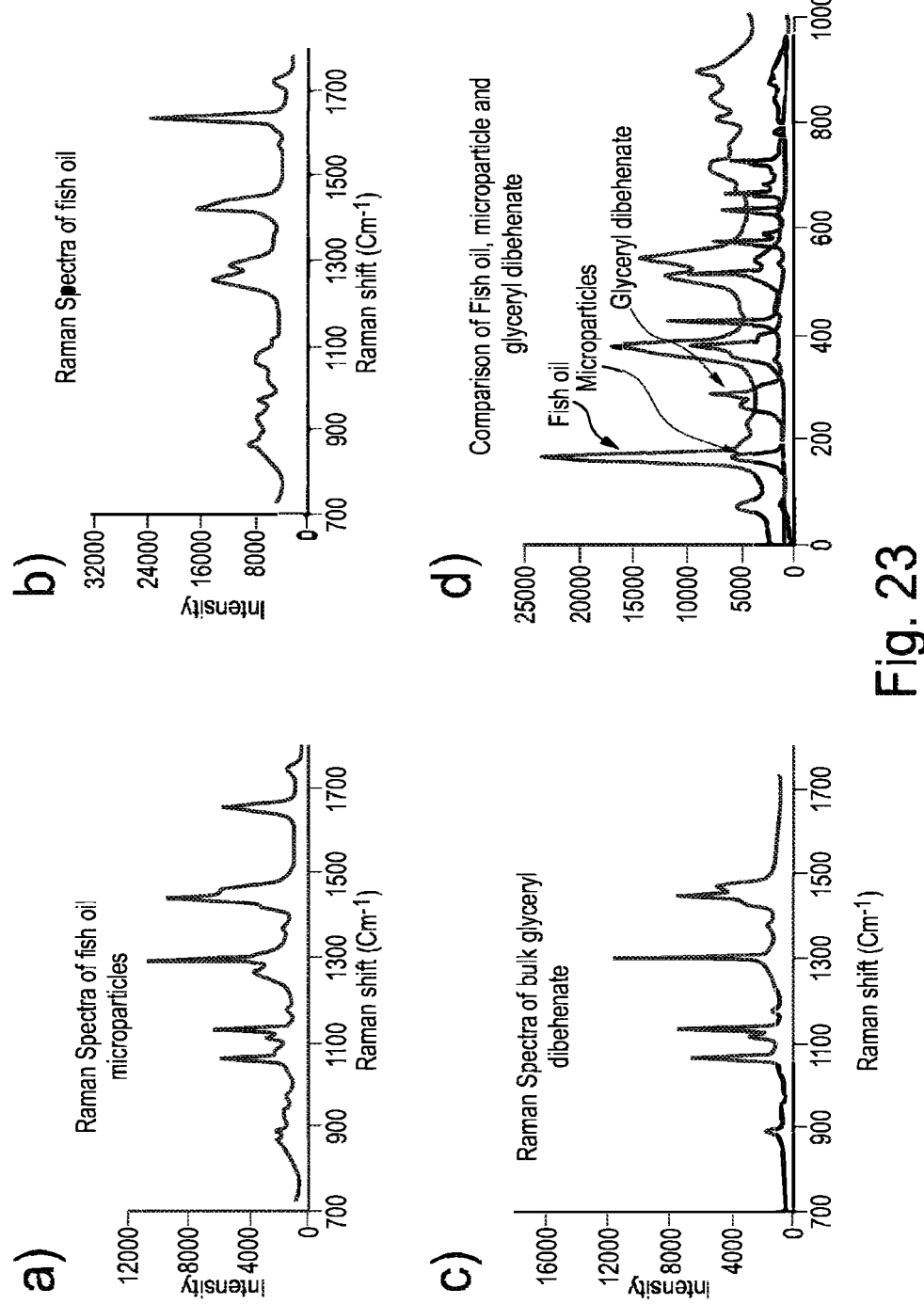
FIG. 23 shows Raman spectra for pure a) microparticles b) fish oil c) glyceryl dibehenate and d) comparison of microparticle, fish oil and glyceryl dibehenate.

Raman Spectroscopy:

FIG. 23 shows Raman spectra for pure a) microparticles b) fish oil c) glyceryl dibehenate and d) comparison of microparticle, fish oil and glyceryl dibehenate.

The finger print region i.e 1657 cm$^{-1}$ peak corresponds to v (C═C), peak broadening strongly indicates that double bonds of EPA and DHA in both microparticles (FIG. 23a) and fish oil (FIG. 23b). Both strong peaks (FIG. 23d) at 1062 and 1130 cm$^{-1}$ indicates the v (C—C) the presence of EPA and DHA along with glyceryl dibehenate in microparticles confirming the entrapment of fish oil in glyceryl dibehenate.

X-Ray Diffraction:

FIG. 24 shows XRD traces for pure a) bulk glyceryl dibehenate b) microparticles c) comparison of micropar-ticles and bulk glyceryl dibehenate to facilitate analysis of fish oil microparticle and glyceryl dibehenate samples by X-ray diffractometer.

The XRD pattern of Glyceryl dibehenate (FIG. 24a) contains two characteristic peaks at 21.43 and 23.74° 2θ. Further the glyceryl dibehenate characteristic peaks has shifted quite significantly from 21.43 to 21.20 in the microparticle (FIGS. 24b and c) which strongly indicates that the microparticles comprise fish oil encapsulated within glyceryl dibehenate.

The non-encapsulated oil (surface oil) was determined by mass difference between the initial clean flask and that containing the extracted oil residue. Seven millitres of hexane were added to 1.5 gm of microparticles in a glass jar with a lid, which was shaken by hand for the extraction of free oil, during 1 min, at room temperature. The mixture was filtered through a Whatman filter paper no. 1 and the filtered powder was collected on the filter paper. Then, the solvent was left to evaporate at room temperature and after drying heated at 60° C., until constant weight was obtained. The non-encapsulated oil (surface oil) was determined by mass difference between the initial clean flask and that containing the extracted oil residue.

The non-encapsulated oil (surface oil) of the microparticle is less than 10%.

Example 4—Formulation of Drug-Containing "Solid Oils" Using Hot-Melt Extrusion

The following experiments involve production of extruded solids (lipid/oil mixtures) containing a drug which is mixed in the oil before it is mixed with solid lipid prior to extrusion. This demonstrates that the present invention can be used to produce drug formulations containing relatively hydrophobic drugs.

Preparation Procedure Involving Incorporation of Solid Drug (Ascorbyl Palmitate) within Oil (Olive Oil) and Glyc-eryl Behenate Matrix Composition (50%, 8 gm): Olive oil (43.75%, 7 gm): Ascorbyl palmitate (6.25%, 0.5 g). Before performing hot melt extrusion process, 3.5 g of olive oil and added 0.5 g of Ascorbyl palmitate taken in a flask and heated on a hot water bath at 80° C. to disperse the drug Ascorbyl palmitate for 5 minutes.

Initial temperature was maintained at 25° C. and GDB and drug loaded olive oil mixture (4 g of mixture (olive oil+ Ascorbyl palmitate)) were fed into the feeding zone over the period of 5 min (for an 8.0 g batch) feeding 1.0 g drug loaded olive oil mixture and 1.0 g of GDB alternatively. Whilst feeding, the rate of screw speed was increased step wise from 0.0 to 40.0 rpm to ensure uniform mix. After the feeding was complete, the temperature was increased to 60° C. (extrusion temperature) to obtain solid extrudates with immediate solidification at the die exit. The extrudates were milled to yield free flowing powder.

Figure 18:
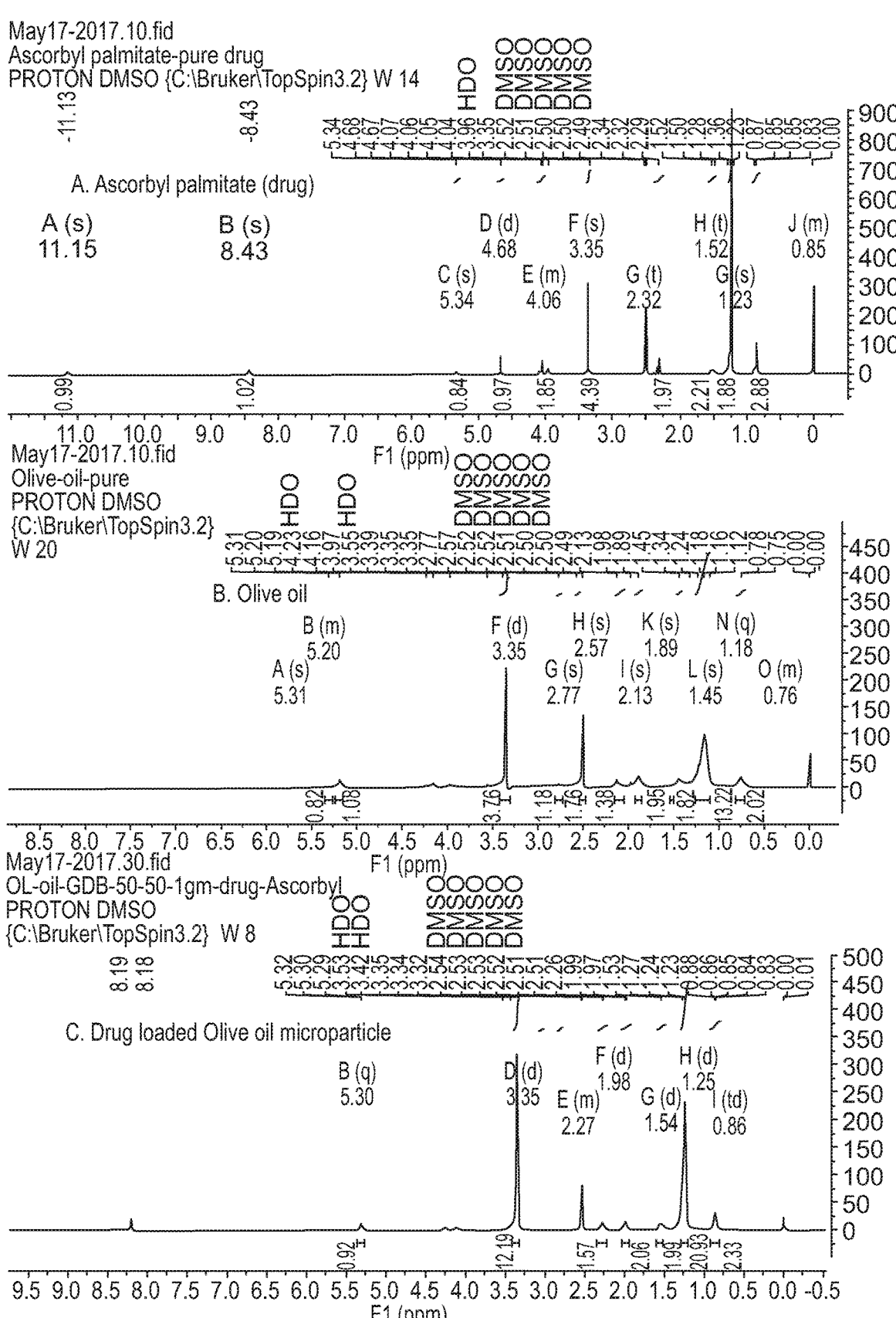
FIG. 18 shows 1H NMR spectra for A—Ascorbyl palmitate (model drug); B—Olive oil; and C—drug-loaded olive oil microparticle.

The chemical structures of ascorbyl palmitate and a general triglyceride (predominant species in olive oil) are shown below:

FIG. 18 shows 1H NMR spectra for A—Ascorbyl palmi-tate (model drug); B—Olive oil; and C—drug-loaded olive oil microparticle.

Figure 19:
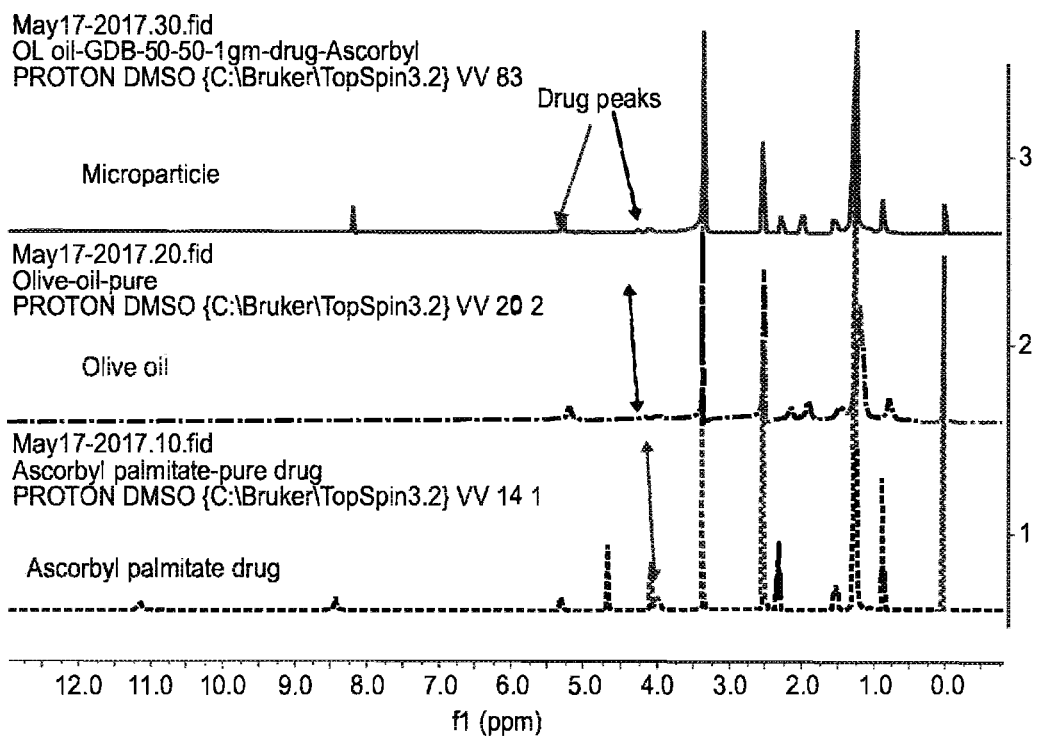
FIG. 19 shows comparisons between 1H NMR spectra of microparticles containing with Ascorbyl palmitate, olive oil and Ascorbyl palmitate.

FIG. 19 shows comparisons between 1H NMR spectra of microparticles containing with Ascorbyl palmitate, olive oil and Ascorbyl palmitate.

The comparative NMR spectra depicted in FIGS. 18 and 19 show that drug, ascorbyl palmitate, is present in the formulation and significant peaks were correlated with the pure NMR of Ascorbyl palmitate and olive oil.

Figure 20:
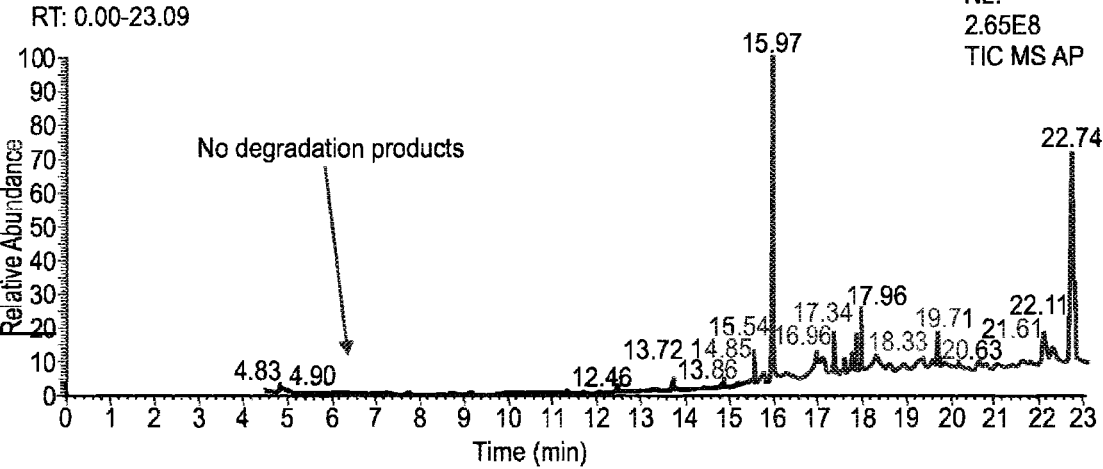
FIG. 20 shows a GC-MS trace of solid lipid microparticle with drug no degradation products.

FIG. 20 shows a GC-MS trace of solid lipid microparticle with drug no degradation products.

GC-MS spectra of drug loaded lipid microparticle showed no aldehyde peaks indicating no degradation using hot melt extrusion technique.

REFERENCES

1. Aghbashlo M, Mobli H, Madadlou A, Rafiee S. Integrated optimization of fish oil microencapsulation process by spray drying. J Microencapsul (2012) 29:790-804.
2. Annamalai, J.; Dushyant, C.; Gudipati, V., Oxidative stability of microencapsulated fish oil during refrigerated storage. Journal of Food Processing and Preservation 2015, 39 (6), 1944-1955.
3. Bhandari, B. R.; D'Arcy, B. R.; Padukka, I. Encapsulation of lemon oil by paste method using b-cyclodextrin: Encapsulation efficiency and profile of oil volatiles. Journal of Agricultural and Food Chemistry 1999, 47, 5194-5197.
4. Bao S S, Hu X C, Zhang K, Xu X K, Zhang H M, Huang H. Characterization of spray-dried microalgal oil encapsulated in cross-linked sodium caseinate matrix induced by microbial transglutaminase. J Food Sci (2011) 76: E112-8.
5. Beir~ao da Costa S, Duarte C, Bourbon A I, Pinheiro A C, Janu'ario MIN, Vicente A A, Beir~ao-da-Costa M L, Delgadillo I.; Inulin potential for encapsulation and controlled delivery of Oregano essential oil. Food Hydrocolloids (2013) 33:199-206.
6. Beristain, C. I.; Garcia, H. S.; Vernon-Carter, E. J. Spray-dried encapsulationof cardamom (Elletaria cardamomum) essential oil withmesquite (Prosopis juliflora) gum. Lebensm. Wiss. Technologie 2001, 34, 398-401
7. Che Man, Y. B.; Irwandi, J.; Abdullah, W. J. W. Effect of different types of maltodextrin and drying methods on physico-chemical and sensory properties of encapsulated durian flavour. Journal of the Science of Food and Agriculture 1999, 79, 1075-1080.
8. Choe, E.; Min, D. B., Mechanisms and factors for edible oil oxidation. Comprehensive reviews in food science and food safety 2006, 5 (4), 169-186.
9. Gulotta, A.; Saberi, A. H.; Nicoli, M. C.; McClements, D. J., Nanoemulsion-Based Delivery Systems for Polyunsaturated (w-3) Oils: Formation Using a Spontaneous Emulsification Method. Journal of Agricultural and Food Chemistry 2014, 62 (7), 1720-1725.
10. Heinzelmann K, Franke K, Velasco J, Marquez-Ruiz G. 2000a. Microencapsulation of fish oil by freeze-drying techniques and influence of process parameters on oxidative stability during storage. Eur Food Res Technol 211:234-9.
11. Huang H, Hao S, Li L, Yang X, Cen J, Lin W, Wei Y. Influence of emulsion composition and spray-drying conditions on microencapsulation of tilapia oil. J Food Sci Technol (2014) 51:2148-54
12. Ismail, A.; Bannenberg, G.; Rice, H. B.; Schutt, E.; Mackay, D., Oxidation in EPA- and DHA-rich oils: an overview. Lipid Technology 2016, 28 (3-4), 55-59.
13. Ke, P.; Woyewoda, A., Microdetermination of thiobarbituric acid values in marine lipids by a direct spectrophotometric method with a monophasic reaction system. Analytica Chimica Acta 1979, 106 (2), 279-284.
14. Kishida, E.; Tokumaru, S.; Ishitani, Y.; Yamamoto, M.; Oribe, M.; Iguchi, H.; Kojo, S., Comparison of the formation of malondialdehyde and thiobarbituric acid-reactive substances from autoxidized fatty acids based on oxygen consumption. Journal of agricultural and food chemistry 1993, 41 (10), 1598-1600.
15. Kim, Y. D.; Morr, C. V. Microencapsulation properties of gum arabic and several food proteins: Spray-dried orange oil emulsion particles. Journal of Agricultural and Food Chemistry 1996, 44, 1314-1320.
16. Knothe, G.; Kenar, J. A., Determination of the fatty acid profile by 1H-NMR spectroscopy. European Journal of Lipid Science and Technology 2004, 106 (2), 88-96.
17. Lee, C.; Zhou, B.; Bansal, G., Determination of the Aldehyde Levels in Frying Oil Using p-Anisidine Test. Journal of the American Oil Chemists' Society 2001, 76, 945-947.
18. Leimann F V, Goncalves O H, Machado R A F, Bolzan A. Antimicrobial activity of microencapsulated lemongrass essential oil and the effect of experimental parameters on microcapsules size and morphology. Mater Sci Eng C-Biomimetic Supramol Syst (2009) 9:430-6
19. Liu, X. D.; Atarashi, T.; Furuta, T.; Yoshii, H.; Aishima, S.; Ohkawara, M.; Linko, P. Microencapsulation of emulsified hydrophobic flavors by spray drying. Drying Technology 2001, 19, 1361-1374.
20. McLennan P L, Abeywardena M Y. Membrane basis for fish oil effects on the heart: linking natural hibernators to prevention of human sudden cardiac death. J Membr Biol (2005) 206:85-102.
21. Mezzenga, R.; Ulrich, S., Spray-dried oil powder with ultrahigh oil content. Langmuir 2010, 26 (22), 16658-16661.
22. Partanen, R.; Ahro, M.; Hakala, M.; Kallio, H.; Forssell, P. Microencapsulation of caraway extract in b-cyclodextrin and modified starches. European Food Research and Technology 2002, 214, 242-247.
23. Pathak, S., Acid catalyzed transesterification. Journal of Chemical and Pharmaceutical Research 2015, 7 (3), 1780-1786.
24. Rubilar M, Morales E, Saez R, Acevedo F, Palma B, Villarroel M, Shene C. Polyphenolic fractions improve the oxidative stability of microencapsulated linseed oil. Eur J Lipid Sci Technol (2012) 114:760-71.
25. Rosiaux, Y. Desvignes, F. Marchaud, D. Fundamental Differences in Hot Melt Extrusion with Polymers and Solid Lipid Excipients. AAPS, Poster 2015
26. Soliman E A, El-Moghazy A Y, El-Din M S M, Massoud M A. 2013. Microencapsulation of essential oils within alginate: formulation and in vitro evaluation of antifungal activity. J Encapsulat Adsorp Sci 3:48-55.
27. Sun-Waterhouse D, Zhou J, Miskelly G M, Wibisono R, Wadhwa S S. Stability of encapsulated olive oil in the presence of caffeic acid. Food Chem (2011) 126:1049-56.
28. Tur, J. A.; Bibiloni, M. M.; Sureda, A.; Pons, A., Dietary sources of omega 3 fatty acids: public health risks and benefits. British Journal of Nutrition 2012, 107 (S2), S23-S52.
29. Wan Y T, Bankston J D, Bechtel P J, Sathivel S. Microencapsulation of menhaden fish oil containing soluble rice bran fiber using spray drying technology. J Food Sci (2011) 76: E348-56.
30. Wang R X, Tian Z G, Chen L Y. A novel process for microencapsulation of fish oil with barley protein. Food Res Int (2011) 44:2735-41.
31. Weitz D, Weintraub H, Fisher E, Schwartzbard A Z. 2010. Fish oil for the treatment of cardiovascular disease. Cardiol Rev 18:258-63.

32. Xiao Z B, Liu W L, Zhu G Y, Zhou R J, Niu Y W. 2014. Production and characterization of multinuclear micro-capsules encapsulating lavender oil by complex coacer-vation. Flavor Fragrance J 29:166-72.

33. Yilmaz, G.; Jongboom, R.; Feil, H.; Hennink, W., Encapsulation of sunflower oil in starch matrices via extrusion: effect of the interfacial properties and process-ing conditions on the formation of dispersed phase mor-phologies. Carbohydrate polymers 2001, 45 (4), 403-410.

The invention claimed is:

1. A method of preparing a free flowing particulate solid composition, the method comprising:

forming a particulate dispersion or suspension by mixing together an oil component comprising one or more oils; a lipid component comprising one or more lipids; and an aqueous phase optionally comprising a surfactant;

isolating, from the particulate dispersion or suspension, free-flowing solid oil-loaded microparticles having an average particle size between 20 and 500 μm; and wherein:

the isolated free-flowing solid oil-loaded microparticles comprise at least 10 wt % oil component co-mixed with at least 20 wt % lipid component, and the combination of the oil component and the lipid component consti-tutes at least 80 wt % of the total weight of the isolated free-flowing solid oil-loaded microparticles;

the oil component is a liquid at standard ambient tempera-ture and pressure (SATP);

the lipid component and the solid composition are each independently solid at SATP; and the lipid component has a melting point greater than or equal to 50° C. or the lipid constituting the largest proportion of the lipid component has a melting point greater than or equal to 50° C.

2. The method of claim 1, wherein the oil component comprises one or more organic oils selected from animal oils, vegetable oils, and/or essential oils.

3. The method of claim 1, wherein the lipid component comprises one or more fatty acid glycerides.

4. The method of claim 3, wherein at least 70 wt % of the lipid component consists of one or more fatty acid glycer-ides derived from one or more fatty acids.

5. The method of claim 3, wherein at least 40 wt % of the one or more fatty acid glycerides is/are derived from a single C_{14}-C_{28} saturated or unsaturated fatty acid.

6. The method of claim 1, wherein the lipid component comprises a phospholipid.

7. The method of claim 6, wherein at most 5 wt % of the lipid component is phospholipid.

8. The method of claim 1, wherein the solid composition is free of water-soluble surfactants.

9. The method of claim 1, wherein the solid composition is an orally-administrable solid composition.

10. The method of claim 1, wherein the solid composition comprises isolated oil-loaded microparticles having an aver-age particle size between 70 and 300 μm, wherein each of the oil-loaded microparticles comprises an oil component, present at a concentration of at least 10 wt %, co-mixed with a lipid component, present at a concentration of at least 20 wt %, such that the oil component and the lipid component are present in a respective weight ratio of between 10:90 and 60:40.

11. The method of claim 1, wherein:

a single lipid constitutes at least 50 wt % of the total weight of the lipid component; or at least 50 wt % of the lipid component consists of one or more fatty acid-based lipids derived from one or more fatty acids, wherein a single fatty acid constitutes at least 50 wt % of the total weight of fatty acid(s) present within the one or more fatty acid-based lipids.

12. The method of claim 1, wherein the solid composition further comprises a nutraceutical ingredient or a pharma-ceutically active ingredient.

13. The method of claim 12, wherein the nutraceutical ingredient or a pharmaceutically active ingredient is pre-mixed with the oil component.

14. The method of claim 1, wherein the oil component has a kinematic viscosity between 10 and 500 cSt at SATP.

15. The method of claim 1, wherein the one or more organic oils comprises a marine oil.

16. The method of claim 15, wherein the one or more organic oils comprises one or more omega-3 fatty acids or omega-3 fatty acid esters.

17. The method of claim 1, wherein the solid composition comprises less than 15 wt % surface oil.

18. The method of claim 1, wherein the solid composition is incorporated within a tablet.

19. The method of claim 1, wherein the oil component and the lipid component are present in a respective weight ratio of between 10:90 and 60:40.

20. The method of claim 1, wherein the lipid component is in its melted state during the mixing together.

21. The method of claim 1, wherein forming a particulate dispersion or suspension comprises mixing together the oil component and the lipid component to form an oil-lipid mixture and thereafter mixing the oil-lipid mixture with a pre-heated aqueous phase to produce an aqueous dispersion.

22. The method of claim 21, wherein the pre-heated aqueous phase is pre-heated at or above the melting point of the lipid component.

23. The method of claim 21, wherein the pre-heated aqueous phase comprises poloxamer 188.

24. The method of claim 21, further comprising cooling the aqueous dispersion to produce the particulate dispersion or suspension.

25. The method of claim 24, wherein the aqueous disper-sion is agitated for at least 2 minutes following its formation, after which the aqueous dispersion is cooled to a tempera-ture at or below 20° C. while being agitated.

26. The method of claim 1, wherein particles of solid composition are separated from the particulate dispersion or suspension via filtration, whereafter the particles of solid composition are collected.

27. The method of claim 1, wherein the degree of encap-sulation, relative to the method's input ingredients, is greater than or equal to 40%, where degree of encapsulation is calculable via the equation:

$$D_e = \frac{E_o}{I_o}$$

where $D_e$ is the degree of encapsulation, which can be expressed as a percentage by multiplying by 100, $E_o$ is the weight of the oil component encapsulated within the solid composition product, and $I_o$ is the input weight of the oil component.

28. A free flowing particulate solid composition obtained by the method of claim 1.

29. A method of preparing an oil-containing product, the method comprising either:

a) incorporating the solid composition of claim 28 within a product; or b) transforming the solid composition of claim 28 into the oil-containing product after production of the solid composition; or c) producing an oil-containing product during or as part of the method of claim 1.

30. The method of claim 29, wherein the oil-containing product is selected from the group consisting of a pharmaceutical, a nutraceutical, a food supplement, and a personal care product.

31. An oil-containing product obtained by the method of claim 29.

\* \* \* \* \*